United States Patent
Raines et al.

(10) Patent No.: US 10,154,991 B2
(45) Date of Patent: *Dec. 18, 2018

(54) ANESTHETIC COMPOUNDS AND RELATED METHODS OF USE

(71) Applicants: THE GENERAL HOSPITAL CORPORATION, Boston, MA (US); ANNOVATION BIOPHARMA, INC., Parsippany, NJ (US)

(72) Inventors: Douglas E. Raines, Wayland, MA (US); Syed Shaukat Husain, Newton, MA (US); John C. R. Randle, Brookline, MA (US)

(73) Assignee: Annovation Biopharma, Inc., Parsippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/788,351

(22) Filed: Oct. 19, 2017

(65) Prior Publication Data

US 2018/0098968 A1 Apr. 12, 2018

Related U.S. Application Data

(63) Continuation of application No. 15/348,790, filed on Nov. 10, 2016, now Pat. No. 9,820,971, which is a continuation of application No. 14/808,413, filed on Jul. 24, 2015, now Pat. No. 9,522,136, which is a continuation of application No. 14/371,651, filed as application No. PCT/US2013/021245 on Jan. 11, 2013, now Pat. No. 9,156,825.

(60) Provisional application No. 61/622,627, filed on Apr. 11, 2012, provisional application No. 61/586,450, filed on Jan. 13, 2012.

(51) Int. Cl.
| | |
|---|---|
| *A61K 31/4174* | (2006.01) |
| *A61K 31/454* | (2006.01) |
| *A61K 31/4178* | (2006.01) |
| *A61K 31/40* | (2006.01) |
| *C07D 233/90* | (2006.01) |
| *C07D 401/12* | (2006.01) |
| *C07D 405/12* | (2006.01) |
| *C07D 233/54* | (2006.01) |
| *C07D 401/06* | (2006.01) |
| *C07D 405/06* | (2006.01) |

(52) U.S. Cl.
CPC ........ *A61K 31/4174* (2013.01); *A61K 31/40* (2013.01); *A61K 31/4178* (2013.01); *A61K 31/454* (2013.01); *C07D 233/54* (2013.01); *C07D 233/90* (2013.01); *C07D 401/06* (2013.01); *C07D 401/12* (2013.01); *C07D 405/06* (2013.01); *C07D 405/12* (2013.01)

(58) Field of Classification Search
None
See application file for complete search history.

(56) References Cited

U.S. PATENT DOCUMENTS

| | | | |
|---|---|---|---|
| 3,354,173 A | 11/1967 | Godefroi et al. | |
| 4,038,286 A | 7/1977 | Roevens et al. | |
| 4,289,783 A | 9/1981 | Mesens | |
| 5,019,583 A | 5/1991 | Feldman et al. | |
| 5,041,554 A | 8/1991 | Parker et al. | |
| 5,242,939 A | 9/1993 | Sircar | |
| 5,283,341 A | 2/1994 | Tanaka et al. | |
| 5,466,700 A | 11/1995 | Batenhorst et al. | |
| 7,189,859 B2 | 3/2007 | Zolle et al. | |
| 7,825,149 B2 | 11/2010 | Chubb et al. | |
| 8,071,785 B2 | 12/2011 | Langstrom et al. | |
| 8,557,856 B2 | 10/2013 | Raines et al. | |
| 2003/0055023 A1 | 3/2003 | Rajewski et al. | |
| 2003/0181481 A1 | 9/2003 | Carson et al. | |
| 2008/0206138 A1 | 8/2008 | Zolle et al. | |
| 2009/0297447 A1 | 12/2009 | Langstrom et al. | |
| 2011/0053998 A1 | 3/2011 | Raines et al. | |

FOREIGN PATENT DOCUMENTS

| | | |
|---|---|---|
| CA | 1066709 A | 11/1979 |
| CA | 2636787 A1 | 8/2007 |
| CA | 2692824 A1 | 1/2009 |
| CA | 2720228 A1 | 12/2009 |

(Continued)

OTHER PUBLICATIONS

Arden et al., "Increased Sensitivity to Etomidate in the Elderly: Initial Distribution versus Altered Brain Response", Anesthesiology 65:19-27 (1986).

Atucha et al., "Structure—activity relationship of etomidate derivatives at the GABAA receptor: Comparison with binding to 11β-hydroxylase", Bioorganic & Medicinal Chemistry Letters 19:4284-4287 (2009).

Chivikas et al., "Phenacyl-Directed Alkylation of Imidazoles: A New Regiospecific Synthesis of 3-Substituted L-Histidines", The Journal of Organic Chemistry 52(16):3591-3594 (1987).

Cotten et al., "Methoxycarbonyl-etomidate: A Novel Rapidly Metabolized and Ultra-Short Acting Etomidate Analogue That Does Not Produce Prolonged Adrenocortical Suppression", Anesthesiology 111(2):240-249 (2009).

(Continued)

*Primary Examiner* — Samantha L Shterengarts
(74) *Attorney, Agent, or Firm* — David S. Resnick; Nixon Peabody LLP

(57) ABSTRACT

Provided herein are compounds according to formula (I):

FORMULA (I)

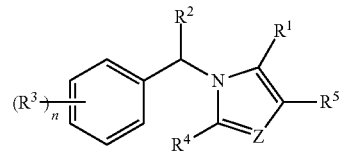

Provided herein is also a pharmaceutical composition comprising a compound according to formula (I) and a pharma- (Continued)

ceutically acceptable carrier, and a method for providing anesthesia in a subject by administering such a pharmaceutical composition.

20 Claims, 6 Drawing Sheets

(56) References Cited

FOREIGN PATENT DOCUMENTS

| EP | 0277384 A2 | 8/1988 |
|---|---|---|
| EP | 0289066 A1 | 11/1988 |
| EP | 0381141 A2 | 8/1990 |
| JP | 06-345728 | 12/1994 |
| WO | 96/39137 A1 | 12/1996 |
| WO | 96/39197 A1 | 12/1996 |
| WO | 2006/023844 A2 | 3/2006 |
| WO | 2007/144725 A2 | 12/2007 |
| WO | 2009/146024 A1 | 12/2009 |
| WO | 2011/005969 A2 | 1/2011 |

OTHER PUBLICATIONS

Cui et al., "Chemoselective Asymmetric N-Allylic Alkylation of Indoles with Morita-Baylis-Hillman Carbonates", Angewandte Chemie International Edition 48:5737-5740 (2009).
Dales et al., "Substrate-Based Design of the First Class of Angiotensin-Converting Enzyme-Related Carboxypeptidase (ACE2) Inhibitors", Journal of the American Chemical Society 124(40):11852-11853 (2002).
Database Caplus, "Chemical Abstracts: Heykants et al., "Distribution, metabolism, and excretion of etomidate, a short-acting hypnotic drug, in the rat. Comparative study of (R)-(+) and (S)-(−)-etomidate"—STN Database accession No. 1975:541712", (1975).
Database Registry, "Chemistry Abstracts: Database Accession No. 205829-25-0", (1998).
David et al., "Novel Routes to Chiral 2-Alkoxy-5-/6-methoxycarbonylmethylidenepyrrolidines/-piperidines", The Journal of Organic Chemistry 69(8):2888-2891 (2004).
Davies et al., "Ring Closing Metathesis for the Asymmetric Synthesis of (S)-Homopipecolic Acid, (S)-Homoproline and (S)-Coniine", Synlett 7:1146-1148 (2002).
De Coster et al., "Comparison of the effects of etomidate and its fluoro analogue, R 8110, on plasma cortisol, 11β-deoxycortisol, 17α-hydroxyprogesterone and testosterone concentrations in dogs", Journal of Veterinary Pharmacology and Therapeutics 10:227-232 (1987).
De Coster et al., "Comparative effects of etomidate and its fluoro analogue, R 8110 on testicular, adrenal and ovarian steroid biosynthesis", Journal of Veterinary Pharmacology and Therapeutics 11:345-353 (1988).
De Jong et al., "Etomidate Suppresses Adrenocortical Fuction by Inhibition of 11β-Hydroxylation", Journal of Clinical Endocrinology and Metabolism 59(6):1143-1147 (1984).
Earle et al., "Alkylation Reactions of N-Alkylpyrroles Resulting in the Diastereoselective Formation of Diarylacetic Esters", Synlett 745-747 (1992).
Ferris et al., "New Chiral Rhodium(II) Carboxylates and their Use as Catalysts in Carbenoid Transformations", Tetrahedron Letters 37(1):107-110 (1996).
Ge et al., "Pharmacological Studies of Methoxycarbonyl Etomidate's Carboxylic Acid Metabolite", Anesthesia & Analgesia 115(2):305-308 (2012).
Godefroi et al., "DL-1-(1-Arylalkyl)imidazole-5-carboxylate Esters. A Novel Type of Hypnotic Agents", Journal of Medicinal Chemistry 8:220-223 (1965).
Hotchkiss et al., "The Pathophysiology and Treatment of Sepsis", The New England Journal of Medicine 348 (2):138-150 (2003).
Husain et al., "2-(3-Methyl-3H-diaziren-3-yl)ethyl 1-(1-phenylethyl)-1H-imidazole-5-carboxylate: A Derivative of the Stereoselective General Anesthetic Etomidate for Photolabeling Ligand-Gated Ion Channels", Journal of Medicinal Chemistry 46(7):1257-1265 (2003).
Husain et al., "Synthesis of Trifluoromethylaryl Diazirine and Benzophenone Derivatives of Etomidate that Are Potent General Anesthetics and Effective Photolabels for Probing Sites on Ligand-Gated Ion Channels", Journal of Medicinal Chemistry 49(16):4818-4825 (2006).
Husain et al., "p-Trifluoromethyldiazirinyl-etomidate: A Potent Photoreactive General Anesthetic Derivative of Etomidate That Is Selective for Ligand-Gated Cationic Ion Channels", Journal of Medicinal Chemistry 53 (17):6432-6444 (2010).
Husain et al., "Modifying Methoxycarbonyl Etomidate Inter-Ester Spacer Optimizes In Vitro Metabolic Stability and In Vivo Hypnotic Potency and Duration of Action", Anesthesiology 117(5):1027-1036 (2012).
Ito et al., "A medium-term rat liver bioassay for rapid in vivo detection of carcinogenic potential of chemicals", Cancer Science 94(1):3-8 (2003).
Jagr et al., "Synthesis and Characterization of Styrene Oxide Adducts with Cysteine, Histidine and Lysine in Human Globin", Chemical Research in Toxicology 20(10):1442-1452 (2007).
Jurd et al., "General anesthetic actions in vivo strongly attenuated by a point mutation in the GABAA receptor in subunit", The FASEB Journal (2002). (21 pages).
Kubinyi, "Multiple Binding Modes", 3D QSAR in Drug Design: Theory Methods and Applications (1998). (6 pages).
Lamberts et al., "Differential Effects of the Imidazole Derivatives Etomidate, Ketoconazole and Miconazole and of Metyrapone of the Secretion of Cortisol and its Precursors by Human Adrenocortical Cells", The Journal of Pharmacology and Experimental Therapeutics 240(1):259-264 (1987).
Li et al, "Identification of a GABAA Receptor Anesthetic Binding Site at Subunit Interfaces by Photolabeling with an Etomidate Analog", The Journal of Neuroscience 26(45):11599-11605 (2006).
Pejo et al., "Electroencephalographic Recovery, Hypnotic Emergence, and the Effects of Metabolite Following Continuous Infusions of a Rapidly Metabolized Etomidale Analog in Rats", Anesthesiology 116(5):1057-1065 (2012).
Pejo et al., "In Vivo and In Vitro Pharmacological Studies of Methoxycarbonyl-Carboetomidate", Anesthesia & Analgesia 115(2):297-304 (2012).
Pessina et al., "Cortisol secretion after adrenocorticotrophin (ACTH) and Dexamethasone tests in healthy female and male dogs", Acta Veterinaria Scandinavica 51:33 (2009). (6 pages).
Podust et al., "Crystal structure of cytochrome P450 14α-sterol demethylase (CYP51) from Mycobacterium tuberculosis in complex with azole inhibitors", Proceedings of the National Academy of Sciences 98(6):3068-3073 (2001).
Polinsky A., "High-Speed Chemistry Libraries: Assessment of Drug-Likeness", The Practice of Medicinal Chemistry 147-157 (2003).
Ray et al., "Effect of induction agent on vasopressor and steroid use, and outcome in patients with septic shock", Critical Care 11(3):R56 (2007). (8 pages).
Roumen et al., "Construction of 3D models of CYP11B family as a tool to predict ligand binding characteristics", Journal of Computer-Aided Molecular Design 21:455-471 (2007).
Rusch et al., "Gating Allosterism at a Single Class of Etomidale Sites on α1β2γ2L GABAA Receptors Accounts for Both Direct Activation and Agonist Modulation", The Journal of Biological Chemistry 279(20):20982-20992 (2004).
Sircar et al., "Nonpeptide Angiotensin II Receptor Antagonists. 1. Synthesis and in Vitro Structure-Activity Relationships of [[[(1 H-Pyrrol-1-ylacetyl)amino]phenyl]methyl]imidazole Derivatives as Angiotensin II Receptor Antagonists", Journal of Medicinal Chemistry 36(12):1735-1745 (1993).
Sprung et al., "Hydrocortisone Therapy for Patients with Septic Shock", The New England Journal of Medicine 358 (2):111-124 (2008).
Stevens et al., "Chemistry and Structure of Mitomycin C1", Journal of Medicinal Chemistry 8(1): (1964).

(56) References Cited

OTHER PUBLICATIONS

Stewart et al., "Tryptophan Mutations at Azi-Etomidate Photo-Incorporation Sites on α1 or β2 Subunits Enhance GABAA Receptor Gating and Reduce Etomidate Modulation", Molecular Pharmacology 74(6):1687-1695 (2008).
Swain et al., "Geometric Preferences of Crosslinked Protein-Derived Cofactors Reveal a High Propensity for Near-Sequence Pairs", Proteins:Structure, Function, and Bioinformatics 59:64-71 (2005).
Teng et al., "Structure-activity relationship and liver microsome stability studies of pyrrole necroptosis inhibitors", Bioorganic & Medicinal Chemistry Letters 18:3219-3223 (2008).
Terfloth et al., "Electronic Screening: Lead Finding From Database Mining", The Practice of Medicinal Chemistry 131-145 (2003).
Van Dijk et al., "R 8110, a new short-acting hypnotic in dogs", Research in Veterinary Science 42:200-203 (1987).
Verras et al., "Cytochrome P450 active site plasticity: attenuation of imidazole binding in cytochrome P450cam by an L244A mutation", Protein Engineering, Design & Selection 19(11):491-496 (2006).
Watt et al., "Mortality amongst multiple trauma patients admitted to an intensive therapy unit", Anaesthesia 39:973-981 (1984).
Xu et al., "Catecholamine and Histidyl Protein Cross-Linked Structures in Sclerotized Insect Cuticle", Insect Biochemistry and Molecular Biology 27(2):101-108 (1997).
Zhao et al., "Structure of Microsomal Cytochrome P450 2B4 Complexed with the Antifungal Drug Bifonazole:Insight Into P450 Conformational Plasticity and Membrane Interaction", The Journal of Biological Chemistry 281(9):5973-5981 (2006).

ANESTHETIC COMPOUNDS AND RELATED METHODS OF USE

RELATED APPLICATIONS

This application is a continuation application of U.S. application Ser. No. 15/348,790 filed Nov. 10, 2016, now U.S. Pat. No. 9,820,971, issued on Nov. 21, 2017, which is a continuation application of U.S. application Ser. No. 14/808,413 filed Jul. 24, 2015, now U.S. Pat. No. 9,522,136, issued on Dec. 20, 2016, which is a continuation application of U.S. application Ser. No. 14/371,651 filed Jul. 10, 2014, now U.S. Pat. No. 9,156,825, issued on Oct. 13, 2015, which is a 35 U.S.C. § 371 National Phase Entry Application of International Application No. PCT/US2013/021245 filed Jan. 11, 2013, which designates the U.S., and which claims benefit under 35 U.S.C. § 119(e) of the U.S. Provisional Application No. 61/586,450, filed Jan. 13, 2012, and U.S. Provisional Application No. 61/622,627, filed Apr. 11, 2012, the contents of each of which are incorporated herein by reference in their entirety.

GOVERNMENT SUPPORT

This invention was made with Government support under Grant No. R01-GM087316 awarded by the National Institutes of Health. The Government has certain rights in the invention.

TECHNICAL FIELD

The disclosure relates to metomidate and etomidate analogues that have improved pharmacokinetic and pharmacodynamic properties, and their uses, for example as anesthetics.

BACKGROUND

There is a great need for safer general anesthetics for use in critically ill patients, and particularly for patients with sepsis. (R)-Etomidate possesses many properties that would make it an ideal anesthetic agent (e.g. high anesthetic potency, lesser effects on cardiovascular function and higher therapeutic index than other agents) if it were not such a potent inhibitor of adrenocortical function.

Etomidate is an imidazole-based intravenous hypnotic that is frequently used to induce anesthesia in the elderly and critically ill because it maintains hemodynamic stability better than other anesthetic agents.[1-3] Unfortunately, etomidate also produces adrenocortical suppression, a side effect that can persist for days after etomidate administration.[4-8] This potentially deadly side effect has caused clinicians to abandon the use of etomidate infusions and led to concerns regarding the administration of even a single intravenous (IV) bolus dose for anesthetic induction.[9-11] In a previous study, the inventors developed methoxycarbonyl etomidate (MOC-etomidate) as the prototypical member of a new class of "etomidate esters" that, similar to remifentanil and esmolol, contains a metabolically-labile ester moiety that is rapidly hydrolyzed by esterases (FIG. 1).[12] Inventors showed that MOC-etomidate is rapidly hydrolyzed in rat blood and human liver s9 fraction and produces hypnosis and adrenocortical suppression of extremely short duration when administered to rats as an IV bolus.[12,13]

A key feature of soft drugs is that their metabolic stabilities and durations of action must fall within an optimal range to be clinically useful.[14] A drug that is too rapidly metabolized and short-acting will require the administration of impractically large quantities to maintain a therapeutic effect and may produce metabolite concentrations sufficient to produce undesirable side effects when given for a prolonged period of time. Conversely, a drug that is too slowly metabolized and long acting will have pharmacokinetic properties that are not meaningfully different from the metabolically stable "hard" drug from which it was derived.

Because esterase activity varies significantly among species, it is difficult to predict from small animal studies whether any particular soft drug's pharmacokinetic profile will fall within the optimal range when administered to humans.[15]

SUMMARY

Provided herein are compounds according to formula (I):

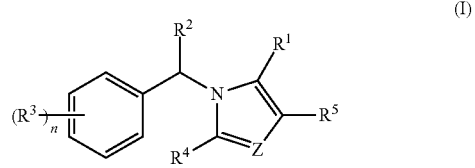

wherein,
$R^1$ is $L^1C(O)OL^2$-$[C(R^7R^8)]_p$—$C(R^9R^{10})$—$C(O)OT$;
$R^2$ is $R^1$, optionally substituted linear or branched $C_1$-$C_{10}$ alkyl, optionally substituted linear or branched $C_2$-$C_{10}$ alkenyl, or optionally substituted linear or branched $C_2$-$C_{10}$ alkynyl;
each $R_3$ is independently halogen, CN, $CF_3$, $SR^2$, $SOR^2$, $SO_2R^2$, $OR^2$, $CO_2H$, $CO_2R^2$, $N(R^2)_2$, $NHR^2$, $NO_2$, or $R^2$;
Z is N or $CR^6$;
$R^4$, $R^5$, and $R^6$ are independently hydrogen, halogen, CN, $CF_3$, $SR^2$, $SOR^2$, $SO_2R^2$, $OR^2$, $CO_2H$, $CO_2R^2$, $N(R^2)_2$, $NHR^2$, $NO_2$, or $R^2$;
$R^7$ and $R^8$ are independently hydrogen, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, or $R^7$ and $R^8$ together with the carbon they are attached to form an optionally substituted 3-8 membered cyclyl or heterocyclyl;
$R^9$ and $R^{10}$ are independently hydrogen, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted $C_4$-$C_8$ cyclyl, optionally substituted $C_3$-$C_8$ heterocyclyl, or $R^9$ and $R^{10}$ together with the carbon they are attached to form an optionally substituted 3-8 membered cyclyl or heterocyclyl, or $R^7$ and $R^9$ together with the carbons they are attached to form an optionally substituted 3-8 membered cyclyl, heterocyclyl, aryl or heteroaryl;
$L^1$ and $L^2$ are independently a bond, optionally substituted linear or branched $C_1$-$C_{10}$ alkylene, optionally substituted linear or branched $C_2$-$C_{10}$ alkenylene, or optionally substituted linear or branched $C_2$-$C_{10}$ alkynylene;
T is H, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, optionally substituted heteroaryl, or PEG, wherein the backbone of $C_1$-$C_{10}$ alkyl, $C_2$-$C_{10}$ alkenyl, $C_2$-$C_{10}$ alkynyl can contain one or more heteroatoms;

n is an integer from 0-5; and p is 0 or 1, provided that at least one of $R^7$, $R^8$, $R^9$ and $R^{10}$ is not hydrogen, or a salt, solvate, or ester thereof.

Compounds of formula (I) are analogues of etomidate that retain (R)-etomidate's beneficial anesthetic properties, but do not cause clinically significant inhibition of adrenocortical function. However, unexpectedly compounds of formula (I) have improved enhanced duration of action as compared to etomidate analogues and derivatives described in PCT Publication No. WO 2011/005969 and US Patent Application Publication No. 2011/0053998. Accordingly, compounds of formula (I) have improved pharmacokinetic and pharmacodynamic properties over (R)-etomidate that allow for equivalent or improved anesthetic properties along with a reduction in undesirable side effects.

In various cases, the compounds disclosed herein can have a structure of formula (IA), (IB), or (IC):

(IA)

(IB)

(IC)

Also disclosed herein are methods of preparing compounds having a structure of formula (I) comprising coupling a compound of formula (II) and (a) a compound of formula (III) or (b) a compound of formula (IV):

(II)

(III)

(IV)

wherein $R^2$, $R^3$, $R^4$, $R^5$, $R^6$, and n are as defined for formula (I) and X is a carboxylic acid protecting group; removing X to form a carboxylic acid; coupling the carboxylic acid with an alcohol of structure $HOL^2$-$[C(R^7R^8)]_p$—$C(R^9R^{10})$—$C(O)OT$, wherein $L^2$, $R^7$, $R^8$, $R^9$, $R^{10}$, T and p are as defined for formula (I).

In another aspect, provided herein is a pharmaceutical anesthetic composition, comprising an effective amount of a compound according to formula (I) and a pharmaceutically acceptable carrier.

Further disclosed herein are methods of providing anesthesia or sedation to a subject comprising administering to the subject an effective amount of a compound as disclosed herein. Also disclosed are uses of compounds disclosed herein as an anesthetic or sedative.

In yet still another aspect, provided herein is use of the compounds of formula (I) as described herein as a formulation for, or in the manufacture of a formulation for providing anesthesia or sedation in a subject in need thereof.

DETAILED DESCRIPTION

Figure 1:
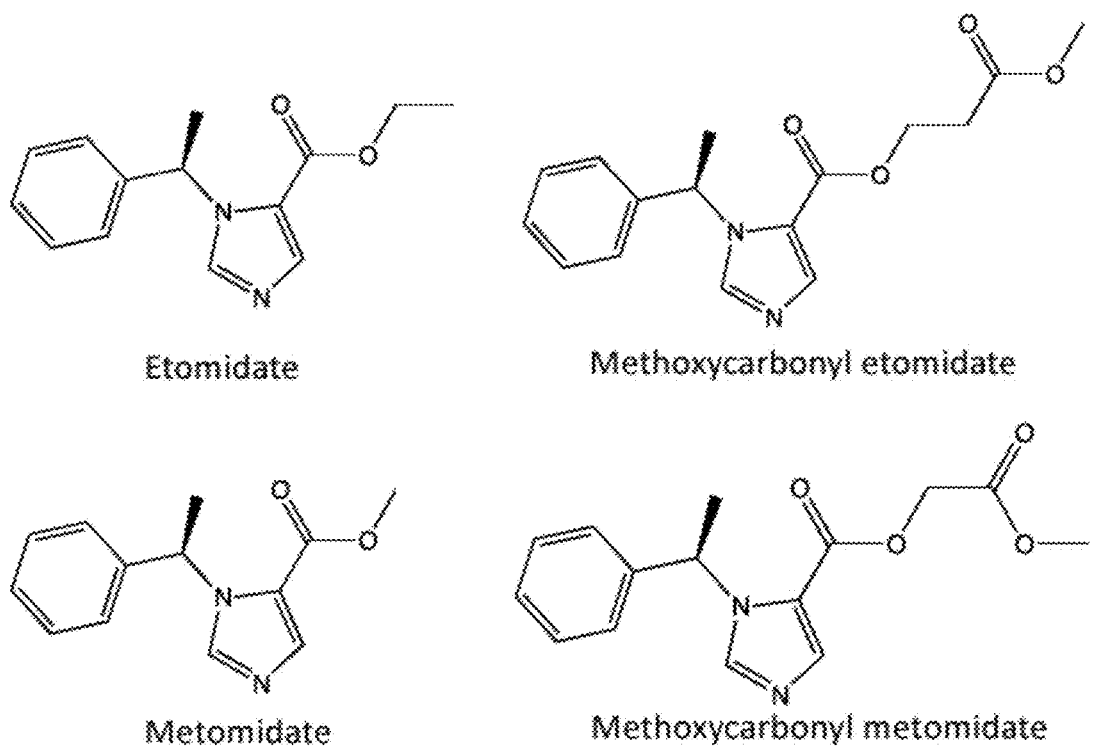
FIG. 1 shows structures of various compounds.

As mentioned above, because esterase activity varies significantly among species, it is difficult to predict from small animal studies whether any particular soft drug's pharmacokinetic profile will fall within the optimal range when administered to humans. Early preclinical studies typically use rodents, which are assumed to metabolize ester-containing drugs much faster than humans and other large animals.[16-18] However, that generality is not without exception and preliminary studies in dogs and monkeys indicated that methoxycarbonyl etomidate's duration of action in large animals is similar to that in rats (1-2 min).

This indicates that methoxycarbonyl etomidate may be too short-acting for widespread clinical use.

Thus, there is a need in the art to develop analogues of (R)-etomidate that retain its many beneficial properties (e.g. rapid onset of action, little effect on blood pressure, high therapeutic index), but do not cause potentially dangerous inhibition of adrenocortical function and have acceptable duration of action. Such analogues will permit anesthesia to be administered more safely to patients who are critically ill.

This disclosure relates to safer analogues of etomidate that retain its beneficial characteristics (e.g. potent anesthetic, rapid onset of anesthesia, little effect on blood pressures), but whose impact on adrenocortical steroid synthesis is substantially reduced. Certain embodiments include analogues of etomidate that are so rapidly metabolized that inhibition of 11β-hydroxylase terminates shortly after discontinuing anesthetic administration. For example, inhibition of 11β-hydroxylase can terminate within about 2 hours, 1.5 hours, 1 hour, 45 minutes, 30 minutes, 20 minutes, 15 minutes, 10 minutes, or 5 minutes after discontinuing anesthetic administration. The disclosed analogues of etomidate bind with lower affinity to 11β-hydroxylase. For example, the disclosed analogues can bind to 11β-hydroxylase with an affinity that is about 95%, 90%, 85%, 80%, 75%, 70%, 65%, 60%, 55%, 50%, 45%, 40%, 35%, 30%, 25%, 20%, 15%, 10% or less than the binding affinity of etomidate to 11β-hydroxylase.

The compounds described herein can be understood as analogues of etomidate (either R- or S-enantiomer) augmented with one or more additional metabolically-labile ester moieties attached to various positions of the core molecule directly or via various linker groups. Distal to the ester moieties, there can be a "tail" group (for example, —CH₃). The metabolically-labile ester groups can comprise one or two alkyl, alkenyl, or alkynyl substituents on the α carbon or β carbon of the ester carbonyl group. Without wishing to be bound by a theory, the presence of such a substituent is believed to reduce the rate of hydrolysis of the ester thus increasing the duration of action of the compound. The compounds described herein can also be understood as analogues of etomidate (either R- or S-enantiomer) wherein the basic nitrogen in the imidazole ring has been replaced with a CH group. Without wishing to be bound by theory, it is believed that replacement of basic nitrogen with CH group reduces the binding affinity of these compounds for 11β-hydroxylase. These compounds can be further augmented with one or more additional metabolically-labile ester moieties attached to various positions of the core molecule directly or via various linker groups. Distal to the ester moieties, there can be a "tail" group (for example, —CH₃). The metabolically-labile ester groups can comprise one or two alkyl, alkenyl, or alkynyl substituents on the α carbon or β carbon of the ester carbonyl group. The various embodiments of these compounds are discussed below.

In one aspect, provided herein are compounds according to formula (I):

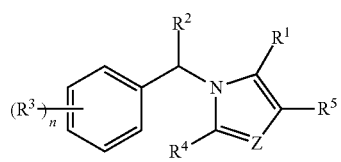

(I)

wherein, $R^1$ is $L^1C(O)OL^2$-$[C(R^7R^8)]_p$—$C(R^9R^{10})$—$C(O)OT$;

$R^2$ is $R^1$, optionally substituted linear or branched $C_1$-$C_{10}$ alkyl, optionally substituted linear or branched $C_2$-$C_{10}$ alkenyl, or optionally substituted linear or branched $C_2$-$C_{10}$ alkynyl;

each $R_3$ is independently halogen, CN, $CF_3$, $SR^2$, $SOR^2$, $SO_2R^2$, $OR^2$, $CO_2H$, $CO_2R^2$, $N(R^2)_2$, $NHR^2$, $NO_2$, or $R^2$;

Z is N or $CR^6$;

$R^4$, $R^5$, and $R^6$ are independently hydrogen, halogen, CN, $CF_3$, $SR^2$, $SOR^2$, $SO_2R^2$, $OR^2$, $CO_2H$, $CO_2R^2$, $N(R^2)_2$, $NHR^2$, $NO_2$, or $R^2$;

$R^7$ and $R^8$ are independently hydrogen, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, or $R^7$ and $R^8$ together with the carbon they are attached to form an optionally substituted 3-8 membered cyclyl or heterocyclyl;

$R^9$ and $R^{10}$ are independently hydrogen, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted $C_4$-$C_8$ cyclyl, optionally substituted $C_3$-$C_8$ heterocyclyl, or $R^9$ and $R^{10}$ together with the carbon they are attached to form an optionally substituted 3-8 membered cyclyl or heterocyclyl, or $R^7$ and $R^9$ together with the carbons they are attached to form an optionally substituted 3-8 membered cyclyl, heterocyclyl, aryl or heteroaryl;

$L^1$ and $L^2$ are independently a bond, optionally substituted linear or branched $C_1$-$C_{10}$ alkylene, optionally substituted linear or branched $C_2$-$C_{10}$ alkenylene, or optionally substituted linear or branched $C_2$-$C_{10}$ alkynylene;

T is H, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, optionally substituted heteroaryl, or PEG, wherein the backbone of $C_1$-$C_{10}$ alkyl, $C_2$-$C_{10}$ alkenyl, or $C_2$-$C_{10}$ alkynyl can contain one or more heteroatoms;

n is an integer from 0-5; and p is 0 or 1, provided that at least one of $R^7$, $R^8$, $R^9$ and $R^{10}$ is not hydrogen.

The compounds of formula (I) include pharmaceutically acceptable salts, solvates, esters, stereoisomer mixtures, and enantiomers thereof.

Additional optional features of such compounds are described below, and are contemplated as further characterizing the compounds of formula (I) individually and/or in combination with each other, without limit.

In some embodiments, p is 0 or 1.

In various embodiments, the backbone of $C_1$-$C_{10}$ alkyl, $C_2$-$C_{10}$ alkenyl, or $C_2$-$C_{10}$ alkynyl can comprise one or more heteroatoms, such as O, N, or S.

In various cases, $R^2$ is an optionally substituted $C_1$-$C_{10}$ alkyl. In some embodiments, $R^2$ is selected from the group consisting of methyl, ethyl, propyl, isopropyl, butyl, t-butyl, pentyl, neopentyl, hexyl, 2-methylpentyl, 3-methylpentyl, 2,3-dimethylbutyl, and 2,2-dimethylbutyl. In some embodiments, $R^2$ is methyl or ethyl. In some embodiments $R^2$ can be an ester of $R^1$, such as $CH_2CH_2C(O)OCH_3$.

A skilled artisan recognizes that the carbon atom to which the $R^2$ substituent is attached is a chiral center. Therefore, the compound can be in the form of a pure enantiomer. In some embodiments, the carbon to which the $R^2$ substituent is attached is in the R configuration. In other embodiments, the carbon to which the $R^2$ substituent is attached is in the S configuration.

The variable n is an integer from 0 to 5. In some embodiments, n ranges from 0-3. In some specific embodiments, n is 0 or 1. In some more specific embodiments, n is 0. Accordingly, when present, each of $R^3$ is independently halogen, halogen, CN, $CF_3$, $SR^2$, $SOR^2$, $SO_2R^2$, $OR^2$, $CO_2H$, $CO_2R^2$, $N(R^2)_2$, $NHR^2$, $NO_2$, or $R^2$. In some cases, substituent $R^3$ can be halogen or an electron withdrawing group. In some embodiments, $R^3$ is fluorine or chlorine.

In some cases, $R^4$ is hydrogen, halogen, CN or $CF_3$. In some embodiments, $R^4$ is Br or CN.

In some embodiments, $R^5$ is hydrogen.

In various cases, Z is N. In alternative cases, Z is $CR^6$. In some cases, $R^6$ is hydrogen, halogen, CN or $CF_3$. In some cases, $R^6$ is hydrogen. In some embodiments, $R^6$ is Br or CN.

In some cases, at least one of $R^4$ and $R^6$ is Br or CN.

In various cases, $R^7$ and $R^8$ are independently hydrogen, optionally substituted $C_1$-$C_{10}$alkyl, optionally substituted $C_4$-$C_6$cyclyl or optionally substituted $C_4$-$C_6$heterocyclyl; or $R^7$ and $R^8$ together with the carbon they are attached to form a 3-, 4-, 5, or 6-membered cyclyl.

In various cases, $R^7$ and $R^8$ are independently hydrogen, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl.

In some embodiments, at least one of $R^7$, $R^8$, $R^9$ and $R^{10}$ is an optionally substituted linear or branched $C_1$-$C_{10}$ alkyl, optionally substituted linear or branched $C_2$-$C_{10}$ alkenyl, or optionally substituted linear or branched $C_2$-$C_{10}$ alkynyl. The $C_1$-$C_{10}$ alkyl, $C_2$-$C_{10}$ alkenyl, or $C_2$-$C_{10}$ alkynyl backbone can comprise one or more heteroatoms, such as O, N, or S.

In some embodiments, at least one of $R^7$, $R^8$, $R^9$ and $R^{10}$ is an optionally substituted 3-8 membered cyclyl or heterocyclyl. Some specific examples of the 3-8 membered cyclyl or heterocyclyl include phenyl, pyridyl, thiophene, furanyl, pyrazolyl, cyclohexyl, cyclohexenyl, cyclopentyl, cyclopentenyl, and piperdinyl.

In various cases, $R^7$ and $R^8$, $R^9$ and $R^{10}$ are independently hydrogen, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, provided that at least one of $R^7$, $R^8$, $R^9$ and $R^{10}$ is not a hydrogen, i.e., at least one of $R^7$, $R^8$, $R^9$ and $R^{10}$ is an optionally substituted linear or branched $C_1$-$C_{10}$ alkyl, optionally substituted linear or branched $C_2$-$C_{10}$ alkenyl, or optionally substituted linear or branched $C_2$-$C_{10}$ alkynyl. The $C_1$-$C_{10}$ alkyl, $C_2$-$C_{10}$ alkenyl, or $C_2$-$C_{10}$ alkynyl backbone can comprise one or more heteroatoms, such as O, N, or S.

In some embodiments, $R^7$, $R^8$, $R^9$ and $R^{10}$ are selected from the group consisting of methyl, ethyl, propyl, isopropyl, butyl, t-butyl, pentyl, neopentyl, hexyl, 2-methylpentyl, 3-methylpentyl, 2,3-dimethylbutyl, and 2,2-dimethylbutyl.

$R^9$ and $R^{10}$ can be different or can be both the same. In some embodiments, one of $R^9$ and $R^{10}$ is hydrogen and the other is an optionally substituted linear or branched $C_1$-$C_{10}$ alkyl. In some embodiments, one of $R^9$ and $R^{10}$ is methyl, ethyl, propyl, or isopropyl. In some embodiments, $R^9$ and $R^{10}$ are both methyl. In some embodiments, $R^9$ and $R^{10}$ together with the carbon they are attached to form a 3 membered ring.

A skilled artisan would recognize that when $R^9$ and $R^{10}$ are different, the carbon to which they are attached to can be in the R or S configuration. Accordingly, in some embodiments, the carbon to which $R^9$ and $R^{10}$ are attached is in the R configuration. In some other embodiments, the carbon to which $R^9$ and $R^{10}$ are attached is in the S configuration.

When present, $R^7$ and $R^8$ can be different or can be the same. In some embodiments, one of $R^7$ and $R^8$ is hydrogen and the other is an optionally substituted linear or branched $C_1$-$C_{10}$ alkyl. In some embodiments, one of $R^7$ and $R^7$ is methyl, ethyl, propyl, or isopropyl. In some embodiments, $R^7$ and $R^8$ are both methyl. In some embodiments, $R^7$ and $R^8$ together with the carbon they are attached to form a 3 membered ring.

Similar to $R^9$ and $R^{10}$, when $R^7$ and $R^8$ are different, the carbon to which they are attached to can be in the R or S configuration. Accordingly, in some embodiments, the carbon to which $R^7$ and $R^8$ are attached is in the R configuration. In some other embodiments, the carbon to which $R^8$ and $R^8$ are attached is in the S configuration.

In some cases, $R^7$ and $R^8$ are independently hydrogen, optionally substituted linear or branched $C_1$-$C_{10}$alkyl, $C_2$-$C_{10}$alkenyl, or $C_2$-$C_{10}$alkynyl. In various cases, $R^7$ and $R^9$ taken together form an optionally substituted 3-8 membered carbocyclyl, heterocyclyl, aryl, or heteroaryl.

In various cases, $L^1$ is a bond, optionally substituted linear or branched $C_1$-$C_{10}$alkylene, $C_2$-$C_{10}$alkenylene, or $C_2$-$C_{10}$alkynylene; wherein the backbone of $C_1$-$C_{10}$alkylene, $C_2$-$C_{10}$alkenylene, or $C_2$-$C_{10}$alkynylene optionally comprises one or more heteroatoms. In various cases, $L^2$ is a bond, optionally substituted linear or branched $C_1$-$C_{10}$alkylene, $C_2$-$C_{10}$alkenylene, or $C_2$-$C_{10}$alkynylene; wherein the backbone of $C_1$-$C_{10}$alkylene, $C_2$-$C_{10}$alkenylene, or $C_2$-$C_{10}$alkynylene optionally comprises one or more heteroatoms.

Preferably, $L^1$ and $L^2$ are each independently a bond or a linear $C_1$-$C_4$ alkylene group. In some embodiments, $L^1$ is a bond or $CH_2CH_2$. In some embodiments, $L^2$ is $CH_2CH_2$, $CH_2(CH_2)_4CH_2$, or $CH_2CH_2O(CH_2)_3$. In some embodiments, $L^2$ is a bond. In some embodiments, both of $L^1$ and $L^2$ are a bond.

The tail T can be hydrogen or an optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted cyclyl, optionally substituted heterocyclyl, optionally substituted aryl, optionally substituted heteroaryl, or PEG. The backbone of $C_1$-$C_{10}$ alkyl, $C_2$-$C_{10}$ alkenyl, $C_2$-$C_{10}$ alkynyl can contain one or more heteroatoms, such as O, N, or S. In some cases, T is a $C_1$-$C_4$ alkyl group. In some embodiments, T is an optionally substituted methyl, ethyl, propyl, isopropyl, butyl, t-butyl, pentyl, neopentyl, hexyl, 2-methylpentyl, 3-methylpentyl, 2,3-dimethylbutyl, 2,2-dimethylbutyl, or 2-hydroxypropyl. The tail T can also be an electron donating group. In some embodiments, T is hydrogen, methyl, nitrophenol or 2-hydroxypropyl.

In various cases, T is optionally substituted $C_1$-$C_{10}$ alkyl, and specifically contemplated T include methyl and ethyl. In various cases, T is optionally substituted cyclyl or heterocyclyl, and specifically contemplated T include cyclopropyl, cyclobutyl, oxetanyl, morpholinyl, and oxazolindinyl.

In various cases, $L^1$ is an optionally substituted linear or branched $C_1$-$C_{10}$alkylene, $C_2$-$C_{10}$alkenylene, or $C_2$-$C_{10}$alkynylene; wherein the backbone of $C_1$-$C_{10}$alkylene, $C_2$-$C_{10}$alkenylene, or $C_2$-$C_{10}$alkynylene optionally comprises one or more heteroatoms. In various cases, $L^2$ is an optionally substituted linear or branched $C_1$-$C_{10}$alkylene, $C_2$-$C_{10}$alkenylene, or $C_2$-$C_{10}$alkynylene;

wherein the backbone of $C_1$-$C_{10}$alkylene, $C_2$-$C_{10}$alkenylene, or $C_2$-$C_{10}$alkynylene optionally comprises one or more heteroatoms.

In some embodiments, $R^1$ is -$L^2$-$CH_2CH(CH_3)$—, -$L^2$-$CH_2C(CH_3)_2$—, -$L^2$-$CH_2CH(CH(CH_3)_2)$—,

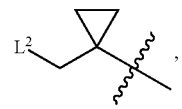

-$L^2$-$CH(CH_3)CH_2$—, -$L^2$-$C(CH_3)_2CH_2$—, -$L^2$-$CH(CH(CH_3)_2)CH2$-, -$L^2$-$CH(CH_3)$—, -$L^2$-$C(CH_3)_2$—, -$L^2$-$CH(CH(CH_3)_2)$—, —$CH_2CH(CH_3)$—, —$CH_2C(CH_3)_2$—, —$CH_2CH(CH(CH_3)_2)$—,

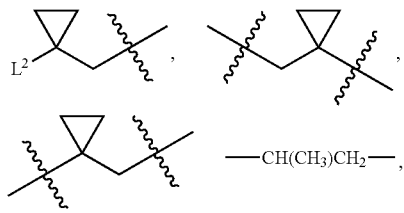

—$C(CH_3)_2CH_2$—, —$CH(CH(CH_3)_2)CH2$-, —$CH(CH_3)$—, —$C(CH_3)_2$—, or —$CH(CH(CH_3)_2)$—.

The compounds of formula (I) can include pharmaceutically acceptable salts, stereoisomer mixtures, and enantiomers thereof. The compounds can also include physiologically acceptable salts of the compounds of formula (I). Preferred physiologically acceptable salts are acid-addition salts known to those of skill in the art. Common physiologically acceptable acid-addition salts include but are not limited to, hydrochloric acid salts, oxalate salts, and tartrate salts.

In some embodiments, $R^1$ and $R^2$ are a bond, and p is 0.
In some other embodiments, $R^1$ and $R^2$ are a bond, and p is 1.

When p is 0, none or one of $R^9$ and $R^{10}$ can be hydrogen. For example, when p is 0, one of $R^9$ and $R^{10}$ is hydrogen and the other can be methyl or isopropyl. In another example, when p is 0, both of $R^9$ and $R^{10}$ are methyl. In yet another example, when p is 0, $R^9$ and $R^{10}$ together with the carbon to which they are attached form a three membered ring, such as cyclopropyl.

When p is 1, none, one, two or three of $R^7$, $R^8$, $R^9$ and $R^{10}$ can be hydrogen. When only two of $R^7$, $R^8$, $R^9$ and $R^{10}$ are hydrogen, the two hydrogens can be attached to the same carbon, i.e., both of $R^7$ and $R^8$ are hydrogen or both of $R^9$ and $R^{10}$ are hydrogen. Without limitations, all combinations of hydrogen locations for $R^7$, $R^8$, $R^9$ and $R^{10}$ are considered herein. For example, both of $R^7$ and $R^8$ are hydrogen and one or both of $R^9$ and $R^{10}$ are not hydrogen or both of $R^9$ and $R^{10}$ are hydrogen and one or both of $R^7$ and $R^8$ are not hydrogen. Accordingly, in some embodiments, $R^7$, $R^8$, and one of $R^9$ and $R^{10}$ are all hydrogen. In some other embodiments, $R^9$, $R^{10}$, and one of $R^7$ and $R^8$ are all hydrogen.

In some embodiments, when p is 1, $R^7$ and $R^8$ are both hydrogen and one of $R^9$ and $R^{10}$ is methyl or isopropyl and the other is hydrogen. In some other embodiments, when p 1 is 1, $R^7$ and $R^8$ are both hydrogen and $R^9$ and $R^{10}$ are same or together with the carbon to which they are attached form a three membered ring. For example, $R^7$ and $R^8$ are both hydrogen and $R^9$ and $R^{10}$ are both methyl.

In some other embodiments, when p is 1, $R^9$ and $R^{10}$ are both hydrogen and one of $R^7$ and $R^8$ is methyl or isopropyl and the other is hydrogen. In yet some other embodiments, when p 1 is 1, $R^9$ and $R^{10}$ are both hydrogen and $R^7$ and $R^8$ are same or together with the carbon to which they are attached form a three membered ring. For example, $R^9$ and $R^{10}$ are both hydrogen and $R^7$ and $R^8$ are both methyl.

When present, $R^6$ can be the same or different from $R^4$ or $R^5$. For example, $R^4$, $R^5$, and $R^6$ and all can be hydrogen; only two of $R^4$, $R^5$, and $R^6$ can be hydrogen; only one of $R^4$, $R^5$, and $R^6$ can be hydrogen; or none of $R^4$, $R^5$, and $R^6$ can be hydrogen. For example, $R^4$ and $R^6$ can both be hydrogen. In another example, one of $R^4$ and $R^6$ can be a halogen or CN and the other can be hydrogen. Accordingly, in some embodiments, $R^6$ is H and $R^4$ is Br or CN. In some other embodiments, $R^4$ is H and $R^6$ is Br or CN.

Similarly, when $R^6$ is absent, i.e., Z is N, $R^4$ and $R^5$ can be the same or different. In one embodiment, Z is N and $R^4$ and $R^5$ are hydrogen.

Compounds of formula (I) preferably have the same stereochemistry as (R)-etomidate. $R^2$, $R^3$, $L^1$, $L^2$, and T can be branched hydrocarbon chains, however, not to the extent that steric hindrance or conjugation interferes with the desired activity.

In certain embodiments, the compound includes two or more ester groups. Suitable ester-containing groups (e.g. linker-ester-tail or ester-tail) can be added to the bridging carbon or at various positions of the phenyl ring or the core molecule.

In various cases, the compound disclosed herein has a structure of formula (IA), (IB), or (IC):

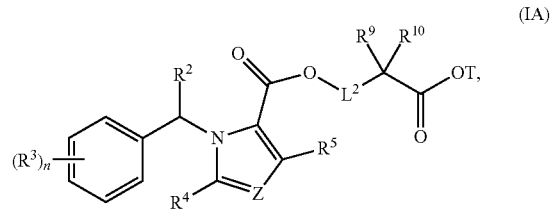

(IA)

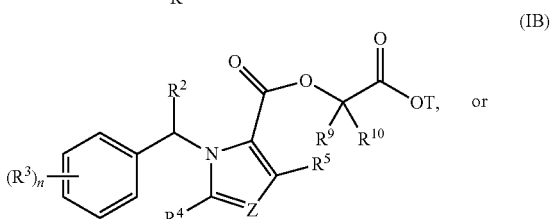

(IB)

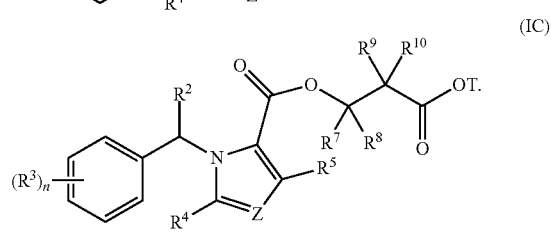

(IC)

In some embodiments, the compound of formula (I) is selected from the group consisting of α-R-methyl-MOC-etomidate, α-S-methyl-MOC-etomidate, α-dimethyl-MOC-etomidate, β-R-methyl-MOC-etomidate, β-S-methyl-MOC-etomidate, β-dimethyl-MOC-etomidate, R-methyl-MOC-metomidate, S-methyl-MOC-metomidate, dimethyl-MOC-metomidate, S-isopropyl-MOC-metomidate, R-isopropyl-MOC-metomidate, cyclopropyl-MOC-metomidate, and pharmaceutically acceptable salts, stereoisomer mixtures, and enantiomers thereof. Structures of the above etomidate analogues are shown in Table 1 in the Examples section below.

Carboetomidate is an analogue of etomidate wherein the basic nitrogen in the imidazole ring is replaced by a CH group. Similarly, carbometomidate is an analogue of metomidate wherein the basic nitrogen in the imidazole ring is replaced by a CH group. Accordingly, in some embodiments, a compound of formula (I) is a carboetomidate analogue.

In some embodiments, the compound of formula (I) is selected from the group consisting of

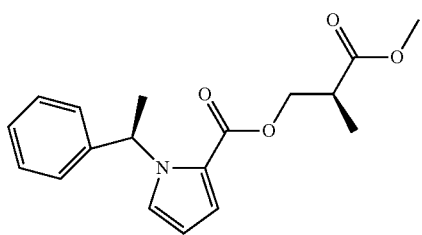 [SMILES: COC(=O)[C@@H](C)COC(=O)c1cccn1[C@H](C)c1ccccc1]

(α-R-methyl-MOC-carboetomidate),

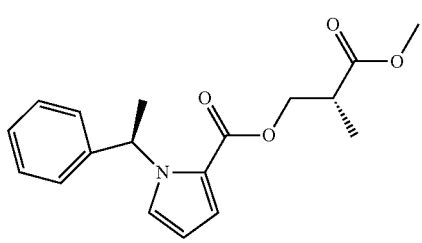 [SMILES: COC(=O)[C@H](C)COC(=O)c1cccn1[C@H](C)c1ccccc1]

(α-S-methyl-MOC-carboetomidate),

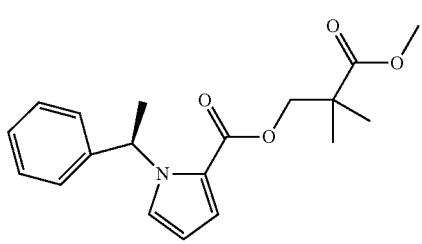 [SMILES: COC(=O)C(C)(C)COC(=O)c1cccn1[C@H](C)c1ccccc1]

(α-dimethyl-MOC-carboetomidate),

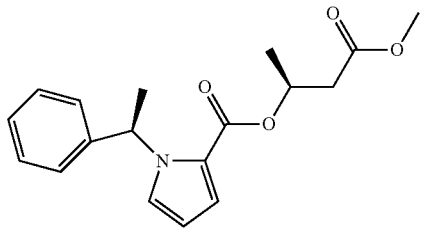 [SMILES: COC(=O)C[C@H](C)OC(=O)c1cccn1[C@H](C)c1ccccc1]

(β-R-methyl-MOC-carboetomidate),

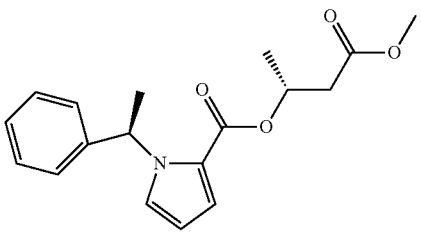 [SMILES: COC(=O)C[C@@H](C)OC(=O)c1cccn1[C@H](C)c1ccccc1]

(β-S-methyl-MOC-carboetomidate),

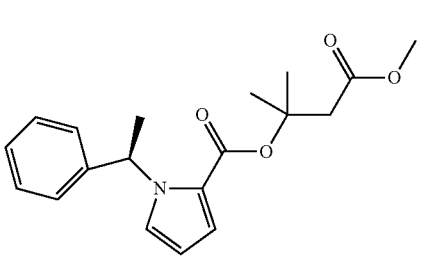 [SMILES: COC(=O)CC(C)(C)OC(=O)c1cccn1[C@H](C)c1ccccc1]

(β-dimethyl-MOC-carboetomidate),

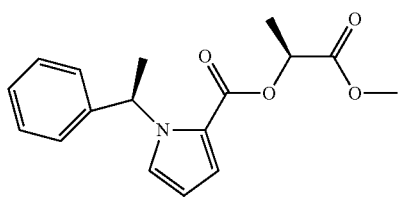 [SMILES: COC(=O)[C@H](C)OC(=O)c1cccn1[C@H](C)c1ccccc1]

(R-methyl-MOC-carbometomidate),

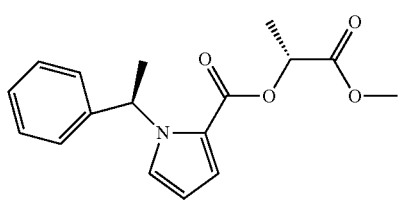 [SMILES: COC(=O)[C@@H](C)OC(=O)c1cccn1[C@H](C)c1ccccc1]

(S-methyl-MOC-carbometomidate),

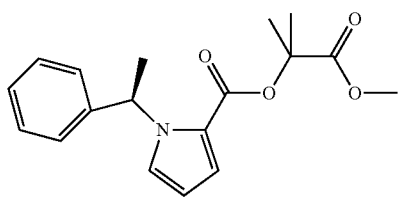 [SMILES: COC(=O)C(C)(C)OC(=O)c1cccn1[C@H](C)c1ccccc1]

(dimethyl-MOC-carbometomidate),

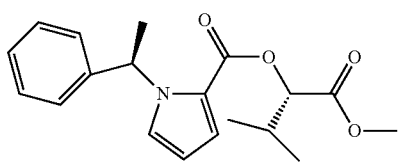 [SMILES: COC(=O)[C@@H](OC(=O)c1cccn1[C@H](C)c1ccccc1)C(C)C]
(S-isopropyl-MOC-carbometomidate),
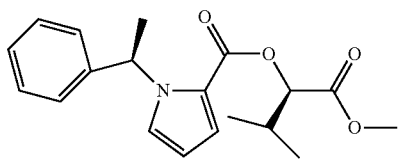 [SMILES: COC(=O)[C@H](OC(=O)c1cccn1[C@H](C)c1ccccc1)C(C)C]
(R-isopropyl-MOC-carbometomidate),
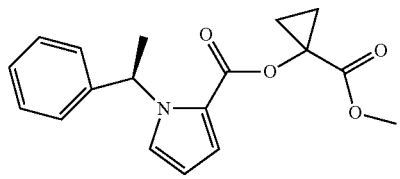 [SMILES: COC(=O)C1(OC(=O)c2cccn2[C@H](C)c2ccccc2)CC1]
(cyclopropyl-MOC-carbometomidate), and pharmaceutically acceptable salts, stereoisomer mixtures, and enantiomers thereof.
Other exemplary compounds of formula (I) include:
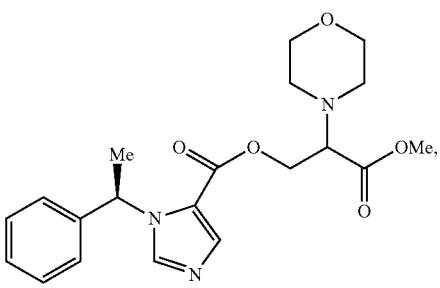
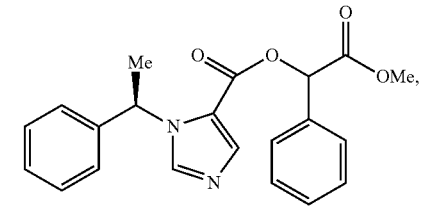
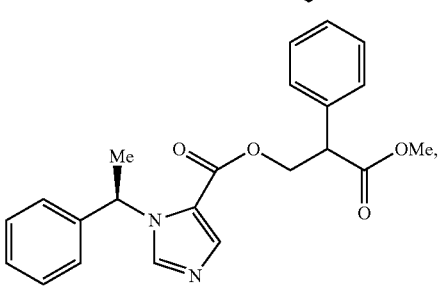
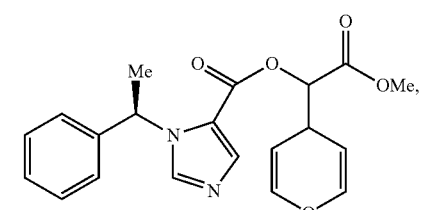
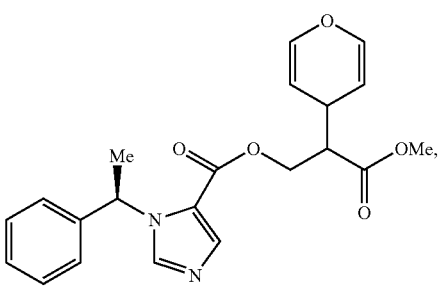
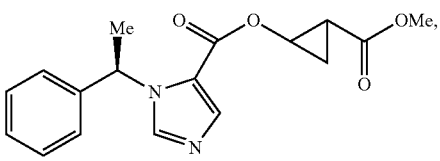
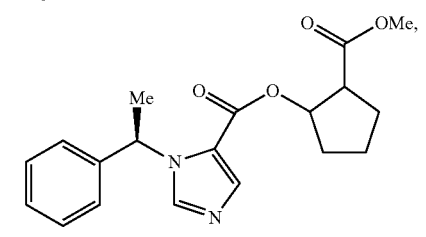
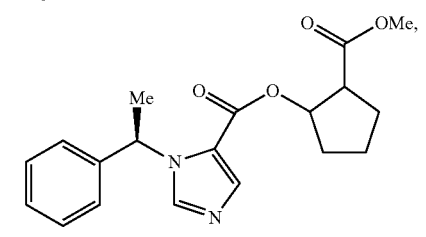
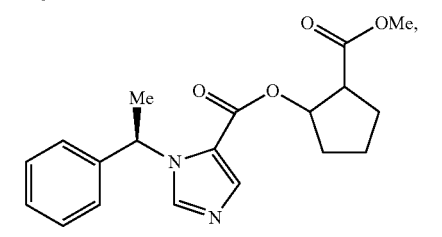
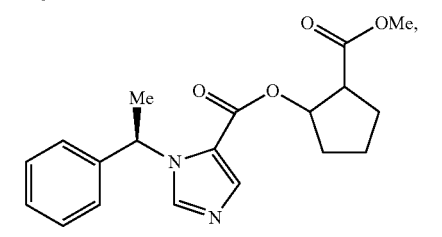
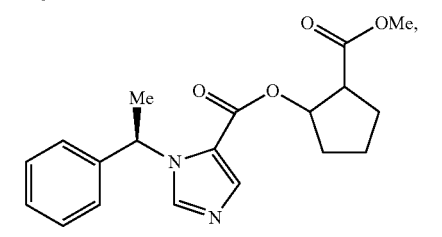
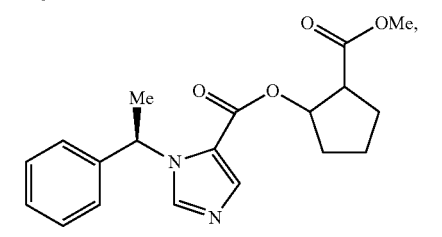
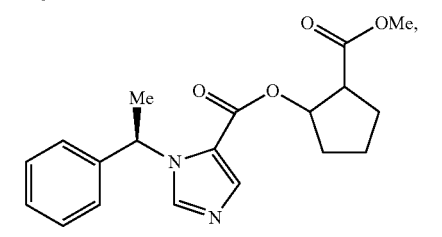

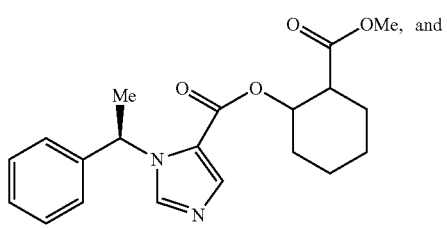
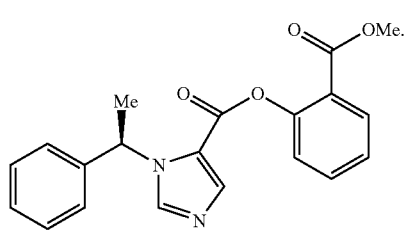
Other compounds specifically contemplated include:
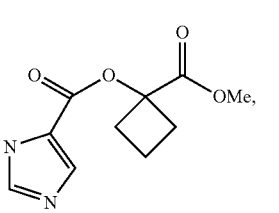
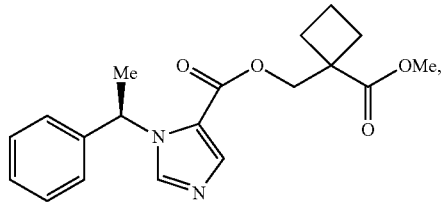
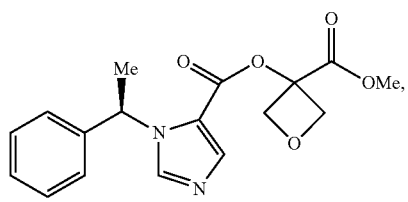
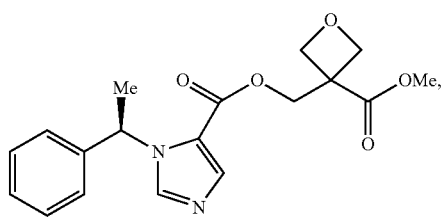
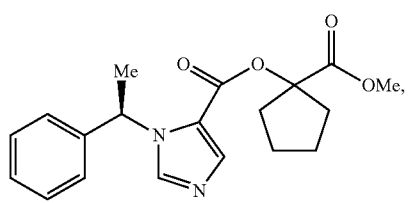
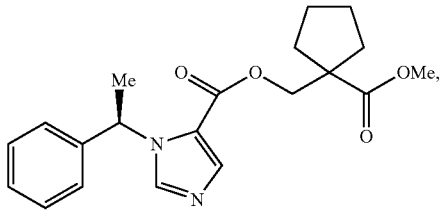
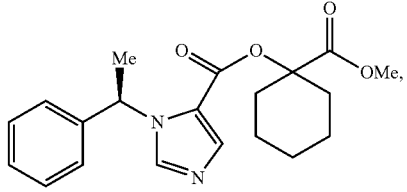
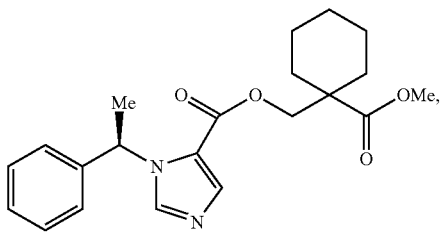
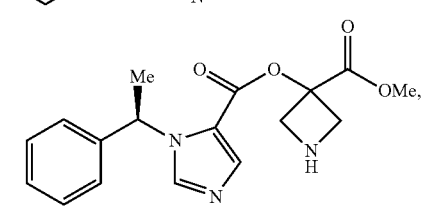
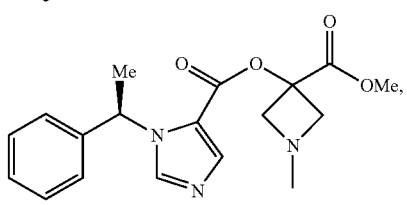
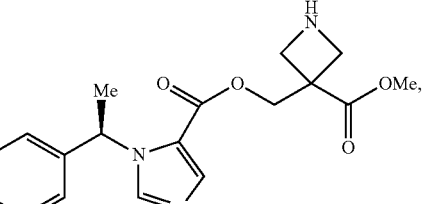
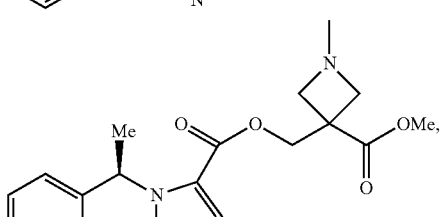
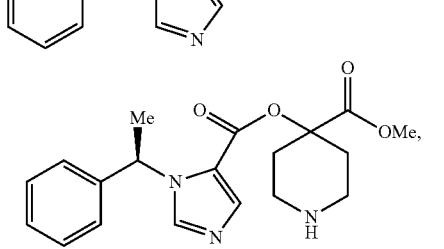

-continued
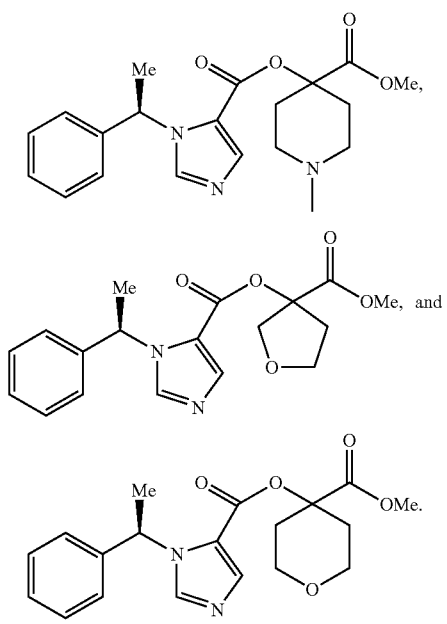
Still other compounds contemplated include:
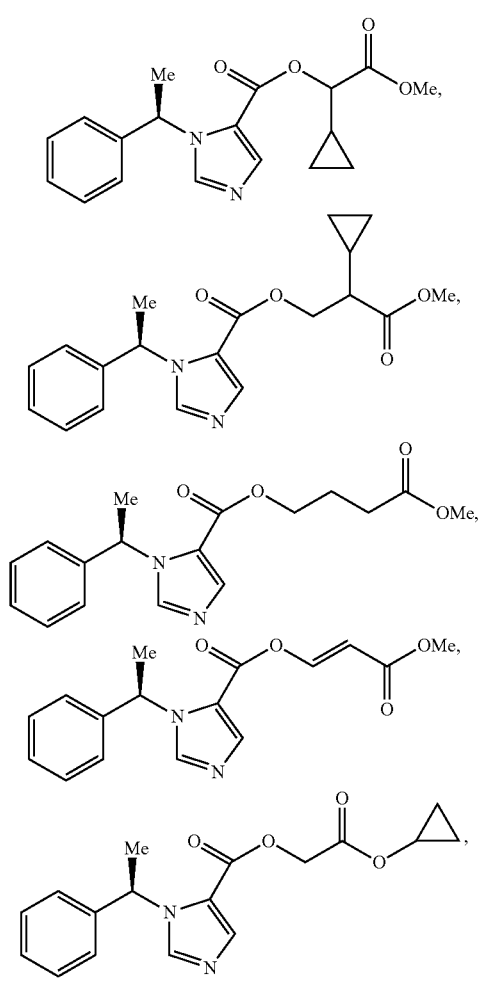
-continued
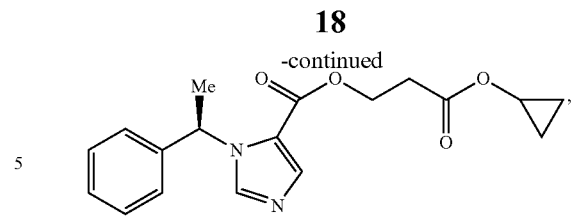
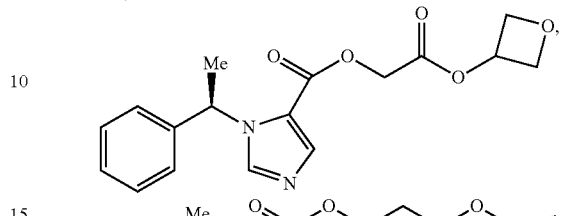
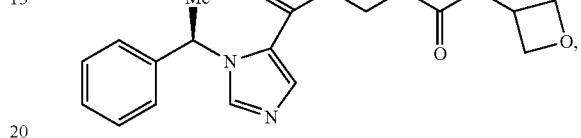
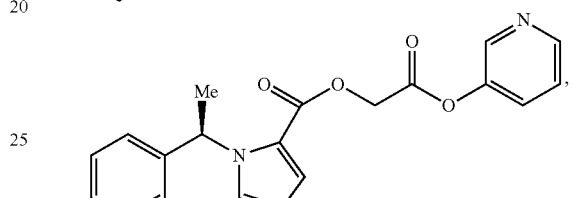
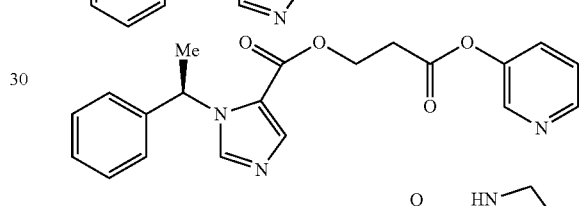
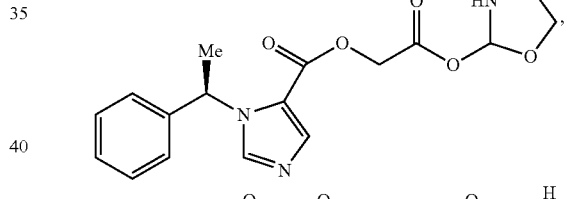
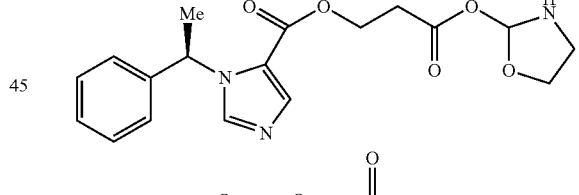
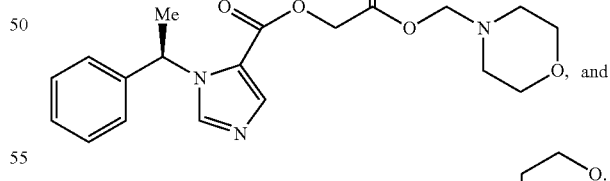
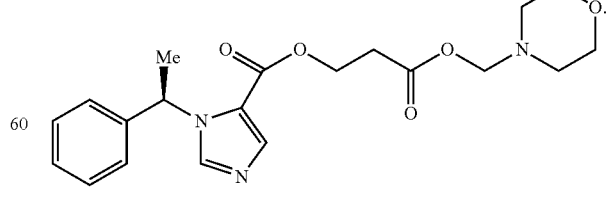
Etomidate analogues with ester moieties on carboetomidate (etomidate with the basic nitrogen in the imidazole ring replaced by $CR^6$) that are sterically unhindered and/or electronically isolated from the pi electron systems in the imidazole and phenyl rings are also preferred.

Compounds of formula (I) can be analogues of etomidate that retain (R)-etomidate's beneficial anesthetic properties, but do not cause clinically significant inhibition of adrenocortical function. For example, the disclosed analogues inhibit adrenocortical function less than 95%, 90%, 85%, 80%, 75%, 70%, 75%, 70%, 65%, 60%, 55%, 50%, 45%, 40%, 35%, 30%, 25%, 20%, 15%, or 10% relative to inhibition of adrenocortical function by a similar amount of etomidate or an etomidate analogue or derivative described in PCT Publication No. WO 2011/005969 and US Patent Application Publication No. 2011/0053998. In another example, the disclosed analogues inhibit adrenocortical function in an amount that is from about 10% to 90%, 15% to 85%, 20% to 80%, 25% to 75%, 30% to 70%, 35% to 65%, 40% to 60%, 45% to 55% to the inhibition of adrenocortical function by a similar amount of etomidate or an etomidate analogue or derivative described in PCT Publication No. WO 2011/005969 and US Patent Application Publication No. 2011/0053998.

Further, unexpectedly, compounds of formula (I) can have improved enhanced duration of action as compared to etomidate analogues and derivatives described in PCT Publication No. WO 2011/005969 and US Patent Application Publication No. 2011/0053998. For example, the disclosed analogues can Etomidate analogues shown in PCT Publication No. WO 2011/005969 and US Patent Application Publication No. 2011/0053998 have ester moieties that are believed to be highly susceptible to hydrolysis by esterases. See U.S. Pat. No. 3,354,173; U.S. Pat. No. 5,466,700; U.S. Pat. No. 5,019,583; and U.S. Patent Publication No. US 2003/0055023. Accordingly, they act like other ultra-short acting drugs like remifentanil and esmolol, and have very short duration of action.

The term "duration of action" refers herein to the length of time an anesthetic exhibits a desired pharmacologic effect after administration. This is determined by the amount of time drug concentration is at or above the minimum effective concentration. The duration of drug in the body is not equivalent to the duration of effect. A drug can be in the body for a period of time that is much longer than the duration of action, if the concentration remains below the minimum effective concentration. In fact, some drugs that are slowly absorbed may never exert a pharmacologic effect, even though they are in the body for a prolonged period of time. This occurs when the drug is absorbed so slowly that it never reaches concentrations that meet or exceed the minimum effective concentration.

By "improved duration of action" is meant duration of action that lasts for a longer period of time relative to a control or reference. For example, the disclosed analogues can have a duration of action that is 5 minutes, 10 minutes, 15 minutes, 20 minutes, 25 minutes, 30 minutes, 35 minutes, 40 minutes, 45 minutes, 50 minutes, 55 minutes, 1 hour, 2 hours, 3 hours, 4 hours, 5 hours, 6 hours or longer than a control or reference. A control or reference can be duration of action of etomidate or etomidate analogues and derivatives described in PCT Publication No. WO 2011/005969 and US Patent Application Publication No. 2011/0053998. In another example, the disclosed analogues can have duration of action that lasts for a period of 10 minutes, 15 minutes, 20 minutes, 25 minutes, 30 minutes, 35 minutes, 40 minutes, 45 minutes, 50 minutes, 55 minutes, 1 hour, 2 hours, 3 hours, 4 hours, 5 hours, 6 hours, 12 hours, 18 hours, 24 hours or longer.

By "short duration of action" is meant duration of action that lasts for a shorter period of time. For example, the disclosed analogues can have a duration of action of 10 seconds, 15 seconds, 20 seconds, 25 seconds, 30 seconds, 35 seconds, 40 seconds, 45 seconds, 50 seconds, 55 seconds, 1 minute, 2 minutes, 5 minutes, 10 minutes, 15 minutes, 20 minutes, 25 minutes, 20 minutes, 35 minutes, 30 minutes, 45 minutes, 40 minutes, 55 minutes, 1 hour, 2 hours, 4 hours, 5 hours, 6 hours or less.

Additionally, the sedative/anesthetic effects of compounds described herein can wear off quickly. The term "wear off" in relation to sedative/anesthetic effect means that the administered compound no longer exhibits a pharmacologic effect on the subject. For example, the disclosed compounds show little or no pharmacologic effects after 30 seconds, 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes, 1 hour, 2 hours, 3 hours, 4 hours, 5 hours, 6 hours, 12 hours or 24 hours after discontinuing anesthetic administration.

Accordingly, a subject can be continually infused to keep the subject sedated during medical procedure, e.g. surgery. However, the subject can wake up quickly once the infusion is stopped. For example, the subject can wake up within about 2 hours, 1.5 hours, 1 hour, 45 minutes, 30 minutes, 20 minutes, 15 minutes, 10 minutes, or 5 minutes after discontinuing anesthetic administration.

The $R^2$, T, $L^1$, and $L^2$ substituents can each independently be substituted with one or more electron donating groups. In embodiments, the electron donating group can be an alkyl or 1-alkenyl. Other electron donating groups such as hydroxyl, amino, NHC(O)R, OC(O)R and aryls and heteroaryls can also be used. The presence of electron donating groups serves to decrease the partial positive charge on the ester carbonyl atom, thereby decreasing susceptibility to nucleophilic attack by esterases and reducing rate of hydrolysis by esterases. Inventors have discovered that etomidate analogues with rapidly hydrolyzed esters have short duration of action. However, by decreasing the rate of ester hydrolysis, duration of action can be increased.

A compound according to the description herein can be characterized by anesthetic activity and enhanced $GABA_A$ receptor activity. The $GABA_A$ receptor is an ionotropic receptor and ligand-gated ion channel. Its endogenous ligand is γ-aminobutyric acid (GABA), the major inhibitory neurotransmitter in the central nervous system. Upon activation, the GABAA receptor selectively conducts Cl— through its pore, resulting in hyperpolarization of the neuron. This causes an inhibitory effect on neurotransmission by diminishing the chance of a successful action potential occurring. In some embodiments, the disclosed analogues can increase $GABA_A$ receptor activity by at least 1.1×, 1.5×, 2×, 2.5×, 3×, 3.5×, 4×, 4.5×, 5×, 5.5×, 10×, 15×, 20× or longer than that of etomidate or an etomidate analogue or derivative described in PCT Pub. No. WO 2011/005969 and US Pat. App. Pub. No. 2011/0053998.

A compound according to the description herein can be characterized by potent in vitro and in vivo anesthetic activity and enhanced $GABA_A$ receptor effects. A compound according to the description herein can be characterized by being a $GABA_A$ receptor agonist. A compound according to the description herein can be characterized by reduced inhibitory activity with respect to in vitro and in vivo adrenocortical steroid synthesis and/or good duration of anesthetic action. In addition, a compound according to the description herein can have a longer duration of anesthetic action than those described, for example, in PCT Pub. No. WO 2011/005969 and US Pat. App. Pub. No. 2011/0053998.

The term "duration of anesthesia" or "duration of anesthetic action" means the period of time during which the administered compound exhibits a pharmacologic effect on the subject or the period of time during which the compound measurably blocks nerve conduction. Without limitation, the disclosed analogues can have a duration of anesthetic action for a period of 30 minutes, 1 hour, 2 hours, 4 hours, 4 hours, 5 hours, 6 hours, 12 hours, 18 hours, 24 hours or longer. In some embodiments, the disclosed analogues can have a duration of anesthetic action that is at least 1.1×, 1.5×, 2×, 2.5×, 3×, 3.5×, 4×, 4.5×, 5×, 5.5×, 10×, 15×, 20× or longer than that of etomidate or an etomidate analogue or derivative described in PCT Pub. No. WO 2011/005969 and US Pat. App. Pub. No. 2011/0053998.

The new compounds described herein can be administered either alone in the form of mixtures with one another, or in combination with acceptable pharmaceutical carriers. Thus, pharmaceutical compositions which can comprise an effective amount of at least one compound of the description, with or without a pharmaceutically or physiologically acceptable carrier, are also contemplated. If appropriate, the compound can be administered in the form of a physiologically acceptable salt, for example, an acid-addition salt.

Described herein also is a method of treating animals or humans. This method comprises administering to the animal or person an effective amount of at least one of the compounds described herein, or a pharmaceutically acceptable salt or solvate thereof, with, or without a pharmaceutically acceptable carrier. Intravenous administration of etomidate is well known and described, for example in U.S. Pat. No. 4,289,783, the content of which is incorporated herein by reference in its entirety. Such intravenous methods of administration are applicable to the compounds described herein.

Disclosed here is a potent sedative hypnotic that does not significantly suppress adrenocortical function and can be used to produce and/or maintain anesthesia, sedation, or otherwise lower central nervous system excitability. It can exhibit one or more of the following beneficial properties as compared to alternative agents: higher potency, longer duration of therapeutic action, shorter duration of side effects, reduced adrenocortical suppression, higher therapeutic index, lower toxicity, reduced cardiovascular depression, and greater ease of titration to desired effect.

In some embodiments, the disclosed analogues have a potency that is at least 1.1×, 1.2×, 1.3×, 1.4×, 1.5×, 2×, 2.5×, 3×, 3.5×, 4×, 4.5×, 5×, 10× 15×, 20×, 25×, 30×, 50× or higher than the potency of a similar amount of etomidate or an etomidate analogue or derivative described in PCT Pub. No. WO 2011/005969 and US Pat. App. Pub. No. 2011/0053998. In some embodiments, the disclosed analogues have a duration of therapeutic action that is at least 1.1×, 1.2×, 1.3×, 1.4×, 1.5×, 2×, 2.5×, 3×, 3.5×, 4×, 4.5×, 5×, 10× 15×, 20×, 25×, 30×, 50× or longer than duration of therapeutic action of a similar amount of etomidate or an etomidate analogue or derivative described in PCT Pub. No. WO 2011/005969 and US Pat. App. Pub. No. 2011/0053998. In some embodiments, the disclosed analogues have a therapeutic index that is at least 1.1×, 1.2×, 1.3×, 1.4×, 1.5×, 2×, 2.5×, 3×, 3.5×, 4×, 4.5×, 5×, 10× 15×, 20×, 25×, 30×, 50× or higher than the therapeutic index of etomidate or an etomidate analogue or derivative described in PCT Pub. No. WO 2011/005969 and US Pat. App. Pub. No. 2011/0053998. In some embodiments, the disclosed analogues have a shorter duration of side effects relative to etomidate or an etomidate analogue or derivative described in PCT Pub. No. WO 2011/005969 and US Pat. App. Pub. No. 2011/0053998. For example, the duration of side effects of the disclosed analogues can be period of time which is at least 1 minute, 5 minutes, 10 minutes, 15 minutes, 20 minutes, 35 minutes, 30 minutes, 35 minutes, 10 minutes, 45 minutes, 50 minutes, 55 minutes, 1 hour, 2 hours, 3 hours, 4 hours, 5 hours, 6 hour, 12 hours, 18 hours, 24 hours shorter than the duration of side effects by a similar amount of etomidate or an etomidate analogue or derivative described in PCT Pub. No. WO 2011/005969 and US Pat. App. Pub. No. 2011/0053998. In some embodiments, the disclosed analogues inhibit adrenocortical function less than 95%, 90%, 85%, 80%, 75%, 70%, 75%, 70%, 65%, 60%, 55%, 50%, 45%, 40%, 35%, 30%, 25%, 20%, 15%, or 10% relative to inhibition of adrenocortical function by a similar amount of etomidate or an etomidate analogue or derivative described in PCT Publication No. WO 2011/005969 and US Patent Application Publication No. 2011/0053998. In some embodiments, the disclosed analogues have cardiovascular depression that is less than 95%, 90%, 85%, 80%, 75%, 70%, 75%, 70%, 65%, 60%, 55%, 50%, 45%, 40%, 35%, 30%, 25%, 20%, 15%, or 10% relative to the cardiovascular depression by a similar amount of etomidate or an etomidate analogue or derivative described in PCT Publication No. WO 2011/005969 and US Patent Application Publication No. 2011/0053998. In some embodiments, the disclosed analogues have toxicity that is less than 95%, 90%, 85%, 80%, 75%, 70%, 75%, 70%, 65%, 60%, 55%, 50%, 45%, 40%, 35%, 30%, 25%, 20%, 15%, or 10% relative to the toxicity of a similar amount of etomidate or an etomidate analogue or derivative described in PCT Publication No. WO 2011/005969 and US Patent Application Publication No. 2011/0053998

The compounds described herein can be administered as a single IV bolus and/or a continuous IV infusion. Other routes of delivery can include oral, rectal, transmucosal, subcutaneous, or inhaled, for example.

Pharmaceutical Compositions

For administration to a subject, the compounds described herein can be provided in pharmaceutically acceptable (e.g., sterile) compositions. Accordingly, another aspect described herein is a pharmaceutical composition comprising a compound according to formula (I) and a pharmaceutically acceptable carrier. These pharmaceutically acceptable compositions comprise an effective amount of one or more of the compounds described herein, formulated together with one or more pharmaceutically acceptable carriers (additives) and/or diluents. As described in detail below, the pharmaceutical compositions of the present disclosure can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and/or systemic absorption), boluses, powders, granules, pastes for application to the tongue; (2) parenteral administration, for example, by subcutaneous, intramuscular, intravenous (e.g., bolus or infusion) or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960, content of all of which is herein incorporated by reference.

Formulations can optionally further comprise one or more cyclodextrins. In various cases, cyclodextrins are α-cyclodextrins, β-cyclodextrins, γ-cyclodextrins, and/or δ-cyclodextrins. In some embodiments, the cyclodextrins are modified cyclodextrins. Specific modifications include, but are not limited to, hydroxyalkyl ethers and sulfoalkyl ethers. In some embodiments, the modified cyclodextrins are sulfobutylether-1-β-cyclodextrin, sulfobutylether-4-β-cyclodextrin, sulfobutylether-7-β-cyclodextrin, and/or hydroxypropylether β-cyclodextrin. In one embodiment, the modified cyclodextrin comprises sulfobutylether-7-β-cyclodextrin.

As used herein, the term "pharmaceutically acceptable" or "pharmacologically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Moreover, for animal (e.g., human) administration, it will be understood that compositions should meet sterility, pyrogenicity, general safety and purity standards as required by FDA Office of Biological Standards.

As used herein, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, disintegrating agents, binders, sweetening agents, flavoring agents, perfuming agents, protease inhibitors, plasticizers, emulsifiers, stabilizing agents, viscosity increasing agents, film forming agents, solubilizing agents, surfactants, preservative and antioxidants can also be present in the formulation. The terms such as "excipient", "carrier", "pharmaceutically acceptable carrier" or the like are used interchangeably herein.

For liquid formulations, pharmaceutically acceptable carriers can be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions, or suspensions, including saline and buffered media. Examples of oils are those of petroleum, animal, vegetable, or synthetic origin, for example, peanut oil, soybean oil, mineral oil, olive oil, sunflower oil, and fish-liver oil. Solutions or suspensions can also include one or more of the following components: a sterile diluent, including water for injection, saline solution, fixed oils, polyethylene glycols, glycerine, propylene glycol and other synthetic solvents; antibacterial agents, including benzyl alcohol and methyl parabens; anti-oxidants, including ascorbic acid or sodium bisulfite; chelating agents, including ethylenediaminetetraacetic acid (EDTA); buffers, including acetates, citrates and phosphates, and agents for the adjustment of tonicity, including sodium chloride and dextrose. The pH can be adjusted with acids or bases, including hydrochloric acid and sodium hydroxide.

Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

As indicated above, the compositions can further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

In some embodiments, the compounds of the present disclosure can be used in the form of a pharmaceutically acceptable salt. As used herein, the term "pharmaceutically-acceptable salts" refers to the conventional nontoxic salts or quaternary ammonium salts of compounds described herein, e.g., from non-toxic organic or inorganic acids. These salts can be prepared in situ in the administration vehicle or the dosage form manufacturing process, or by separately reacting a compound described herein in its free base or acid form with a suitable organic or inorganic acid or base, and isolating the salt thus formed during subsequent purification. Conventional nontoxic salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., "Pharmaceutical Salts", *J. Pharm. Sci.* 66:1-19 (1977), the content of which is herein incorporated by reference in its entirety. Exemplary salts also include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like.

Suitable acids which are capable of forming salts with the compounds of the disclosure include inorganic acids such as hydrochloric acid, hydrobromic acid, perchloric acid, nitric acid, thiocyanic acid, sulfuric acid, phosphoric acid, and the like; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid, trifluoroacetic acid, methansulfonic acid, benzenesulfonic acid, p-toluenesulfonic acid, and the like. Suitable bases capable of forming salts with the compounds of the disclosure include inorganic bases such as sodium hydroxide, ammonium hydroxide, potassium hydroxide and the like; and organic bases such as mono-, di- and tri-alkyl and aryl amines (e.g., triethylamine, diisopropyl amine, methyl amine, dimethyl amine, pyridine, picoline, dicyclohexylamine, N,N'-dibenzylethylenediamine, and the like) and optionally substituted ethanol-amines (e.g., ethanolamine, diethanolamine, triethanolamine and the like).

It is especially advantageous to formulate oral and intravenous compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals. The pharmaceutical compositions can be included in a container, pack, or dispenser together with instructions for administration.

The amount of a compound described herein that can be combined with a carrier material to produce a single dosage form will generally be an effective amount of the compound. A pharmaceutical composition typically contains an amount of at least 0.01 weight % of active ingredient, i.e., a compound of this disclosure, per weight of total pharmaceutical composition. Generally out of one hundred percent, this amount will range from about 0.01% to 99% of the compound, preferably from about 5% to about 70%, most preferably from 10% to about 30%. A weight % is a ratio by weight of active ingredient to total composition. Thus, for example, 0.1 weight % is 0.1 grams of the compound per 100 grams of total composition.

The preparation of pharmaceutical compositions that contain an active component is well understood in the art, for example, by mixing, granulating, or tablet-forming processes. The active therapeutic ingredient is often mixed with excipients that are pharmaceutically acceptable and compatible with the active ingredient. For oral administration, the active agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic, or oily solutions and the like as detailed above.

For intravenous administration, glucuronic acid, L-lactic acid, acetic acid, citric acid or any pharmaceutically acceptable acid/conjugate base with reasonable buffering capacity in the pH range acceptable for intravenous administration can be used as buffers. Sodium chloride solution wherein the pH has been adjusted to the desired range with either acid or base, for example, hydrochloric acid or sodium hydroxide, can also be employed. Typically, a pH range for the intravenous formulation can be in the range of from about 5 to about 12.

Subcutaneous formulations can be prepared according to procedures well known in the art at a pH in the range between about 5 and about 12, which include suitable buffers and isotonicity agents. They can be formulated to deliver a daily dose of the active agent in one or more daily subcutaneous administrations. The choice of appropriate buffer and pH of a formulation, depending on solubility of one or more compounds to be administered, is readily made by a person having ordinary skill in the art. Sodium chloride solution wherein the pH has been adjusted to the desired range with either acid or base, for example, hydrochloric acid or sodium hydroxide, can also be employed in the subcutaneous formulation. Typically, a pH range for the subcutaneous formulation can be in the range of from about 5 to about 12.

Described herein are also a method for providing anesthesia in a subject comprising administering to the subject a compound of formula (I) or a pharmaceutical composition as described herein, and use of a compound of formula (I) or a pharmaceutical composition as described herein providing anesthesia in a subject or in manufacture of a medicament for providing anesthesia in a subject. Also contemplated is use of a compound of formula (I) as a potentiator of $GABA_A$ receptor/channel activation. Accordingly, in certain embodiments, the method includes administering an effective dose of the compound. As used herein, the term "effective dose" or "effective amount" is meant that amount sufficient to elicit the desired pharmacological effects at a reasonable benefit/risk ratio applicable to any medical treatment.

Described herein are also a method for providing anesthesia in a subject comprising administering to the subject a compound of formula (I) or a pharmaceutical composition as described herein, and use of a compound of formula (I) or a pharmaceutical composition as described herein to alleviate pain in, or provide an analgesic to, a subject or in the manufacture of a medicament for alleviating pain or providing an analgesic to a subject. Accordingly, in certain embodiments, the method includes use or administration of an effective dose of the compound. As used herein, the term "effective dose" or "effective amount" is meant that amount sufficient to elicit the desired pharmacological effects at a reasonable benefit/risk ratio applicable to any medical treatment.

Determination of an effective amount is well within the capability of those skilled in the art. Generally, the actual effective amount can vary with the specific compound, the use or application technique, the desired effect, the duration of the effect and side effects, the subject's history, age, condition, sex, as well as the severity and type of the medical condition in the subject, and administration of other pharmaceutically active agents. Accordingly, an effective dose of compound described herein is an amount sufficient to induce and maintain general anesthesia or conscious sedation in a subject.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of use or administration utilized.

The effective dose can be estimated initially from cell culture assays. A dose may be formulated in animal models to achieve a circulating plasma concentration range that includes the IC50 (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay. The effective plasma concentration for inducing anesthesia using a compound as disclosed herein can be about 0.01 µM to about 10 µM, about 0.2 µM to about 5 µM, or about 0.8 to about 3 µM in a subject, such as a rat, dog, or human.

Generally, the compositions are administered so that a compound of the disclosure herein is used or given at a dose from 1 µg/kg to 1000 mg/kg; 1 µg/kg to 500 mg/kg; 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. Further contemplated is a dose (either as a bolus or continuous infusion) of about 0.1 mg/kg to about 10 mg/kg, about 0.3 mg/kg to about 5 mg/kg, or 0.5 mg/kg to about 3 mg/kg. It is to be further understood that the ranges intermediate to those given above are also within the scope of this disclosure, for example, in the range 1 mg/kg to 10 mg/kg, for example use or dose ranges such as 2 mg/kg to 8 mg/kg, 3 mg/kg to 7 mg/kg, 4 mg/kg to 6 mg/kg, and the like.

The compound can be administered as a single bolus or multiple boluses, as a continuous infusion, or a combination thereof. For example, the compound can be administered as a single bolus initially, and then administered as a continuous infusion following the bolus. The rate of the infusion can be any rate sufficient to affect anesthesia or sedation. Some contemplated infusion rates include from 1 µg/kg/min to 100 mg/kg/min, or from 1 µg/kg/hr to 1000 mg/kg/hr. Rates of infusion can include 0.2 to 1.5 mg/kg/min, or more specifically 0.25 to 1 mg/kg/min, or even more specifically 0.25 to 0.5 mg/kg/min. It will be appreciated that the rate of infusion can be determined based upon the dose necessary to induce sedation or anesthesia and the rate of elimination of the compound, such that the compound is administered via infusion at a rate sufficient to safely maintain a sufficient amount of compound in the bloodstream to affect anesthesia or sedation In some embodiments, the compositions are used or administered at a dosage so that a compound of formula (I) or a metabolite thereof (e.g., wherein the ester has been hydrolyzed) is rapidly cleared, e.g. such that it has an in vivo concentration of less than 500 nM, less than 400 nM, less than 300 nM, less than 250 nM, less than 200 nM, less than 150 nM, less than 100 nM, less than 50 nM, less than 25 nM, less than 20 nM, less than 10 nM, less than 5 nM, less than 1 nM, less than 0.5 nM, less than 0.1 nM, less than 0.05 nM, less than 0.01 nM, less than 0.005 nM, or less than 0.001 nM at and after a specific time following use or administration, such as 15 min, 30 min, 1 hr, 1.5 hrs, 2 hrs, 2.5 hrs, 3 hrs, 4 hrs, 5 hrs, 6 hrs, 7 hrs, 8 hrs, 9 hrs, 10 hrs, 11 hrs, 12 hrs or more of time after use or administration of the composition. In some cases, the specific time is less than 15 min, less than 10 min, or within 3-10 min after use or administration.

In some embodiments, a compound of formula I is used or administered at a dosage so that it has an in vivo concentration of less than 500 nM at 30 minutes after use or administration. In various embodiments, a compound of formula I is used or administered at a dosage so that its inactive metabolite has an in vivo concentration of less than 500 nM at 1 hr after use or administration. In some cases, the concentration is less than 100 nM and is achieved in 10 min or less after administration or use of the compound as disclosed herein. In some cases, the compound as disclosed herein has an in vivo concentration of less than 10 nM at less than 2 hours after use or administration, e.g., within 1-2 hours after administration.

The terms "administration of" and or "administering" a compound should be understood to mean providing a compound or a composition described herein to a subject in need of inducing anesthesia. As such, the term "administer" refers to the placement of a compound or composition described herein into a subject by a method or route which results in at least partial localization of the compound or composition at a desired site such that general anesthesia or conscious sedation is induced and/or maintained in the subject.

The compounds described herein can be administered by any appropriate route known in the art including, but not limited to oral or parenteral routes, including intravenous, intramuscular, subcutaneous, transdermal, airway (aerosol), pulmonary, nasal, rectal, and topical (including buccal and sublingual) administration.

In addition to those described above, exemplary modes of use and administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, the compositions are administered by intravenous infusion or injection.

In some embodiments, the method includes use or administration of an injection of a single effective dose of the compound which may or may not be followed by a continuous infusion of the compound.

In some embodiments, the method includes use or administration of a continuous infusion of an effective dose of the compound of formula (I) or a pharmaceutically composition comprising a compound of formula (I).

The compounds described herein can be used or administrated to a subject in combination with another pharmaceutically active agent or treatment modality for a particular indication. Exemplary pharmaceutically active compound include, but are not limited to, those found in *Harrison's Principles of Internal Medicine*, 13th Edition, Eds. T. R. Harrison et al. McGraw-Hill N.Y., N.Y.; Physicians' Desk Reference, 50th Edition, 1997, Oradell N.J., Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete contents of all of which are incorporated herein by reference.

Accordingly, in certain embodiments, the method also includes use or administration to the subject an effective amount of a therapeutic agent selected from another sedative hypnotic agent, an analgesic agent, and a paralytic agent. Non-limiting examples of sedative hypnotic agents include benzodiazepines, barbiturates, ketamine, propofol, isoflurane, and desflurane. Non-limiting examples of analgesic agents include non-steroidal anti-inflammatory drugs (NSAIDs), paracetamol/acetaminophen, COX-2 inhibitors, and opioids. Non-limiting examples of paralytic agents include rapacuronium, mivacurium, succinylcholine, vecuronium, and cisatracurium.

In some embodiments, a compound described herein is the only sedative hypnotic agent administered.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein. The terms, "patient" and "subject" are used interchangeably herein. A subject can be male or female.

Preferably, the subject is a mammal. The mammal can be a human, non-human primate, mouse, rat, dog, cat, horse, or cow, but are not limited to these examples. Mammals other than humans can be advantageously used as subjects that represent animal models of human diseases and disorders. In addition, compounds, compositions and methods described herein can be used to treat domesticated animals and/or pets.

The compounds according to the disclosure can be prepared by synthetic processes which are known to those skilled in the art, particularly in view of the state of the art and the specific preparatory examples provided below herein. Suitable modification to starting materials by methods well known in the art may also be employed.

Synthesis of Compounds of Formula (I)

Further disclosed herein are methods of synthesizing a compound of formula (I). More specifically, provided herein is a method comprising hydrolyzing ethyl-1-(1-phenyl-ethyl)-1H-imidazole-5-carboxylate to obtain 1-(1-phenyl-ethyl)-1H-imidazole-5-carboxylic acid; and reacting the carboxylic acid with an alcohol of structure HOL²-[C(R⁷R⁸)]$_p$—C(R⁹R¹⁰)—C(O)OT.

Provided herein is yet another method of synthesizing a compound of formula (I). The method comprises coupling a compound of formula (II) and (a) a compound of formula (III) or (b) a compound of formula (IV):

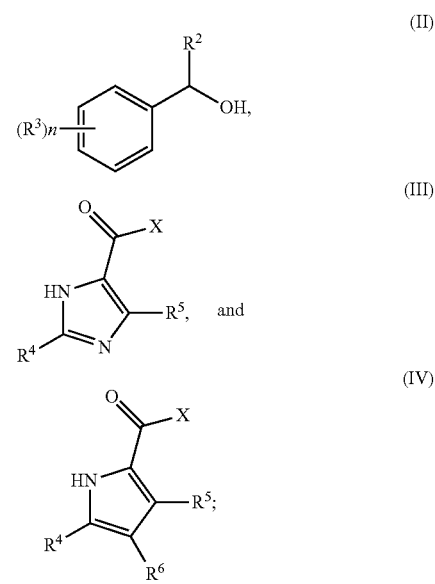

wherein X is a carboxylic acid protecting group; removing X to form a carboxylic acid; coupling the carboxylic acid with an alcohol of structure HOL²-[C(R⁷R⁸)]$_p$—C(R⁹R¹⁰)—C(O)OT, wherein L², R⁷, R⁸, R⁹, R¹⁰, T and p are as defined for formula (I).

Protecting group X can be any protecting group known, including those described in *Greene's Protective Groups in Organic Synthesis*. Some specific examples include O-alkyl and S-alkyl.

Specifically, synthesis of a compound of formula (I), when Z is N, comprises coupling a phenyl of formula (II):

FORMULA (II)

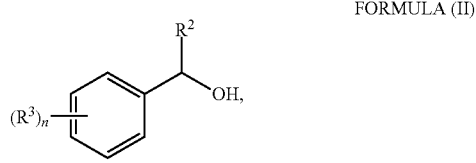

with an imidazole of formula (III):

FORMULA (III)

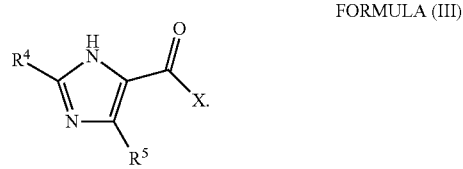

wherein $R^2$, $R^3$, $R^4$, $R^5$ and n are as defined above for formula (I) and X is a protecting group; removing the protecting group on the carboxylic; and reacting the resulting carboxylic acid an alcohol having the structure HO-$L^2$-[C($R^7R^8$)]$_p$—C($R^9R^{10}$)—C(O)OT, wherein $L^2$, $R^7$, $R^8$, $R^9$, $R^{10}$, T and p are as defined above for formula (I).

Synthesis of a compound of formula (I), when n is 0 and Z is N, comprises hydrolyzing the ester ethyl group from R- or S-etomidate and reacting the resulting carboxylic acid then reacted with the desired alcohol.

Synthesis of a compound of formula (I), when Z is $CR^6$, comprises can be coupling a phenyl of formula (II) described above with a pyrrole of formula (IV):

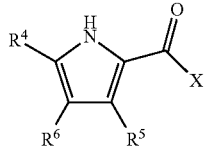

FORMULA (IV)

wherein $R^4$, $R^5$, and $R^6$ are as defined above for formula (I) and X is carboxylic acid protecting group; removing the protecting group on the carboxylic; and reacting the resulting carboxylic acid reacted with an alcohol having the structure HO-$L^2$-[C($R^7R^8$)]$_p$—C($R^9R^{10}$)—C(O)OT, wherein $L^2$, $R^7$, $R^8$, $R^9$, $R^{10}$, T and p are as defined above for formula (I).

The reaction between phenyl of formula (II) and imidazole of formula (III) or pyrrole of formula (IV) proceeds with inversion of configuration. Thus, using a phenyl of appropriate configuration, the compound of formula (I) with the correct configuration at the carbon to which the $R^2$ substituent is attached can be obtained. For example, using a phenyl with the S configuration leads to a compound of formula (I) having the R configuration. The phenyls of formula (II) are easily prepared by reduction of phenyl alkyl ketones and derivatives thereof.

Some Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

The singular terms "a," "an," and "the" include plural referents unless context clearly indicates otherwise. Similarly, the word "or" is intended to include "and" unless the context clearly indicates otherwise.

Although methods and materials similar or equivalent to those described herein can be used in the practice or testing of this disclosure, suitable methods and materials are described below. The term "comprises" means "includes."

The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means at least two standard deviations (2SD) away from a reference level. The term refers to statistical evidence that there is a difference. It is defined as the probability of making a decision to reject the null hypothesis when the null hypothesis is actually true.

As used herein, the term "alkyl" refers to saturated straight-chain, branched-chain or cyclic hydrocarbon radicals. Examples of alkyl radicals include, but are not limited to, methyl, ethyl, propyl, isopropyl, cyclopropyl-, n-butyl, tert-butyl, neopentyl, n-hexyl, cyclohexyl, n-octyl, n-decyl, n-dodecyl and n-hexadecyl radicals. Backbone of the alkyl can be optionally inserted with one or more heteroatoms, such as N, O, or S. The term "alkylene" refers to divalent alkyl.

As used herein, the term "alkenyl" refers to unsaturated straight-chain, branched-chain or cyclic hydrocarbon radicals having at least one carbon-carbon double bond. Examples of alkenyl radicals include, but are not limited to, allyl, butenyl, hexenyl and cyclohexenyl radicals. Backbone of the alkenyl can be optionally inserted with one or more heteroatoms, such as N, O, or S. The term "alkenylene" refers to divalent alkenyl.

As used herein, the term "alkynyl" refers to unsaturated hydrocarbon radicals having at least one carbon-carbon triple bond. Representative alkynyl groups include, but are not limited to, ethynyl, 1-propynyl, 1-butynyl, isopentynyl, 1,3-hexa-diyn-yl, n-hexynyl, 3-pentynyl, 1-hexen-3-ynyl and the like. Backbone of the alkynyl can be optionally inserted with one or more heteroatoms, such as N, O, or S. The term "alkynylene" refers to divalent alkynyl.

As used herein, the term "halogen" refers to an atom selected from fluorine, chlorine, bromine and iodine. The term "halogen radioisotope" refers to a radionuclide of an atom selected from fluorine, chlorine, bromine and iodine.

The term "aryl" refers to monocyclic, bicyclic, or tricyclic aromatic ring system wherein 0, 1, 2, 3, or 4 atoms of each ring may be substituted by a substituent. Exemplary aryl groups include, but are not limited to, benzyl, phenyl, naphthyl, anthracenyl, azulenyl, fluorenyl, indanyl, indenyl, naphthyl, phenyl, tetrahydronaphthyl, and the like.

The term "cyclyl" or "cycloalkyl" refers to saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Exemplary cycloalkyl groups include, but are not limited to, cyclopropyl, cyclobutyl, cyclopentyl, cyclopentenyl, cyclohexyl, cyclohexenyl, cycloheptyl, cyclooctyl, and the like.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Exemplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, and the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Exemplary heterocyclyl groups include, but are not limited to piperazinyl, pyrrolidinyl, dioxanyl, morpholinyl, tetrahydrofuranyl, and the like.

As used herein, the term "substituted" refers to independent replacement of one or more (typically 1-4) of the hydrogen atoms on the substituted moiety with substituents independently selected from the group of substituents listed below in the definition for "substituents" or otherwise specified. Suitable substituents include, without limitation, acyl, acylamino, acyloxy, alkanesulfonamido, alkanesulfonyl, alkaryl, alkenyl, alkoxy, alkoxycarbonyl, alkyl, alkylamino, alkylcarbanoyl, alkynyl, amido, amino, aminoalkyl, aralkyl, aralkylsulfonamido, arenesulfonamido, arenesulfonyl, aryl, arylamino, arylcarbanoyl, aryloxy, carbonyl, carboxy, cyano, haloalkyl, halogen, heteroaryl, heterocycloalkyl, hydroxy, hydroxyalkyl, mercapto, nitro, oxo, and ureido groups. In some cases, two substituents, together with the carbons to which they are attached to can form a ring.

The term "derivative" as used herein refers to a chemical substance related structurally to another, i.e., an "original" substance, which can be referred to as a "parent" compound. A "derivative" can be made from the structurally-related parent compound in one or more steps. In some embodiments, the general physical and chemical properties of a derivative can be similar to or different from the parent compound.

As used herein, the term "PEG" means an ethylene glycol polymer that contains about 20 to about 2000000 linked monomers, typically about 50-1000 linked monomers, usually about 100-300. Polyethylene glycols include PEGs containing various numbers of linked monomers, e.g., PEG20, PEG30, PEG40, PEG60, PEG80, PEG100, PEG115, PEG200, PEG 300, PEG400, PEG500, PEG600, PEG1000, PEG1500, PEG2000, PEG3350, PEG4000, PEG4600, PEG5000, PEG6000, PEG8000, PEG11000, PEG12000, PEG2000000 and any mixtures thereof.

As used here in the term "isomer" refers to compounds having the same molecular formula but differing in structure. Isomers which differ only in configuration and/or conformation are referred to as "stereoisomers." The term "isomer" is also used to refer to an enantiomer.

The term "enantiomer" is used to describe one of a pair of molecular isomers which are mirror images of each other and non-superimposable. Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of pure enantiomers, which is the ability of different pure enantiomers to rotate planepolarized light in different directions). Enantiomers generally have identical physical properties, such as melting points and boiling points, and also have identical spectroscopic properties. Enantiomers can differ from each other with respect to their interaction with plane-polarized light and with respect to biological activity.

The designations "R" and "S" are used to denote the absolute configuration of the molecule about its chiral center(s). The designations may appear as a prefix or as a suffix; they may or may not be separated from the isomer by a hyphen; they may or may not be hyphenated; and they may or may not be surrounded by parentheses.

The designations or prefixes "(+)" and "(−)" are employed to designate the sign of rotation of plane-polarized light by the compound, with (−) meaning that the compound is levorotatory (rotates to the left). A compound prefixed with (+) is dextrorotatory (rotates to the right).

The term "racemic mixture," "racemic compound" or "racemate" refers to a mixture of the two enantiomers of one compound. An ideal racemic mixture is one wherein there is a 50:50 mixture of both enantiomers of a compound such that the optical rotation of the (+) enantiomer cancels out the optical rotation of the (−) enantiomer.

The term "resolving" or "resolution" when used in reference to a racemic mixture refers to the separation of a racemate into its two enantiomorphic forms (i.e., (+) and (−); 65 (R) and (S) forms). The terms can also refer to enantioselective conversion of one isomer of a racemate to a product.

The term "enantiomeric excess" or "ee" refers to a reaction product wherein one enantiomer is produced in excess of the other, and is defined for a mixture of (+)- and (−)-enantiomers, with composition given as the mole or weight or volume fraction F(+) and F(−) (where the sum of F(+) and F(−)=1). The enantiomeric excess is defined as *F(+)−F(−)* and the percent enantiomeric excess by 100× *F(+)−F(−)*. The "purity" of an enantiomer is described by its ee or percent ee value (% ee).

Whether expressed as a "purified enantiomer" or a "pure enantiomer" or a "resolved enantiomer" or "a compound in enantiomeric excess", the terms are meant to indicate that the amount of one enantiomer exceeds the amount of the other. Thus, when referring to an enantiomer preparation, both (or either) of the percent of the major enantiomer (e.g. by mole or by weight or by volume) and (or) the percent enantiomeric excess of the major enantiomer may be used to determine whether the preparation represents a purified enantiomer preparation.

The term "enantiomeric purity" or "enantiomer purity" of an isomer refers to a qualitative or quantitative measure of the purified enantiomer; typically, the measurement is expressed on the basis of ee or enantiomeric excess.

The terms "substantially purified enantiomer," "substantially resolved enantiomer" "substantially purified enantiomer preparation" are meant to indicate a preparation (e.g. derived from non-optically active starting material, substrate, or intermediate) wherein one enantiomer has been enriched over the other, and more preferably, wherein the other enantiomer represents less than 20%, more preferably less than 10%, and more preferably less than 5%, and still more preferably, less than 2% of the enantiomer or enantiomer preparation.

The terms "purified enantiomer," "resolved enantiomer" and "purified enantiomer preparation" are meant to indicate a preparation (e.g. derived from non-optically active starting material, substrates or intermediates) wherein one enantiomer (for example, the R-enantiomer) is enriched over the other, and more preferably, wherein the other enantiomer (for example the S-enantiomer) represents less than 30%, preferably less than 20%, more preferably less than 10% (e.g. in this particular instance, the R-enantiomer is substantially free of the S-enantiomer), and more preferably less than 5% and still more preferably, less than 2% of the preparation. A purified enantiomer may be synthesized substantially free of the other enantiomer, or a purified enantiomer may be synthesized in a stereo-preferred procedure, followed by separation steps, or a purified enantiomer may be derived from a racemic mixture.

The term "enantioselectivity," also called the enantiomeric ratio indicated by the symbol "E," refers to the selective capacity of an enzyme to generate from a racemic substrate one enantiomer relative to the other in a product racemic mixture; in other words, it is a measure of the ability of the enzyme to distinguish between enantiomers. A non-selective reaction has an E of 1, while resolutions with E's above 20 are generally considered useful for synthesis or resolution. The enantioselectivity resides in a difference in conversion rates between the enantiomers in question. Reaction products are obtained that are enriched in one of the enantiomers; conversely, remaining substrates are enriched in the other enantiomer. For practical purposes it is generally desirable for one of the enantiomers to be obtained in large excess. This is achieved by terminating the conversion process at a certain degree of conversion.

The term "RT" refers to room temperature, about 20° C. to 25° C.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

All patents, publications and references cited herein are hereby fully incorporated by reference. In case of conflict between the present disclosure and incorporated patents, publications and references, the present disclosure should control.

Aspect disclosed herein can be illustrated by any of the following numbered paragraphs:

1. A compound according to formula (I)

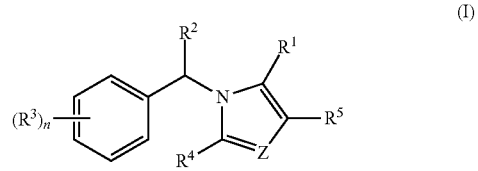

wherein, $R^1$ is $L^1C(O)OL^2$-$[C(R^7R^8)]_p$—$C(R^9R^{10})$—$C(O)OT$;

$R^2$ is $R^1$, optionally substituted linear or branched $C_1$-$C_{10}$ alkyl, optionally substituted linear or branched $C_2$-$C_{10}$ alkenyl, or optionally substituted linear or branched $C_2$-$C_{10}$ alkynyl, wherein the backbone of $C_1$-$C_{10}$ alkyl, $C_2$-$C_{10}$ alkenyl, or $C_2$-$C_{10}$ alkynyl optionally comprises one or more heteroatoms;

each $R_3$ is independently halogen, CN, $CF_3$, $SR^2$, $SOR^2$, $SO_2R^2$, $OR^2$, $CO_2H$, $CO_2R^2$, $N(R^2)_2$, $NHR^2$, $NO_2$, or $R^2$;

Z is N or $CR^6$;

$R^4$, $R^5$, and $R^6$ are independently hydrogen, halogen, CN, $CF_3$, $SR^2$, $SOR^2$, $SO_2R^2$, $OR^2$, $CO_2H$, $CO_2R^2$, $N(R^2)_2$, $NHR^2$, $NO_2$, or $R^2$;

$R^7$ and $R^8$ are independently hydrogen, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, or $R^7$ and $R^8$ together with the carbon they are attached to form an optionally substituted 3-8 membered cyclyl or heterocyclyl;

$R^9$ and $R^{10}$ are independently hydrogen, optionally substituted linear or branched $C_1$-$C_{10}$ alkyl, optionally substituted linear or branched $C_2$-$C_{10}$ alkenyl, optionally substituted linear or branched $C_2$-$C_{10}$ alkynyl, optionally substituted $C_4$-$C_8$ cyclyl, optionally substituted $C_3$-$C_8$ heterocyclyl, or $R^9$ and $R^{10}$ together with the carbon they are attached to form an optionally substituted 3-8 membered cyclyl or heterocyclyl, or $R^7$ and $R^9$ together with the carbons they are attached to form an optionally substituted 3-8 membered cyclyl, heterocyclyl, aryl or heteroaryl;

$L^1$ and $L^2$ are independently a bond, optionally substituted linear or branched $C_1$-$C_{10}$ alkylene, optionally substituted linear or branched $C_2$-$C_{10}$ alkenylene, or optionally substituted linear or branched $C_2$-$C_{10}$ alkynylene, wherein the backbone of $C_1$-$C_{10}$ alkylene, $C_2$-$C_{10}$ alkenylene, or $C_2$-$C_{10}$ alkynylene optionally comprises one or more heteroatoms;

T is H, a linear or branched, substituted or unsubstituted $C_1$-$C_{10}$ alkyl, linear or branched, substituted or unsubstituted $C_2$-$C_{10}$ alkenyl, linear or branched, substituted or unsubstituted $C_2$-$C_{10}$ alkynyl, optionally substituted cyclyl, optionally substituted heterocylcyl, optionally substituted aryl, optionally substituted heteroaryl, or PEG, wherein the backbone of $C_1$-$C_{10}$ alkyl, $C_2$-$C_{10}$ alkenyl, $C_2$-$C_{10}$ alkynyl optionally comprises one or more heteroatoms;

n is an integer from 0-5; and p is 0 or 1, provided that at least one of $R^7$, $R^8$, $R^9$ and $R^{10}$ is not hydrogen, or a salt, solvate, or ester thereof.

2. The compound of paragraph 1, having a structure of formula (IA), (IB) or (IC):

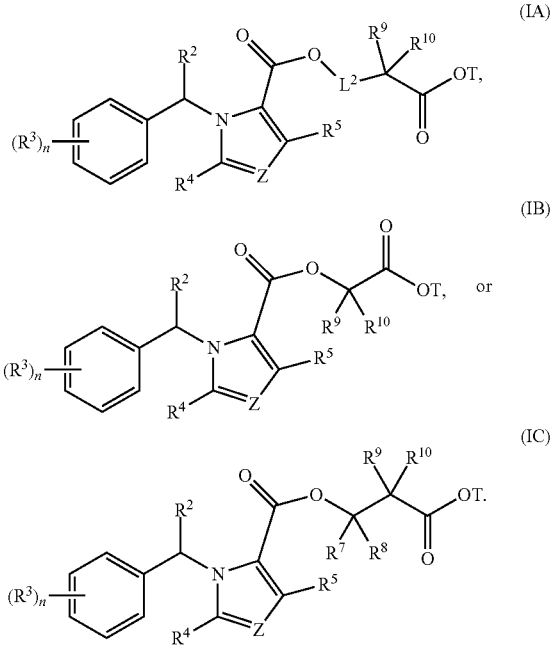

3. The compound of paragraph 1 or 2, wherein n is 0 or 1.
4. The compound of any of paragraphs 1-3, wherein p is 0 or 1.
5. The compound of any of paragraphs 1-4, wherein $L^1$ is a bond, optionally substituted linear or branched $C_1$-$C_{10}$alkylene, optionally substituted linear or branched $C_2$-$C_{10}$alkenylene, or optionally substituted linear or branched $C_2$-$C_{10}$alkynylene; wherein the backbone of $C_1$-$C_{10}$alkylene, $C_2$-$C_{10}$alkenylene, or $C_2$-$C_{10}$alkynylene optionally comprises one or more heteroatoms.
6. The compound of any of paragraphs 1-5, wherein $L^2$ is a bond, optionally substituted linear or branched $C_1$-$C_{10}$ alkylene, optionally substituted linear or branched $C_2$-$C_{10}$alkenylene, or optionally substituted linear or branched $C_2$-$C_{10}$alkynylene; wherein the backbone of $C_1$-$C_{10}$alkylene, $C_2$-$C_{10}$alkenylene, or $C_2$-$C_{10}$alkynylene optionally comprises one or more heteroatoms.
7. The compound of any of paragraphs 1-6, wherein T is hydrogen, optionally substituted $C_1$-$C_{10}$alkyl, or optionally substituted cyclyl or heterocyclyl.
8. The compound of paragraph 7, wherein T is selected from the group consisting of methyl, ethyl, propyl, isopropyl, butyl, t-butyl, pentyl, neopentyl, hexyl, 2-methylpentyl, 3-methylpentyl, 2,3-dimethylbutyl, 2,2-dimethylbutyl, 2-hydroxylpropyl, cyclopropyl, cyclobutyl, oxetanyl, morpholinyl, and oxazolindinyl.
9. The compound of any of paragraphs 1-8, wherein Z is N.
10. The compound of any of paragraphs 1-8, wherein Z is $CR^6$.
11. The compound of paragraph 10, wherein at least one of $R^4$ and $R^6$ is Br or CN.
12. The compound of paragraph 10 or 11, wherein $R^6$ is hydrogen.
13. The compound of any of paragraphs 1-12, wherein $R^4$ is hydrogen.
14. The compound of any of paragraphs 1-13, wherein $R^5$ is hydrogen.
15. The compound of any of paragraphs 1-14, wherein $R^2$ is optionally substituted $C_1$-$C_{10}$ alkyl.
16. The compound of paragraph 15, wherein $R^2$ is selected from the group consisting of methyl, ethyl, propyl, isopropyl, butyl, t-butyl, pentyl, neopentyl, hexyl, 2-methylpentyl, 3-methylpentyl, 2,3-dimethylbutyl, and 2,2-dimethylbutyl.
17. The compound of any of paragraphs 1-16, wherein the carbon to which $R^2$ is attached to has the R configuration.
18. The compound of any of paragraphs 1-17, wherein $R^9$ and $R^{10}$ are independently hydrogen, optionally substituted $C_1$-$C_{10}$alkyl, optionally substituted $C_4$-$C_6$cyclyl or optionally substituted $C_4$-$C_6$heterocyclyl; or $R^9$ and $R^{10}$ together with the carbon they are attached to form a 3-, 4-, 5, or 6-membered cyclyl.
19. The compound any of paragraphs 1-18, wherein $R^9$ and $R^{10}$ are independently optionally substituted $C_1$-$C_{10}$alkyl.
20. The compound of any of paragraphs 1-19, wherein $R^9$ and $R^{10}$ are the same.
21. The compound of any of paragraphs 1-18, wherein one of $R^9$ and $R^{10}$ is optionally substituted $C_1$-$C_{10}$alkyl, optionally substituted $C_4$-$C_6$cyclyl or optionally substituted $C_4$-$C_6$heterocyclyl, and the other is hydrogen.
22. The compound of any of paragraphs 1-21, wherein $R^9$ and $R^{10}$ are independently selected from the group consisting of hydrogen, methyl, ethyl, propyl, isopropyl, butyl, t-butyl, pentyl, neopentyl, hexyl, 2-methylpentyl, 3-methylpentyl, 2,3-dimethylbutyl, 2,2-dimethylbutyl, phenyl, pyridyl, thiophene, furanyl, pyrazolyl, cyclohexyl, cyclohexenyl, cyclopentyl, cyclopentenyl, and piperidinyl.
23. The compound of any of paragraphs 1-19, 21 or 22, wherein the carbon to which $R^9$ and $R^{10}$ are attached has the R configuration.
24. The compound of any of paragraphs 1-19, 21 or 22, wherein the carbon to which $R^9$ and $R^{10}$ are attached has the S configuration.
25. The compound of any of paragraphs 1-24, wherein $R^7$ and $R^8$ are independently hydrogen, optionally substituted $C_1$-$C_{10}$alkyl, optionally substituted $C_4$-$C_6$cyclyl or optionally substituted $C_4$-$C_6$heterocyclyl; or $R^7$ and $R^8$ together with the carbon they are attached to form a 3-, 4-, 5, or 6-membered cyclyl.
26. The compound of any of paragraphs 1-25, wherein $R^7$ and $R^8$ are independently optionally substituted $C_1$-$C_{10}$alkyl.
27. The compound of any of paragraphs 1-26, wherein $R^7$ and $R^8$ are the same.
28. The compound of any of paragraphs 1-25, wherein one of $R^7$ and $R^8$ is optionally substituted $C_1$-$C_{10}$alkyl, optionally substituted $C_4$-$C_6$cyclyl or optionally substituted $C_4$-$C_6$heterocyclyl, and the other is hydrogen.
29. The compound of any of paragraphs 1-28, wherein $R^7$ and $R^8$ are independently selected from the group consisting of hydrogen, methyl, ethyl, propyl, isopropyl, butyl, t-butyl, pentyl, neopentyl, hexyl, 2-methylpentyl, 3-methylpentyl, 2,3-dimethylbutyl, 2,2-dimethylbutyl, phenyl, pyridyl, thiophene, furanyl, pyrazolyl, cyclohexyl, cyclohexenyl, cyclopentyl, cyclopentenyl, and piperidinyl.
30. The compound of any of paragraphs 1-27, 28 or 29, wherein the carbon to which $R^7$ and $R^8$ are attached has the R configuration.
31. The compound of any of paragraphs 1-27, 28 or 29, wherein the carbon to which $R^7$ and $R^8$ are attached has the S configuration.

32. The compound of any of paragraphs 1-31, wherein $R^7$ and $R^9$ together with the carbons they are attached to form an optionally substituted 3-8 membered cyclyl or heterocyclyl.

33. A compound according to formula (I)

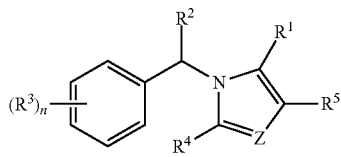

FORMULA (I)

wherein,
$R^1$ is $L^1C(O)OL^2$-$[C(R^7R^8)]_p$—$C(R^9R^{10})$—$C(O)OT$;
$R^2$ is $R^1$ or a linear or branched, substituted or unsubstituted $C_1$-$C_{10}$ alkyl, $C_2$-$C_{10}$ alkenyl, or $C_2$-$C_{10}$ alkynyl, wherein backbone of $C_1$-$C_{10}$ alkyl, $C_2$-$C_{10}$ alkenyl, or $C_2$-$C_{10}$ alkynyl can contain one or more heteroatoms;
each $R_3$ is independently halogen, CN, $CF_3$, $SR^2$, $SOR^2$, $SO_2R^2$, $OR^2$, $CO_2H$, $CO_2R^2$, $N(R^2)_2$, $NHR^2$, $NO_2$, or $R^2$;
Z is N or $CR^5$;
$R^4$, $R^5$, and $R^6$ are independently hydrogen, halogen, CN, $CF_3$, $SR^2$, $SOR^2$, $SO_2R^2$, $OR^2$, $CO_2H$, $CO_2R^2$, $N(R^2)_2$, $NHR^2$, $NO_2$, or $R^2$;
$R^7$, $R^8$, $R^9$ and $R^{10}$ are independently hydrogen, linear or branched, substituted or unsubstituted $C_1$-$C_{10}$ alkyl, linear or branched, substituted or unsubstituted $C_2$-$C_{10}$ alkenyl, linear or branched, substituted or unsubstituted $C_2$-$C_{10}$ alkynyl, or $R^7$ and $R^8$ together with the carbon they are attached to form a 3-8 membered cyclyl or heterocyclyl, or $R^9$ and $R^{10}$ together with the carbon they are attached to form a 3-8 membered cyclyl or heterocyclyl, provided that at least one of $R^7$, $R^8$, $R^9$ and $R^{10}$ is not hydrogen, and wherein the backbone of the $C_1$-$C_{20}$ alkylene, $C_1$-$C_{10}$ alkyl, $C_2$-$C_{10}$ alkenyl, or $C_2$-$C_{10}$ alkynyl can contain one or more heteroatoms;
$L^1$ and $L^2$ are independently a bond, a substituted or unsubstituted $C_1$-$C_{10}$ alkylene, $C_2$-$C_{10}$ alkenylene, or $C_2$-$C_{10}$ alkynylene, wherein backbone of alkylene can contain one or more heteroatoms;
T is H, a linear or branched, substituted or unsubstituted $C_1$-$C_{10}$ alkyl, linear or branched, substituted or unsubstituted $C_2$-$C_{10}$ alkenyl, linear or branched, substituted or unsubstituted $C_2$-$C_{10}$ alkynyl, optionally substituted cyclyl, optionally substituted heterocyclyl, optionally substituted aryl, optionally substituted heteroaryl, or PEG, wherein the backbone of $C_1$-$C_{10}$ alkyl, $C_2$-$C_{10}$ alkenyl, $C_2$-$C_{10}$ alkynyl can contain one or more heteroatoms;
n is an integer from 0-5; and
p is 0 or 1.

34. The compound of paragraph 33, wherein said compound is present in the form of a pure enantiomer.

35. The compound of any of paragraphs 33-34, wherein the carbon to which $R^2$ is attached has the R configuration.

36. The compound of any of paragraphs 33-35, wherein $R^2$ is selected from the group consisting of methyl, ethyl, propyl, isopropyl, butyl, t-butyl, pentyl, neopentyl, hexyl, 2-methylpentyl, 3-methylpentyl, 2,3-dimethylbutyl, and 2,2-dimethylbutyl.

37. The compound of any of paragraphs 33-36, wherein T is selected from the group consisting of hydrogen, methyl, ethyl, propyl, isopropyl, butyl, t-butyl, pentyl, neopentyl, hexyl, 2-methylpentyl, 3-methylpentyl, 2,3-dimethylbutyl, 2,2-dimethylbutyl, and 2-hydroxylpropyl.

38. The compound of any of paragraphs 33-37, wherein n is 0 or 1.

39. The compound of any of paragraphs 33-38, wherein $L^1$ is a bond.

40. The compound of any of paragraphs 33-39, wherein $L^2$ is a bond.

41. The compound of any of paragraphs 33-40, wherein one of $R^9$ or $R^{10}$ is $C_1$-$C_{10}$ alkyl and the other is hydrogen.

42. The compound of any of paragraphs 33-40, wherein both of $R^9$ and $R^{10}$ are independently $C_1$-$C_{10}$ alkyl.

43. The compound of paragraph 41 or 42, wherein the carbon to which $R^9$ and $R^{10}$ are attached has the R configuration.

44. The compound of paragraph 41 or 42, wherein the carbon to which $R^9$ and $R^{10}$ are attached has the S configuration.

45. The compound of any of paragraphs 41-44, wherein $R^9$ and $R^{10}$ are selected from the group consisting of hydrogen, methyl, ethyl, propyl, isopropyl, butyl, t-butyl, pentyl, neopentyl, hexyl, 2-methylpentyl, 3-methylpentyl, 2,3-dimethylbutyl, 2,2-dimethylbutyl and any combinations thereof.

46. The compound of any of paragraphs 42-45, wherein $R^9$ and $R^{10}$ are both same or together with the carbon they are attached to form a 3 membered ring.

47. The compound of any of paragraphs 33-46, wherein p is 0.

48. The compound of any of paragraphs 33-46, wherein one of $R^7$ and $R^8$ is $C_1$-$C_{10}$ alkyl and the other is hydrogen.

49. The compound of any of paragraphs 33-46, wherein both of $R^7$ and $R^8$ are independently $C_1$-$C_{10}$ alkyl.

50. The compound of paragraph 48 or 49, wherein the carbon to which $R^7$ and $R^8$ are attached has the R configuration.

51. The compound of paragraph 48 or 49, wherein the carbon to which $R^7$ and $R^8$ are attached has the S configuration.

52. The compound of any of paragraphs 48-51, wherein $R^7$ and $R^8$ are selected from the group consisting of hydrogen, methyl, ethyl, propyl, isopropyl, butyl, t-butyl, pentyl, neopentyl, hexyl, 2-methylpentyl, 3-methylpentyl, 2,3-dimethylbutyl, 2,2-dimethylbutyl and any combinations thereof.

53. The compound of any of paragraphs 48-52, wherein $R^7$ and $R^7$ are both the same or together with the carbon they are attached to form a 3 membered ring.

54. The compound of any of paragraphs 33-53, wherein $R^5$ is hydrogen.

55. The compound of any of paragraphs 33-54, wherein at least one of $R^4$ and $R^6$ is hydrogen.

56. The compound of any of paragraphs 33-55, wherein at least one of $R^4$ and $R^6$ is Br or CN.

57. The compound of paragraph 56, wherein $R^4$ is H and $R^6$ is Br or CN.

58. The compound of paragraph 56, wherein $R^4$ is Br or CN.

59. A compound having a structure of formula (I):

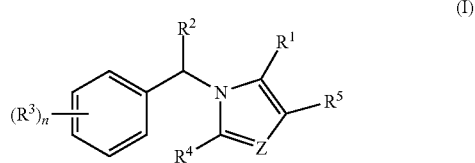

wherein
R¹ is $L^1C(O)OL^2-[C(R^7R^8)]_p-C(R^9R^{10})-C(O)OT$;
R² is R¹ or a linear or branched, substituted or unsubstituted $C_1-C_{10}$alkyl, $C_2-C_{10}$alkenyl, or $C_2-C_{10}$alkynyl, wherein the backbone of $C_1-C_{10}$alkyl, $C_2-C_{10}$alkenyl, or $C_2-C_{10}$alkynyl optionally comprises one or more heteroatoms;
each R³ is independently halogen, CN, $CF_3$, $SR^2$, $SOR^2$, $SO_2R^2$, $OR^2$, $CO_2H$, $CO_2R^2$, $N(R^2)_2$, $NHR^2$, $NO_2$, or R²;
Z is N or $CR^6$;
R⁴, R⁵, and R⁶ are independently hydrogen, halogen, CN, $CF_3$, $SR^2$, $SOR^2$, $SO_2R^2$, $OR^2$, $CO_2H$, $CO_2R^2$, $N(R^2)_2$, $NHR^2$, $NO_2$, or R²;
R⁷ and R⁸ are independently hydrogen, linear or branched, substituted or unsubstituted $C_1-C_{10}$alkyl, $C_2-C_{10}$alkenyl, or $C_2-C_{10}$alkynyl, or R⁷ and R⁸ taken together form an optionally substituted 3-8 membered carbocyclyl or heterocyclyl;
R⁹ and R¹⁰ are independently hydrogen, optionally substituted $C_4-C_8$ cyclyl or optionally substituted $C_3-C_8$heterocyclyl, with the proviso that at least one of R⁹, and R¹⁰ is not hydrogen;
or R⁷ and R⁹ taken together form an optionally substituted 3-8 membered carbocyclyl, heterocyclyl, aryl, or heteroaryl;
L¹ and L² are independently a bond, a linear or branched, substituted or unsubstituted $C_1-C_{10}$alkylene, $C_2-C_{10}$alkenylene, or $C_2-C_{10}$alkynylene; wherein the backbone of $C_1-C_{10}$alkylene, $C_2-C_{10}$alkenylene, or $C_2-C_{10}$alkynylene optionally comprises one or more heteroatoms;
T is hydrogen, linear or branched, substituted or unsubstituted $C_1-C_{10}$alkyl, $C_2-C_{10}$alkenyl, $C_2-C_{10}$alkynyl, optionally substituted cyclyl, optionally substituted heterocyclyl, optionally substituted aryl, optionally substituted heteroaryl, or PEG, wherein the backbone of $C_1-C_{10}$alkyl, $C_2-C_{10}$alkenyl, or $C_2-C_{10}$alkynyl optionally comprises one or more heteroatoms;
each n is an integer of 0-5; and
each p is 0 or 1,
or a salt, solvate, or ester thereof.
60. The compound of paragraph 59, wherein L is a linear or branched, substituted or unsubstituted $C_1-C_{10}$alkylene, $C_2-C_{10}$alkenylene, or $C_2-C_{10}$alkynylene; wherein the backbone of $C_1-C_{10}$alkylene, $C_2-C_{10}$alkenylene, or $C_2-C_{10}$alkynylene optionally comprises one or more heteroatoms.
61. The compound of paragraph 59 or 60, wherein L² is a linear or branched, substituted or unsubstituted $C_1-C_{10}$alkylene, $C_2-C_{10}$alkenylene, or $C_2-C_{10}$alkynylene; wherein the backbone of $C_1-C_{10}$alkylene, $C_2-C_{10}$alkenylene, or $C_2-C_{10}$alkynylene optionally comprises one or more heteroatoms.
62. The compound of paragraph 59 or 61 having a structure of formula (IA):

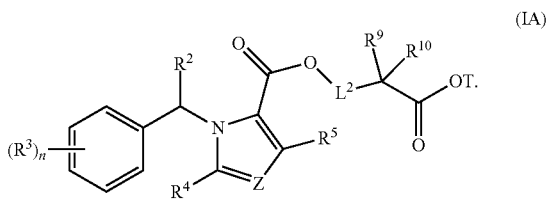

(IA)

63. The compound of paragraph 59 having a structure of formula (IB):

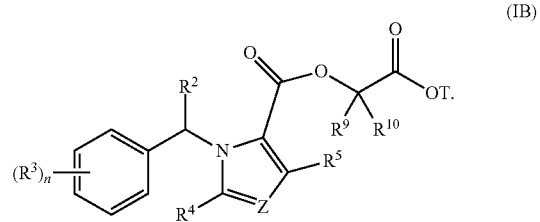

(IB)

64. The compound of paragraph 59 having a structure of formula (IC):

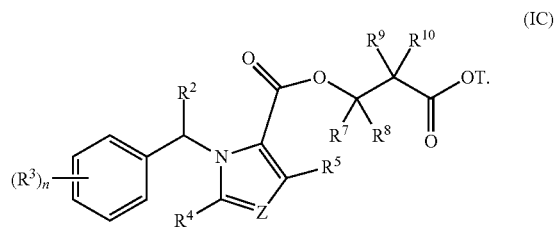

(IC)

65. The compound of any one of paragraphs 59 to 64, wherein Z is N.
66. The compound of any one of paragraphs 59 to 64, wherein Z is $CR^6$.
67. The compound of paragraph 66, wherein R⁶ is H.
68. The compound of any one of paragraphs 59 to 67, wherein R⁹ is optionally substituted $C_4-C_6$cyclyl and R¹⁰ is hydrogen.
69. The compound of any one of paragraphs 59 to 67, wherein R⁹ is optionally substituted $C_4-C_6$heterocyclyl and R¹⁰ is hydrogen.
70. The compound of any one of paragraphs 59 to 69, wherein R⁷ and R⁹ together form an optionally substituted 3-8 membered cyclyl or heterocyclyl.
71. The compound of any one of paragraphs 59 to 70, wherein R⁴ is hydrogen.
72. The compound of any one of paragraphs 59 to 71, wherein R⁵ is hydrogen.
73. The compound of any one of paragraphs 59 to 72, wherein n is 0.
74. The compound of any one of paragraphs 59 to 72, wherein n is 1.
75. The compound of any one of paragraphs 59 to 74, wherein R² is optionally substituted $C_1-C_{10}$ alkyl.
76. The compound of paragraph 75, wherein R² is methyl, ethyl, n-propyl, isopropyl, butyl, sec-butyl, iso-butyl, tert-butyl, pentyl, neopentyl, hexyl, 2-methylpentyl, 3-methylpentyl, 2,3-dimethylbutyl, or 2,2-dimethylbutyl.
77. The compound of any one of paragraphs 59 to 76, wherein the carbon to which R² is attached is in the R configuration.
78. The compound of any one of paragraphs 59 to 77, wherein T is optionally substituted $C_1-C_{10}$alkyl.
79. The compound of paragraph 78, wherein T is methyl or ethyl.
80. The compound of any one of paragraphs 59 to 77, wherein T is optionally substituted cyclyl or heterocyclyl.
81. The compound of paragraph 80, wherein T is cyclopropyl, cyclobutyl, oxetanyl, morpholinyl, or oxazolindinyl.

82. The compound of any of paragraphs 1-32, wherein the compound is in the form of a single diastereomer
83. The compound of any of paragraphs 1-33, wherein the compound is in the form of a single enantiomer.
84. The compound of any of paragraphs 1-34, wherein the compound is in the form of a salt.
85. The compound of any of paragraphs 1-34, wherein the compound is in the form of a solvate.
86. The compound of paragraph 1, wherein the compound of formula (I) is selected from the group consisting of

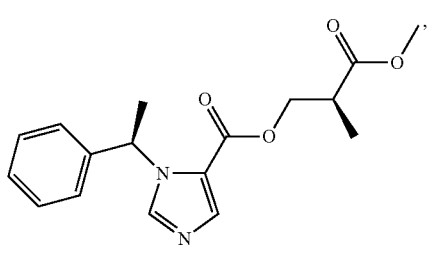

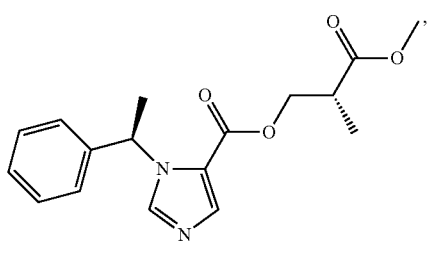

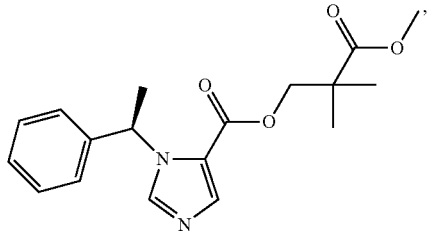

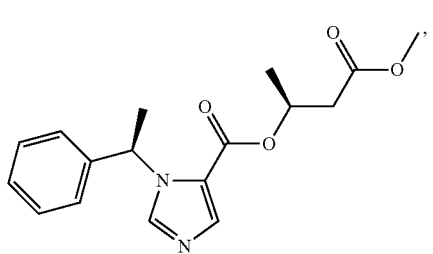

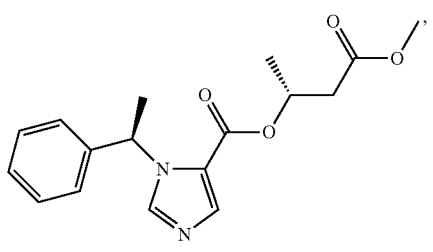

-continued

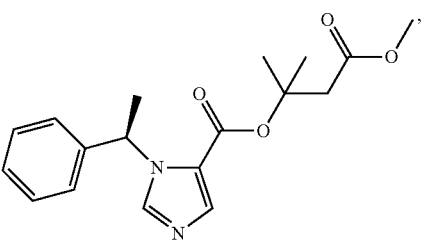

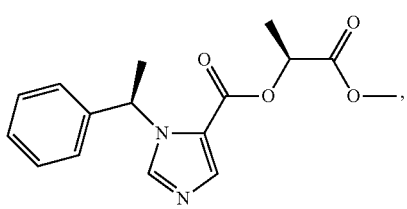

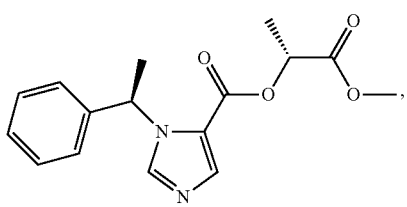

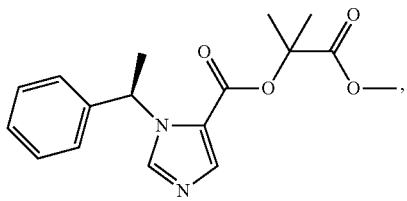

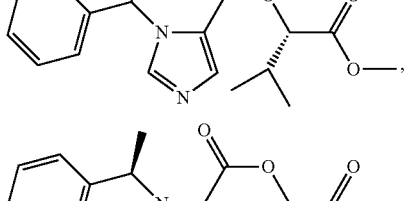

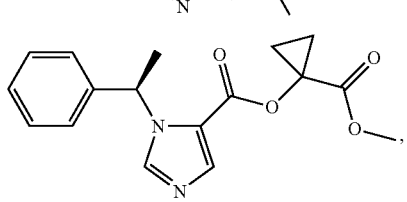

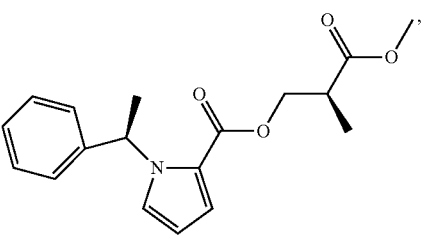

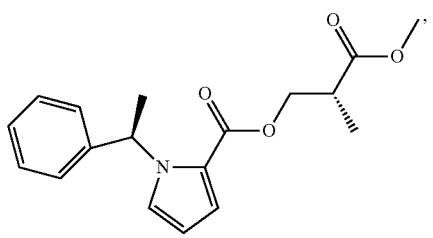
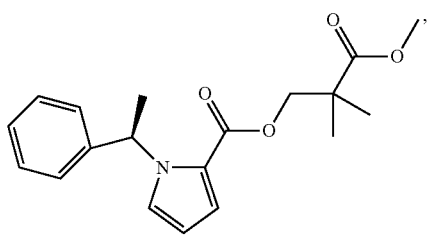
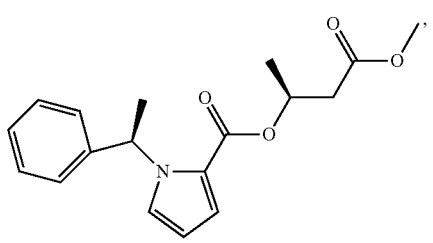
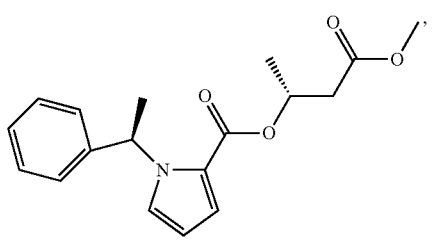
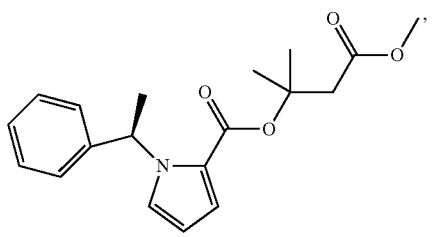
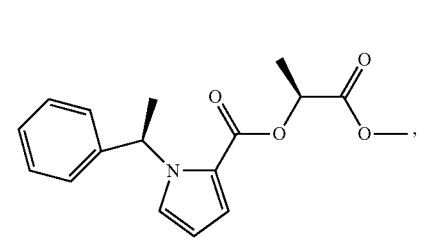
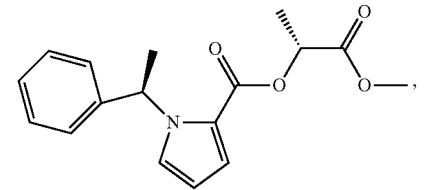
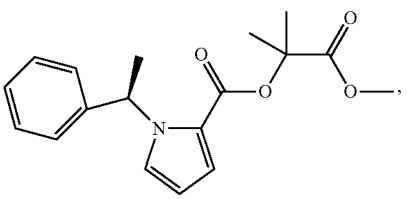
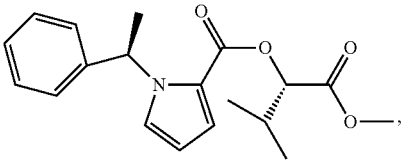
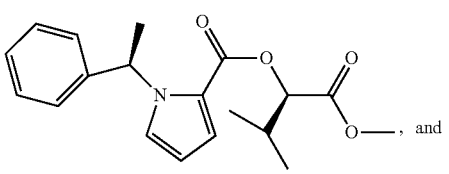
, and
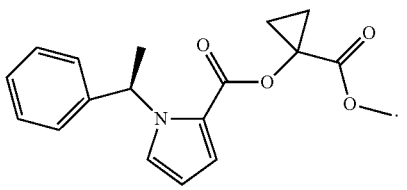
87. The compound of paragraph 1, wherein the compound of formula (I) is selected from the group consisting of
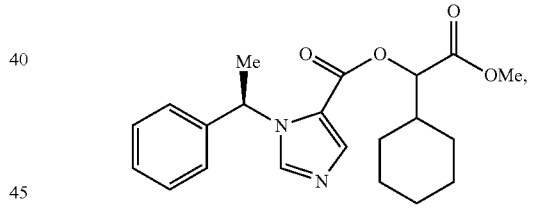
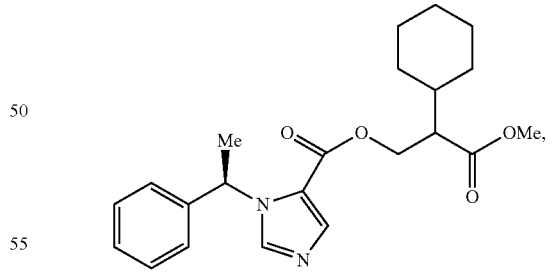
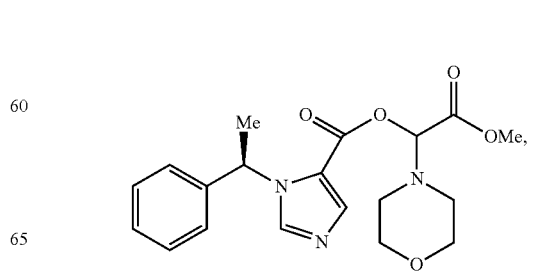

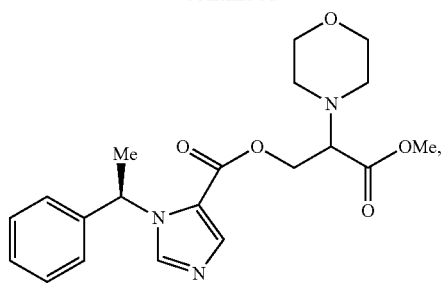
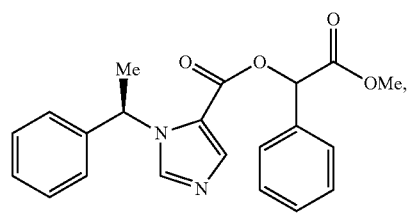
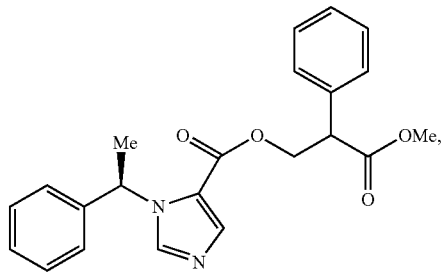
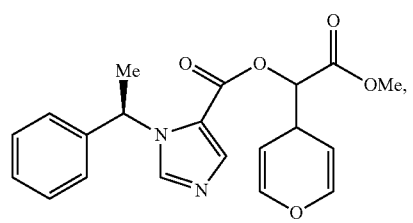
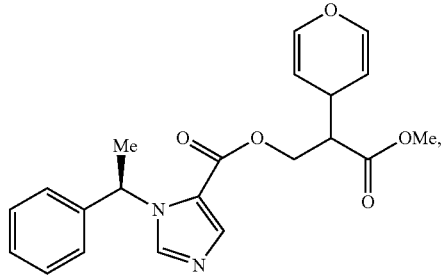
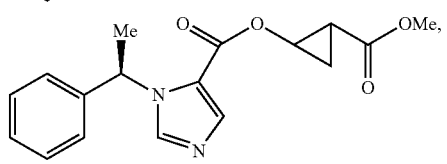
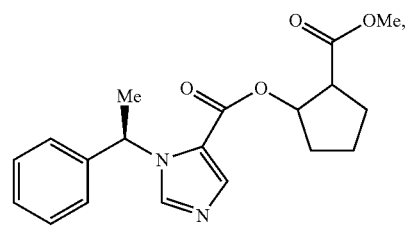
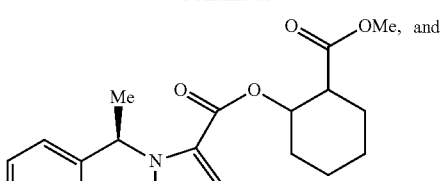
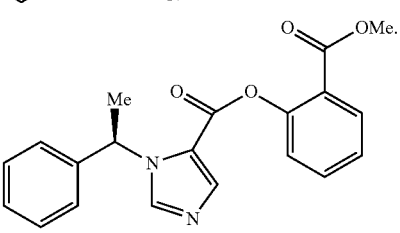
88. A compound having a structure selected from the group consisting of
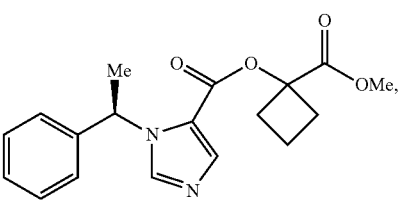
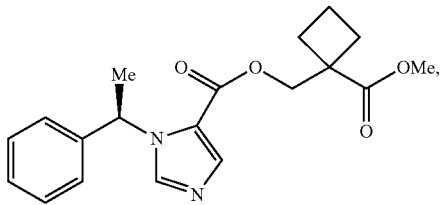
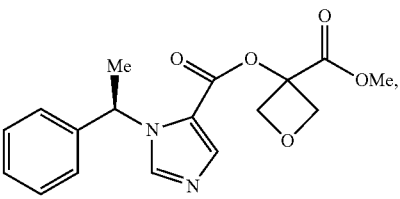
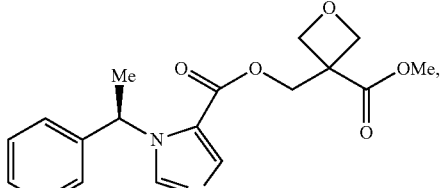
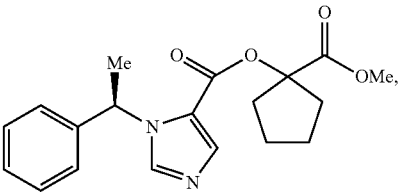

-continued

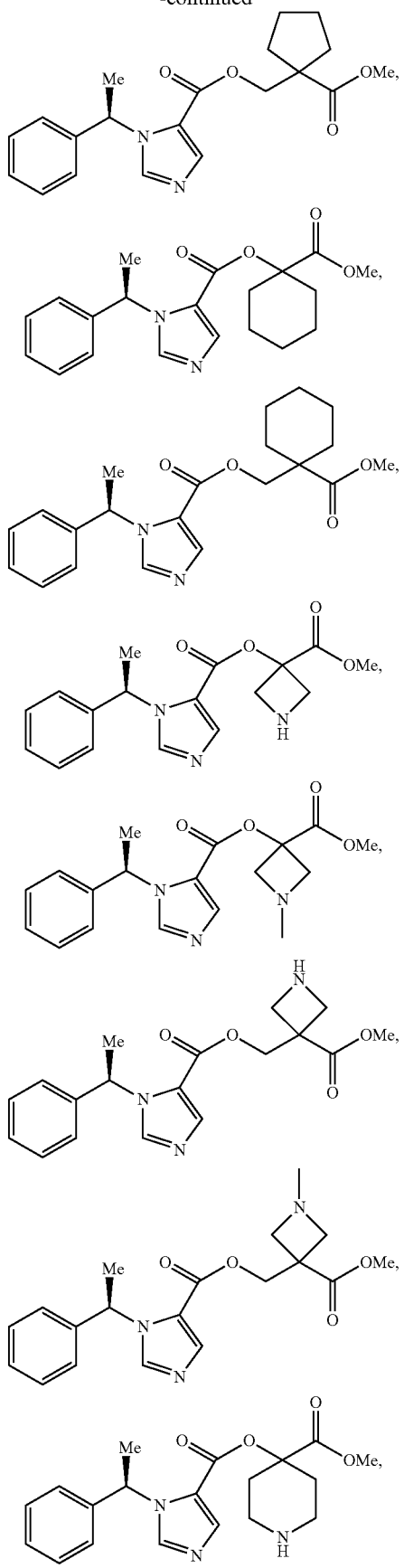

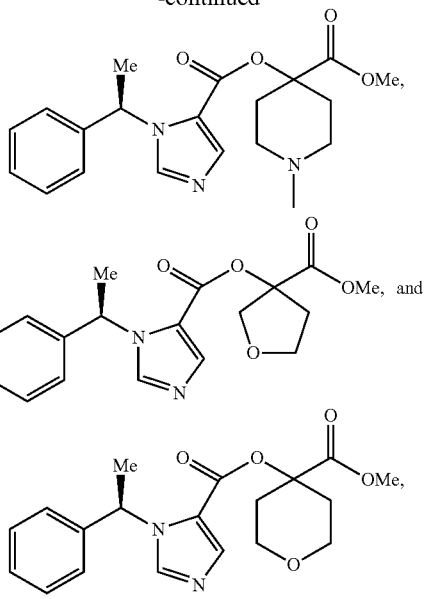

or a salt, solvate, or ester thereof.

89. A pharmaceutical composition comprising a compound of any of paragraphs 1-88 and a pharmaceutically acceptable carrier.

90. A method for providing anesthesia or sedation to a subject comprising administering to the subject a therapeutically effective amount of a compound of paragraphs 1-89 or a pharmaceutical composition of paragraph 89.

91. The compound of any of paragraphs 1-88 for use as an anesthetic or sedative.

92. Use of a compound of any of paragraphs 1-88 in the preparation of a medicament for use as an anesthetic or sedative.

93. Use of a compound of any of paragraphs 1-88 as an anesthetic or sedative.

94. The method, compound or use of any of paragraphs 90-93, wherein the subject is a mammal.

95. The method, compound or use of any of paragraphs 91-93, wherein the subject is a human.

96. A method of preparing a compound of paragraph 1, 33, or 59, comprising:
   (i) hydrolyzing ethyl-1-(1-phenylethyl)-1H-imidazole-5-carboxylate to obtain 1-(1-phenylethyl)-1H-imidazole-5-carboxylic acid; and
   (ii) reacting the carboxylic acid with an alcohol of structure HO-L$^2$-[C(R$^7$R$^8$)]$_p$—C(R$^9$R$^{10}$)—C(O)OT, wherein L$^2$, R$^7$, R$^8$, R$^9$, R$^{10}$, T and p are as defined for formula (I).

97. A method of preparing a compound of paragraph 1, 33, or 59, comprising:
   (i) coupling a compound of formula (II), and (a) a compound of formula (III) or (b) a compound of formula (IV):

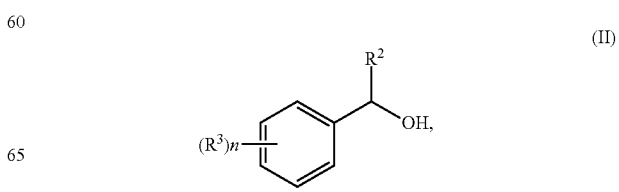

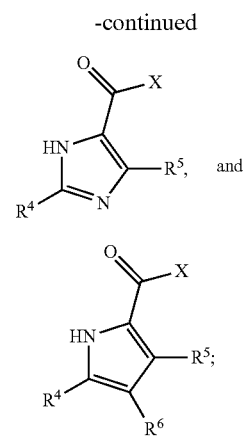

(III)

(IV)

wherein $R^2$, $R^3$, $R^4$, $R^5$, $R^6$, and n are as defined for formula (I) and X is carboxylic acid protecting group;

(ii) removing the protecting group X to form a carboxylic acid; and (iii) coupling the carboxylic acid with an alcohol of structure HO-$L^2$-[C($R^7R^8$)]$_p$—C($R^9R^{10}$)—C(O)OT, wherein $L^2$, $R^7$, $R^8$, $R^9$, $R^{10}$, T and p are as defined for formula (I).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

One skilled in the art would also readily appreciate that the present invention is well adapted to carry out the objects and obtain the ends and advantages mentioned, as well as those inherent herein. The molecular complexes and the methods, procedures, treatments, molecules, specific compounds described herein are presently representative of preferred embodiments, are exemplary, and are not intended as limitations on the scope of the invention. Changes therein and other uses will occur to those skilled in the art which are encompassed within the spirit of the invention are defined by the scope of the claims.

EXAMPLES

The disclosure is further illustrated by the following examples which should not be construed as limiting. The examples are illustrative only, and are not intended to limit, in any manner, any of the aspects described herein.

Example 1

Materials and Methods

Animals:

All studies were conducted in accordance with rules and regulations of the Subcommittee on Research Animal Care at the Massachusetts General Hospital, Boston, Mass. Adult male Sprague-Dawley rats (230-350 gm) were purchased from Charles River Laboratories (Wilmington, Mass.) and housed in the Massachusetts General Hospital Center for Comparative Medicine animal care facility. All drugs were administered through a femoral venous catheter pre-implanted by the vendor prior to animal delivery to our animal care facility.

Hypnotic Drugs:

Etomidate was purchased from Bachem (Torrance, Calif.). Etomidate esters were synthesized (>99% purity) either within our laboratory or by Aberjona Laboratories (Beverly, Mass.) using the following previously described general procedure.[12]

Step 1: Synthesis of (R)-1-(1-phenylethyl)-1H-imidazole-5-carboxylic Acid (R)-ethyl-1-(1-phenylethyl)-1H-imidazole-5-carboxylate.HCl ((R)-etomidate.HCl) in methanol and 10% aqueous NaOH was refluxed for 30 min. After cooling, the solution was neutralized with 12 M HCl. The mixture was dried by rotary evaporation, the residue suspended in methanol-dichloromethane 1:4 v/v, and the sodium chloride removed by filtration. (R)-1-(1-phenylethyl)-1H-imidazole-5-carboxylic acid 1 was obtained by chromatography on a silica gel column equilibrated with methanol-dichloromethane 1:4 V/V.

Step 2: Synthesis of Etomidate Ester (FIG. 2)

Figure 2:
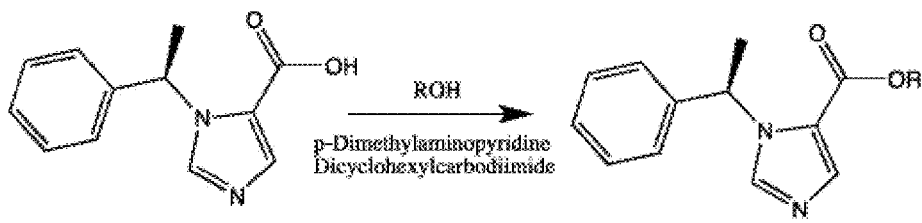
FIG. 2 shows one approach to synthesis of compounds of formula (I).
Figure 2:
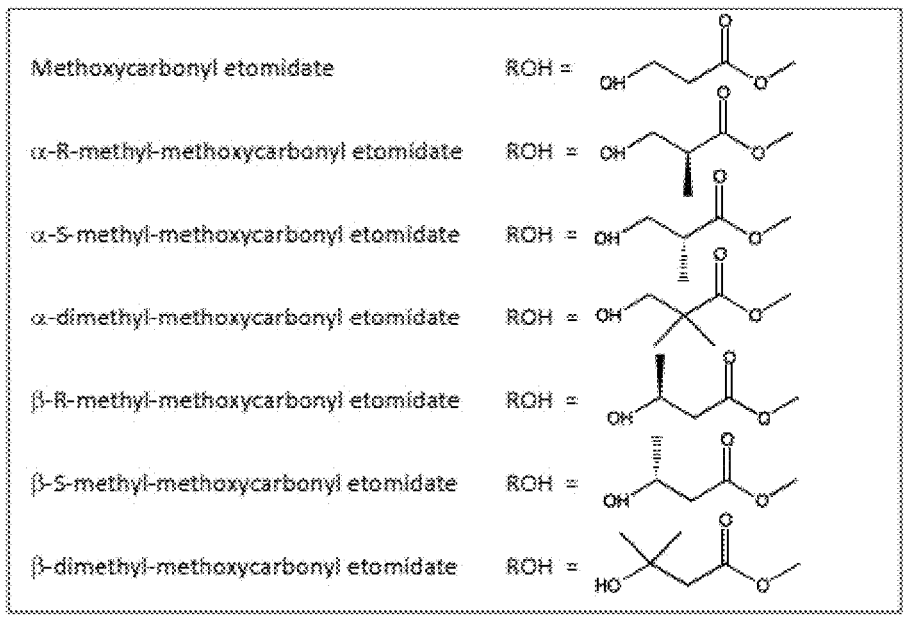
Figure 2:
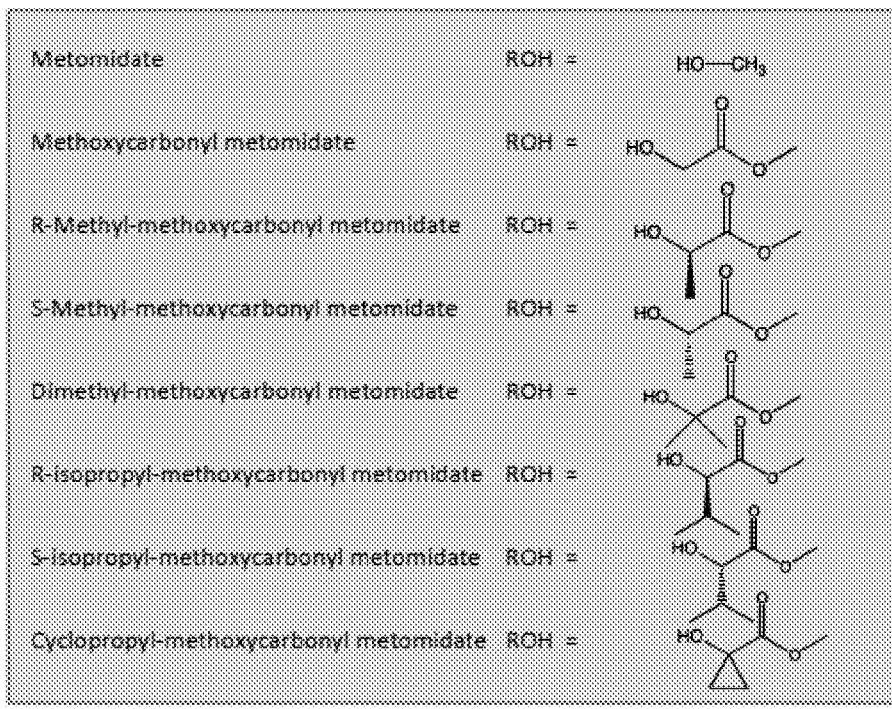

Dicyclohexylcarbodiimide and p-dimethylaminopyridine were added to a mixture composed of (R)-1-(1-phenylethyl)-1H-imidazole-5-carboxylic and the desired alcohol (in equimolar ratios) in anhydrous dichloromethane (FIG. 2). These alcohols were either purchased commercially or synthesized essentially as described by Bartlett and Rylander. The solution was stirred at room temperature for 48 h. The precipitate was removed by filtration and the clear solution applied to a silica gel column equilibrated with dichloromethane. Elution with 10% ether in dichloromethane gave the product, which was further purified by preparative thin layer chromatography with hexane-ethyl acetate 1:1 v/v on 1 mm thick silica gel plate. The identity of the product was confirmed by nuclear magnetic resonance spectroscopy.

Figure 3:
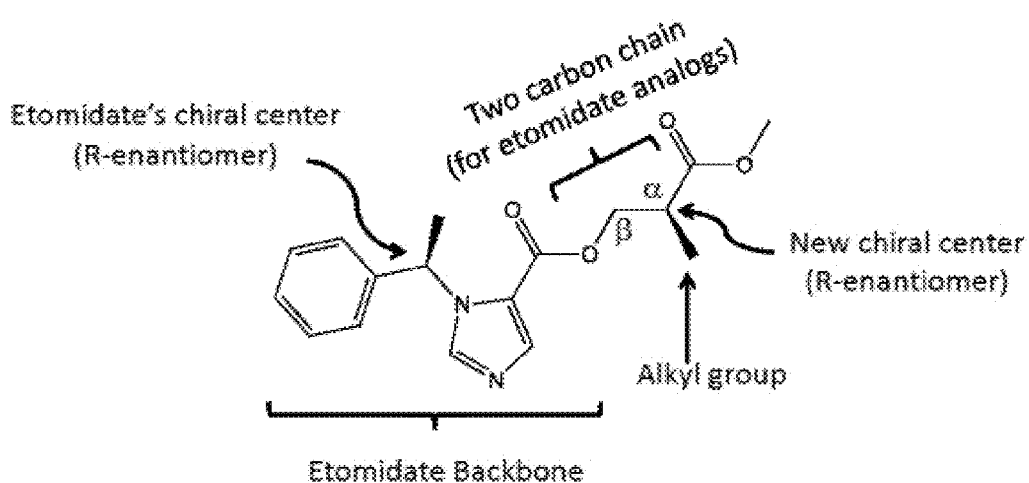
FIG. 3 shows the nomenclature system for the compounds of formula (I).

The inventors used a nomenclature system for these new compounds that was based upon four criteria (FIG. 3). First, the length of the carbon chain linking the labile ester to the etomidate backbone. Etomidate analogs have two methylene groups in this chain whereas metomidate analogs have only one. Second, the identity of the aliphatic group or groups (i.e. methyl, dimethyl, isopropyl, or cyclopropyl). Third, the specific location of the aliphatic group on the carbon chain (for etomidate esters with carbon linkers composed of two methylene groups). The carbon immediately adjacent to the metabolically-labile ester was defined as the α carbon whereas the more distant one was the β carbon. Finally, the enantiomeric configuration of the new chiral center (R or S) that results from the addition of the new aliphatic group.

Measurement of In Vivo Hypnotic Potency and Duration of Action:

The hypnotic potencies of etomidate, metomidate, and etomidate esters were assessed in rats using a loss of righting reflexes (LORR) assay.[12] Briefly, the desired dose of hypnotic in dimethyl sulfoxide or saline vehicle was rapidly injected through the femoral venous catheter followed by a 1-ml normal saline flush. Immediately after injection, rats were turned supine. A rat was judged to have LORR if it failed to right itself (onto all four paws) after drug administration. A stopwatch was used to measure the duration of LORR, which was defined as the time from drug injection until the animal spontaneously righted itself. For each etomidate ester, the $ED_{50}$ for LORR was determined from a data set possessing at least 15 doses using the method of Waud.[20]

In Vitro Metabolic Half-Life of Hypnotics in Rat Blood:

On the day of study, whole blood was drawn from the femoral venous catheters of 3 Sprague-Dawley rats (1-2 ml/rat), immediately anticoagulated with heparin (38 U), pooled, and stored on ice. A 1 ml aliquot of blood was warmed at 37° C. for 5 minutes and hypnotic (from a 40 mM in dimethyl sulfoxide stock solution) was added to a final concentration of 100 μM. After the desired incubation time, a 150 μl sample was removed and the metabolic reaction was quenched with 150 μl acetonitrile (Sigma-Aldrich, St. Louis, Mo.). Zero time point samples were prepared by adding 150 μl acetonitrile to blood prior to adding hypnotic (from a 4 mM in dimethyl sulfoxide stock solution). The quenched samples were centrifuged and the resultant supernatant separated and stored at −20° C. until analyzed. Hypnotic concentrations in thawed samples were determined by high performance liquid chromatography using a Varian Prostar system with a 4.6×250 mm Proto 300 C18 column (Nest Group, Southborough, Mass.) with the UV detector set at 240 nm. A linear gradient 20% to 45% acetonitrile in water with 0.005% trifluoroacetic acid (Thermo Scientific, Rockford, Ill.) over 20 minutes was used with a flow rate of 1 ml/min. The lower limit of quantitation of this assay was 3 μM and the precision and accuracy was <10% at 10 μM.

Octanol:Water Partition Coefficients of Etomidate Esters:

One mg of each hypnotic was added to 10 ml of water buffered with 10 mM Tris (pH 7.4) and 0.5 ml or 1 ml of octanol. The mixture was stirred overnight and then centrifuged to more fully separate the organic and aqueous phases. The relative hypnotic concentrations in each phase (i.e. the partition coefficient) were determined by high performance liquid chromatography as described for blood.

Statistical Analysis:

Unless indicated otherwise, data are reported as mean+/−SD. Statistical analyses were done using Prism v5.0 for the Macintosh (GraphPad Software, Inc., LaJolla, Calif.) or Igor Pro 6.1 (Wavemetrics, Lake Oswego, Oreg.).

Results and Discussion

Figure 4:
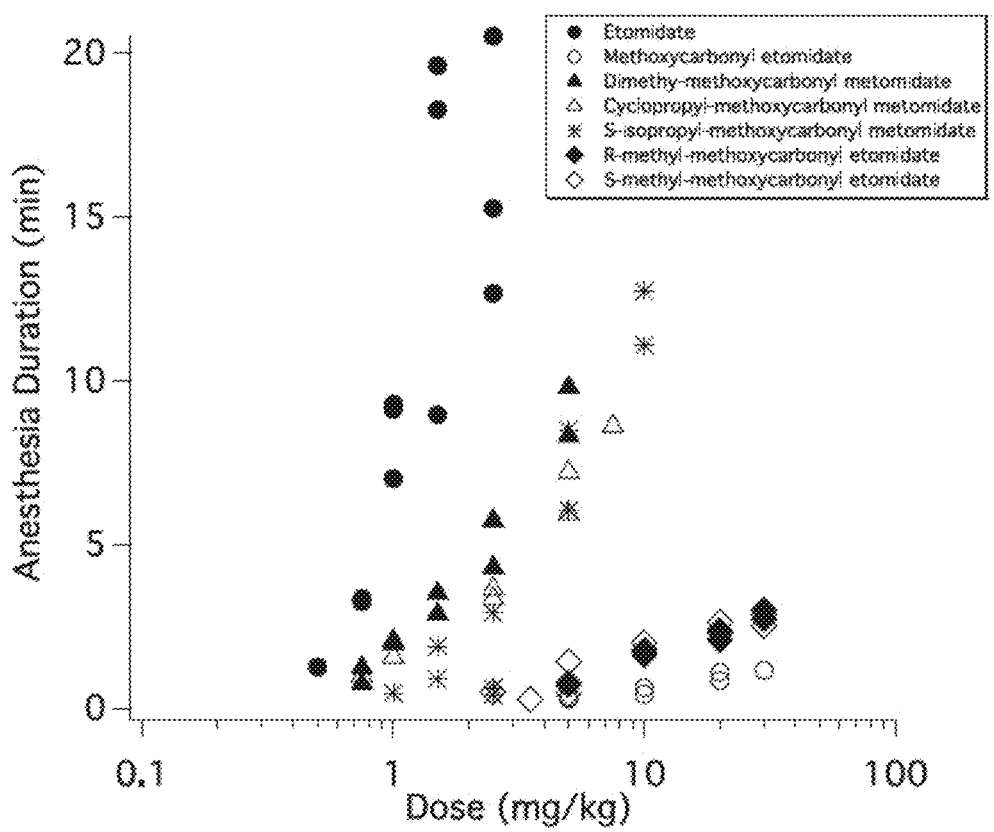
FIG. 4 shows duration of anesthesia as a function of amount of etomidate analogue administered.

Hypnotic Activity of Etomidate Esters:

When administered as an IV bolus to rats, all etomidate esters produced LORR rapidly, dose-dependently, and at the highest doses studied, all rats had LORR. The ED50s for LORR ranged from 0.69±0.04 mg/kg for cyclopropyl-methoxycarbonyl metomidate to 9.6±1.9 for R-methyl-methoxycarbonyl metomidate (FIG. 4 and Table 1). Two rats died during our studies after receiving an etomidate ester. One had received a 20 mg/kg dose of dimethyl-methoxycarbonyl metomidate, which was subsequently determined to be 28-fold higher than the ED50 for LORR. The other rat died after receiving a 20 mg/kg dose of R-isopropyl-methoxycarbonyl metomidate.

The inventors found no consistent relationship between an etomidate ester's potency for producing LORR and its hydrophobicity as reflected by its octanol:water partition coefficient (Table 1). However for the four compounds that exist as diastereometric pairs (α-methyl-methoxycarbonyl etomidate, β-methyl-methoxycarbonyl etomidate, methyl-methoxycarbonyl metomidate, and isopropyl-methoxycarbonyl metomidate), the hypnotic potency was higher (ED50 for LORR was lower) for the S form versus the R form. This difference was larger for the two metomidate analogs (methyl-methoxycarbonyl metomidate and isopropyl-methoxycarbonyl metomidate R/S ED50 ratios were 2.7 and 3.0, respectively) versus the two etomidate analogs (α-methyl-methoxycarbonyl etomidate and β-methyl-methoxycarbonyl etomidate R/S ED50 ratios were 1.7 and 1.2 respectively).

For representative etomidate esters, FIG. 4 plots the duration of LORR as a function of etomidate ester dose on a semi-logarithmic scale. It demonstrates that the duration of LORR increased approximately linearly with the logarithm of the etomidate ester dose. The slope of this relationship, which is inversely related to the rate of drug clearance from the brain, ranged from 1.0±0.3 for methoxycarbonyl etomidate to 12.1±1.1 for S-isopropyl-methoxycarbonyl metomidate (Table 1).[21,22] For comparison, this plot also shows the same relationship for etomidate and metomidate, which had slopes of 24±4.7 and Y, respectively.

In Vitro Determination of the Metabolic Half-Life of Etomidate Esters in Rat Blood.

Figure 5:
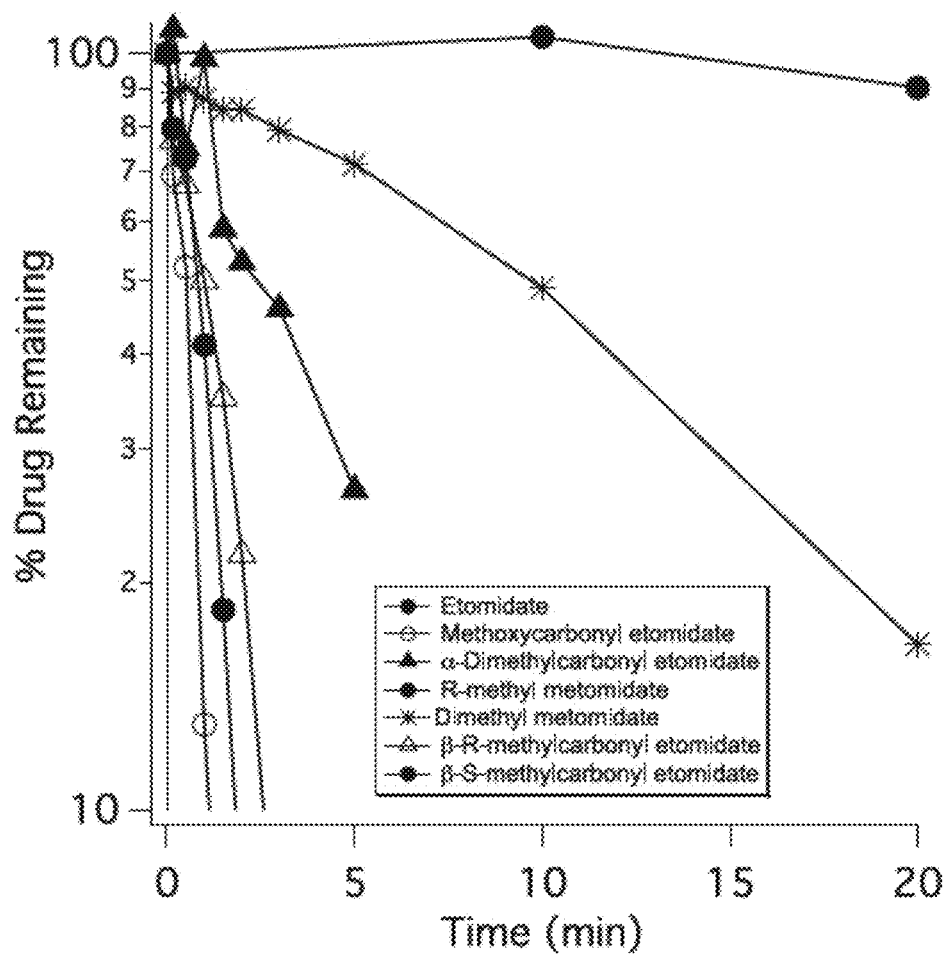
FIG. 5 shows % drug remaining over time after incubation in rat blood.

To assess the susceptibility of each etomidate ester to metabolism, we added each compound to rat blood and measured the incubation time-dependent reduction in etomidate ester concentration. For representative etomidate esters, FIG. 5 shows that the concentration of drug decreased with incubation time in blood in an approximately first-order manner. We could calculate metabolic half-lives for twelve of the fourteen etomidate esters. Their half-lives ranged from 0.14 min (95% CI 0.31-0.60 min) for methoxycarbonyl etomidate to 8.7 min (95% CI 7.4-10.7 min) for dimethyl-methoxycarbonyl metomidate (Table 1).

However in the cases of methoxycarbonyl metomidate and R-methyl-methoxycarbonyl metomidate, metabolism was so fast that their concentrations in blood could not be quantified using high performance liquid chromatography technique after 10 s, the shortest incubation time. Based on the lower limit of quantification, this indicates a metabolic half-life that is less than 2 s. For comparison, FIG. 5 also shows metabolism data for etomidate, which had a calculated metabolic half-life of 99 min (95% CI 81-126 min).

As with hypnotic potency, the rate of metabolism in blood was diastereometrically-selective. For example, the metabolic half-life of the S-isopropyl-methoxycarbonyl metomidate was two orders of magnitude longer than for its R form (Table 1). Similarly, the metabolic half-lives of S-methyl-methoxycarbonyl metomidate and α-S-methyl-methoxycarbonyl etomidate were at least four-fold longer than that of their respective R forms. Only in the case of β-methyl-methoxycarbonyl etomidate was there no significant difference in the metabolic half-lives of R and S forms. The current studies show that introducing aliphatic groups near methoxycarbonyl etomidate's labile ester moiety modifies the drug's in vitro rate of metabolism in rat blood and in vivo duration of action and hypnotic potency in rats. Furthermore, if the aliphatic group is placed immediately adjacent to the ester moiety's carbonyl group, the effects on in vitro metabolism and in vivo potency are diastereometrically-selective as each R form is metabolized in blood more quickly and has a hypnotic potency that is lower than its corresponding S form.

The structures of the etomidate esters described in this study are based on that of methoxycarbonyl etomidate, a soft analog of etomidate that contains a metabolically labile ester moiety that is linked to the etomidate ester via a simple two-carbon spacer.[12] We hypothesize that this spacer makes the ester labile primarily because it reduces the steric hindrance that interferes with drug-esterase binding. The metabolically labile ester is distinct from the existing ester moiety on etomidate which is attached directly to the rigid etomidate imidazole ring and is a relatively poor substrate for esterase-catalyzed hydrolysis as evidenced by the long (>1 hour) etomidate in vitro metabolic half-life in rat blood and human s9 liver fraction and several hour in vivo terminal elimination half-life in humans.[12,23,24]

TABLE 1

Pharmacodynamic and Pharmacokinetic Properties of Etomidate, Metomidate and Etomidate Esters.

| Structure Number | Name | ED50 ± SD mg/kg | Slope of Duration vs. Log Dose ± SD min/(log mg/kg) | Blood Half-Life (95% CI) min | Octanol/Water Partition Coefficient ± SD |
|---|---|---|---|---|---|
| 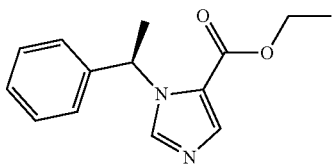 [SMILES: CCOC(=O)c1cncn1[C@H](C)c1ccccc1] | Etomidate | 0.53 ± 0.17 | 24.6 ± 4.7 | 99 (81-126) | 800 ± 180* |
| 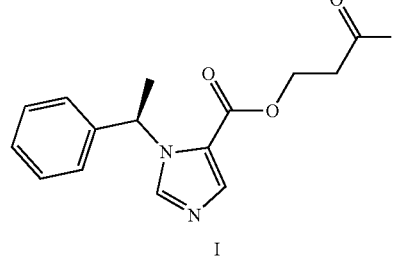 | Metomidate | 0.73 ± 0.50 | 33.0 ± 3.9 | 143 (124-170) | 380 ± 48 |
| 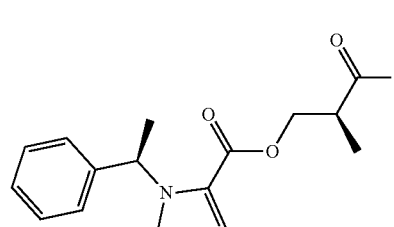 I | Methoxycarbonyl etomidate | 5.3 ± 1.5 | 1.0 ± 0.3 | 0.41 (0.31-0.60) | 190 ± 25 |
| 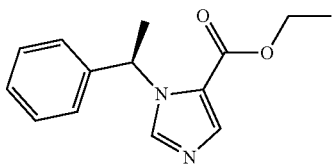 [SMILES: CCOC(=O)c1cncn1[C@H](C)c1ccccc1] II | α-(R)-methyl-methoxycarbonyl etomidate | 5.2 ± 0.5 | 2.6 ± 0.3 | 0.19 (0.17-0.22) | 670 ± 120 |
| 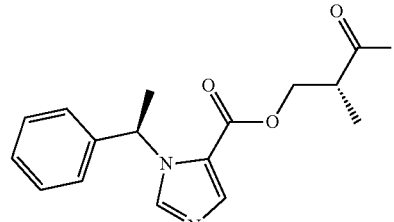 III | α-(S)-methyl-methoxycarbonyl etomidate | 3.1 ± 0.4 | 2.4 ± 0.3 | 0.76 (0.58-1.0) | 530 ± 170 |

TABLE 1-continued

Pharmacodynamic and Pharmacokinetic Properties of Etomidate, Metomidate and Etomidate Esters.

| Structure Number | Name | ED50 ± SD mg/kg | Slope of Duration vs. Log Dose ± SD min/(log mg/kg) | Blood Half-Life (95% CI) min | Octanol/Water Partition Coefficient ± SD |
|---|---|---|---|---|---|
| 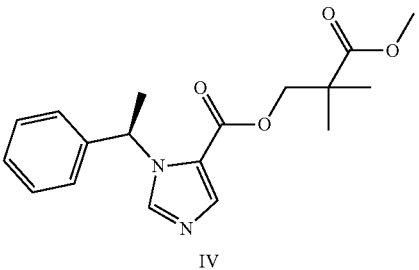 IV | α-dimethyl-methoxycarbonyl etomidate | 2.4 ± 1 | 9.8 ± 1.5 | 2.6 (1.9-4.2) | 2240 ± 150 |
| 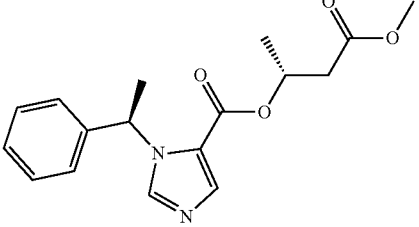 V | β-(R)-methyl-methoxycarbonyl etomidate | 3.5 ± 0.6 | 2.9 ± 0.8 | 0.91 (0.76-1.1) | 500 ± 24 |
| 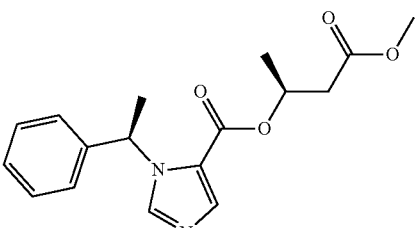 VI | β-(S)-methyl-methoxycarbonyl etomidate | 2.9 ± 0.3 | 2.0 ± 0.5 | 0.72 (0.56-0.98) | 484 ± 12 |
| 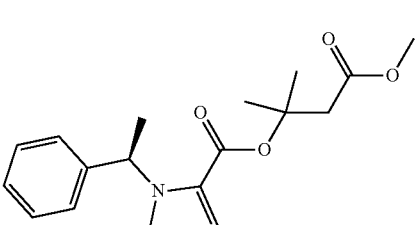 VII | β-dimethyl-methoxycarbonyl etomidate | 1.9 ± 0.3 | 11.9 ± 0.6 | 23.4 (19.6-28.9) | 1580 ± 40 |
| 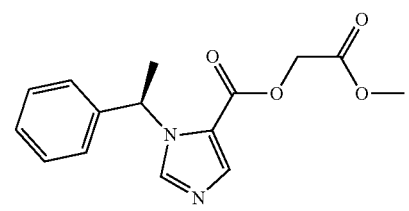 VIII | Methoxycarbonyl metomidate | 11.1 ± 0.8 | 1.6 ± 0.4 | <0.03 | 159 ± 15 |

TABLE 1-continued

Pharmacodynamic and Pharmacokinetic Properties of Etomidate, Metomidate and Etomidate Esters.

| Structure Number | Name | ED50 ± SD mg/kg | Slope of Duration vs. Log Dose ± SD min/(log mg/kg) | Blood Half-Life (95% CI) min | Octanol/Water Partition Coefficient ± SD |
|---|---|---|---|---|---|
| 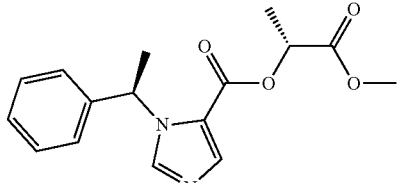 IX | (R)-methyl-methoxycarbonyl metomidate | 9.6 ± 1.9 | 4.6 ± 0.7 | <0.03 | 380 ± 15 |
| 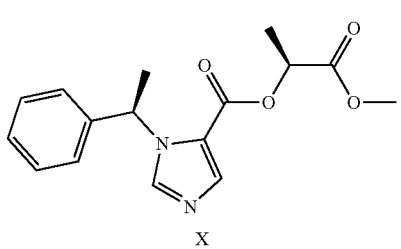 X | (S)-methyl-methoxycarbonyl metomidate | 3.5 ± 0.4 | 1.9 ± 0.2 | 0.14 (0.08-0.62) | 330 ± 16 |
| 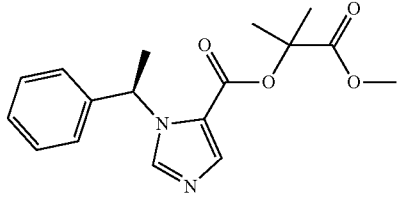 XI | Dimethyl-methoxycarbonyl metomidate | 0.72 ± 0.16 | 9.6 ± 0.8 | 8.7 (7.4-10.7) | 660 ± 110 |
| 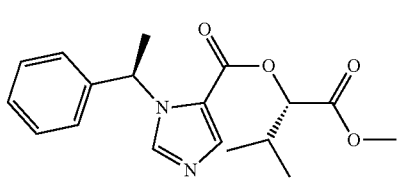 XII | (R)-isopropyl-methoxycarbonyl metomidate | 3.6 ± 0.8 | 6.6 ± 1.3 | 0.15 (0.15-0.16) | 3830 ± 310 |
| 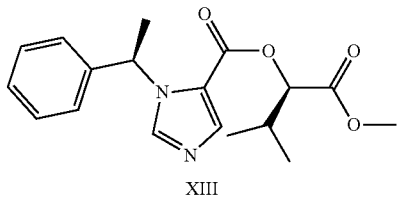 XIII | (S)-isopropyl-methoxycarbonyl metomidate | 1.2 ± 0.19 | 12.1 ± 1.1 | 15.5 (11.6-23.1) | 2860 ± 67 |
| 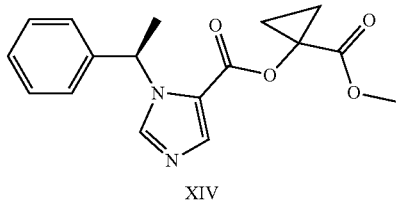 XIV | Cyclopropyl-methoxycarbonyl metomidate | 0.69 ± 0.04 | 6.9 ± 0.5 | 0.57 (0.49-0.68) | 420 ± 11 |

*From Pejo et al.[8]

In Vitro Metabolism in Rat Blood.

The inventors chose blood to measure the metabolic stabilities of the etomidate esters because rat blood has relatively high esterase activity and is thought to be an important (but not the exclusive) site of etomidate and methoxycarbonyl etomidate metabolism.[25,26] In order to reduce the rate of ester hydrolysis and prolong the duration of hypnotic action, the inventors added steric hindrance by adding aliphatic groups onto the two-carbon spacer of methoxycarbonyl etomidate. This strategy was based on previous studies showing that the presence of bulky chemical groups near metabolically labile ester moieties may slow the rate of ester hydrolysis.[15,27-29] In some cases the inventors also shortened the length of the spacer from two carbons to one, forming metomidate rather than etomidate analogs and found that this accelerated metabolism in rat blood. For example, the metabolic half-life of methoxycarbonyl etomidate in rat blood is 20 s whereas that of methoxycarbonyl metomidate is less than 2 s. Similarly, the metabolic half-lives of the R and S forms of α-R-methyl-methoxycarbonyl etomidate are at least four-fold longer than the respective R and S forms of R-methyl-methoxycarbonyl metomidate. This was contrary to what would normally be expected as the shorter spacer is predicted to introduce greater steric hindrance because it brings the labile ester closer to the rigid imidazole ring. However, the shorter spacer also reduces (to a single carbon) the distance between the carbonyl group of the labile ester moiety and the oxygen of the stable ester (FIG. 1). Such proximity can allow the oxygen atom, which is electronegative, to more effectively withdraw electron density from the carbonyl carbon and thus promote nucleophilic attack by esterases. This mechanism is thought to explain why a similarly located chlorine atom—which is also electronegative—increases the rate of acetate ester hydrolysis by 40-fold.[30]

The inventors also discovered that for three of the four diastereometric pairs, the R form was metabolized in rat blood significantly more quickly than the S form. The only diastereometric pair that failed to demonstrate high selectivity was methyl-methoxycarbonyl etomidate. This was also the only pair in which the aliphatic group is not located immediately adjacent to the labile ester moiety, suggesting that etomidate ester metabolism in blood is most stereoselective when the chiral center is closest to the ester. The stereoselective metabolism in blood that the inventors observed with the etomidate esters is reminiscent of (but larger than) that previously reported for esmolol.[31] In those studies, the blood from different species (e.g. rats and dogs) exhibited differential selectivity for the two enantiomers of esmolol and human blood exhibited no selectivity at all.

In Vivo Hypnotic Potency in Rats.

The addition of aliphatic groups onto the spacer increased etomidate ester hydrophobicity and altered in vivo etomidate ester hypnotic potency. However in violation of the Meyer-Overton Rule, increased hydrophobicity did not correlate with increased potency implying that the interactions between etomidate esters and their relevant molecular target (presumably the γ-aminobutyric acid receptor) are structurally specific. Analogous conclusions have previously been made for propofol analogs.[32] The data presented herein also suggests that hypnotic potency can be modestly diastereometrically-selective as all R forms of the etomidate esters had modestly lower hypnotic potencies than their respective S forms. Without wishing to be bound by a theory, this can result from their lower intrinsic potencies (i.e. potencies at the γ-aminobutyric acid receptor) or their faster metabolism. The latter can be important if ultra-rapid metabolism in blood lowers the concentration of drug that reaches the brain following bolus injection.

Unexpectedly, four compounds (dimethyl-methoxycarbonyl metomidate, cyclopropyl-methoxycarbonyl metomidate, cyclobutyl-methoxycarbonyl metomidate and cyclopentyl-methoxycarbonyl metomidate) had potencies that were nearly an order of magnitude higher than that of methoxycarbonyl etomidate and similar to that of etomidate. The first two of these compounds were also determined to possess in vitro metabolic half-lives intermediate between those of methoxycarbonyl etomidate and etomidate and all four compounds exhibited in vivo durations of action intermediate between those of methoxycarbonyl etomidate and etomidate.

Methoxycarbonyl etomidate is the prototypical rapidly metabolized etomidate analog; however, preliminary studies suggest that it may be too short acting for some clinical uses. The inventors hypothesized that the metabolism rate and duration of action of methoxycarbonyl etomidate could be systematically reduced and its clinical utility improved by incorporating specific aliphatic groups into the molecule to sterically protect its ester moiety from esterase-catalyzed hydrolysis. To test this hypothesis, the inventors designed, synthesized, and studied a series of methoxycarbonyl etomidate analogs (etomidate esters) containing various aliphatic protecting groups.

Etomidate esters were synthesized and their hypnotic potencies and durations of action following bolus administration were measured in rats using a loss of righting reflexes assay. Etomidate ester octanol:water partition coefficients and metabolic half-lives in pooled rat blood were determined chromatographically.

Etomidate esters produced hypnosis rapidly and in a dose-dependent manner. ED50s for loss of righting reflexes ranged from 0.69±0.04 mg/kg for cyclopropyl-methoxycarbonyl metomidate to 9.6±1.9 for R-methyl-methoxycarbonyl metomidate and did not correlate with octanol:water partition coefficients. The slope of a plot of the duration of loss of righting reflexes versus the logarithm of the etomidate ester dose ranged 12-fold among etomidate esters implying widely varying brain clearance rates. Etomidate ester in vitro metabolic half-lives varied by more than an order of magnitude and were diastereometrically-selective. Thus, addition of aliphatic protecting groups adjacent to the labile ester moiety of etomidate esters can be used to optimize their hypnotic potencies, durations of action, and rates of metabolism.

Accordingly, data presented in this study shows that addition of aliphatic groups adjacent to the labile ester moiety of etomidate esters can be used to optimize their hypnotic potencies, durations of action, and rates of metabolism. The introduction of aliphatic groups near an etomidate ester's metabolically-labile ester moiety modifies the drug's rate of metabolism in blood and duration of action and hypnotic potency in rats. Furthermore, the effects of these groups are enantiomerically-selective.

Example 2

Synthesis of Compounds
Preparation of Compound 8:

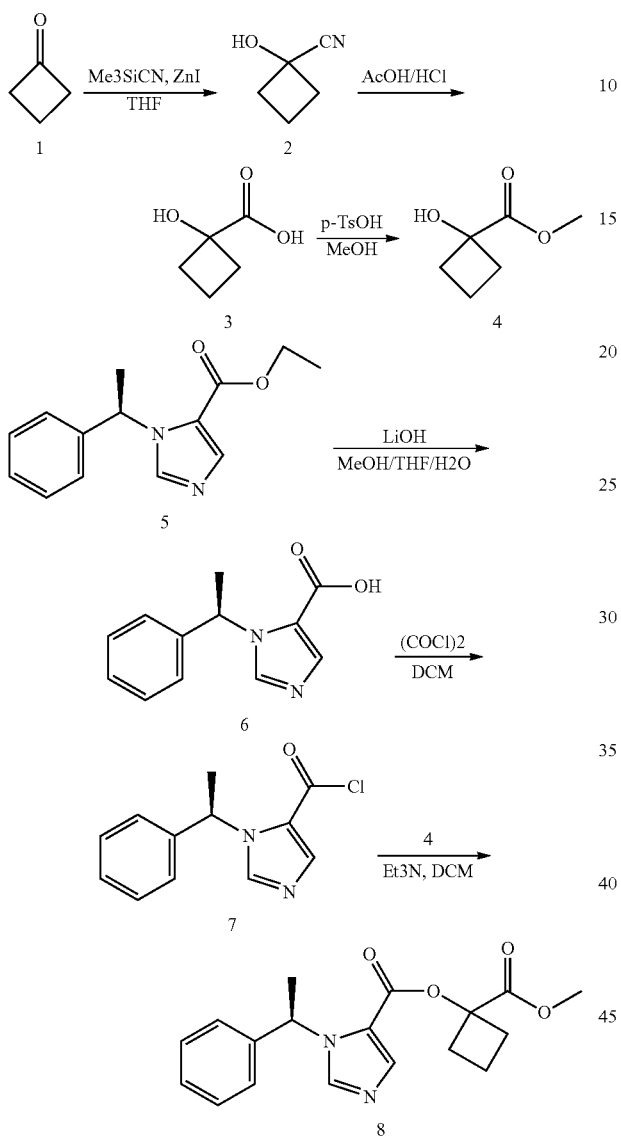

To a solution of 1 (700 mg, 10 mmol) in THF (50 mL) was added Me$_3$SiCN (1.39 g, 14 mmol) and ZnI (90 mg, 0.28 mmol). After stirring 24 h at RT, the reaction mixture was evaporated. The residue was diluted with EtOAc, washed with sat. NaHCO$_3$, water, brine, dried over Na$_2$SO$_4$, filtered, and concentrated. The residue was purified by silica gel column chromatography (hexane/EtOAc 10:1 to 3:1) to give 2 (530 mg, 55%).

A solution of 2 (533 mg, 5.5 mmol) in AcOH (25 mL) and conc. HCl (25 mL) was refluxed for 3 h. The reaction mixture was evaporated. The residue was purified by silica gel column chromatography (DCM/MeOH 20:1 to 5:1) to give 3 (510 mg, 80%).

A solution of 2 (500 mg, 4.3 mmol) in MeOH (10 mL) and p-TsOH (100 mg) was refluxed for 24 h. The reaction mixture was evaporated. The residue was purified by silica gel column chromatography (hexane/EtOAc 3:1) to give 4 (206 mg, 37%).

To a solution of 5 (12.2 g, 50 mmol) in MeOH/THF (1:1) (150 mL) was added aqueous LiOH (2N, 200 mL) at room temperature and the mixture was stirred overnight. After removal of MeOH/THF, the resulting aqueous phase was washed with ether, acidified with dilute HCl (pH=4), and extracted with dichloromethane. The combined organic extracts were washed with water, brine, and dried over Na$_2$SO$_4$, filtered, and concentrated. The residue was solidified and filtered to yield the corresponding acid 6 (10.8 g, 81%).

To a solution of 6 (285 mg, 1.32 mmol) in DCM (15 mL) was added (COCl)$_2$ (350 µL) at 0° C. drop-wise. The reaction mixture was stirred at room temperature until completion of the reaction monitored by HPLC. The reaction mixture was then concentrated and azeotroped by anhydrous toluene three times. The crude product 7 was dried on high vacuum pump for 3 h before use for the next step directly without storage.

To a solution of 7 from Step 5 (1.32 mmol) in DCM (20 mL) was added 4 (200 mg) in 5 mL of DCM followed by Et$_3$N (800 µL) at 0° C. The reaction mixture was stirred at room temperature for 48 h. The reaction mixture was diluted with EtOAc, washed with water, brine, dried over Na$_2$SO$_4$, filtered, and concentrated. The residue was purified by silica gel column chromatography (hexane/EtOAc 3:1 to 1:1) to give 8 (45 mg, 10.4%). LCMS ES$^+$ [M+1]=329. $^1$H NMR (400 MHz, CDCl3) δ 8.00 (S, 1H), 7.95 (s, 1H), 7.35-7.42 (m, 3H), 7.22-7.29 (m, 2H), 6.35 (q, J=7.2 Hz, 1H), 3.72 (s, 3H), 2.75-2.79 (m, 2H), 2.4-2.47 (m, 2H), 2.07-2.11 (m, 2H), 1.92 (d, J=7.2 Hz, 3H), 1.5-1.54 (m, 2H).

Preparation of Compound 9:

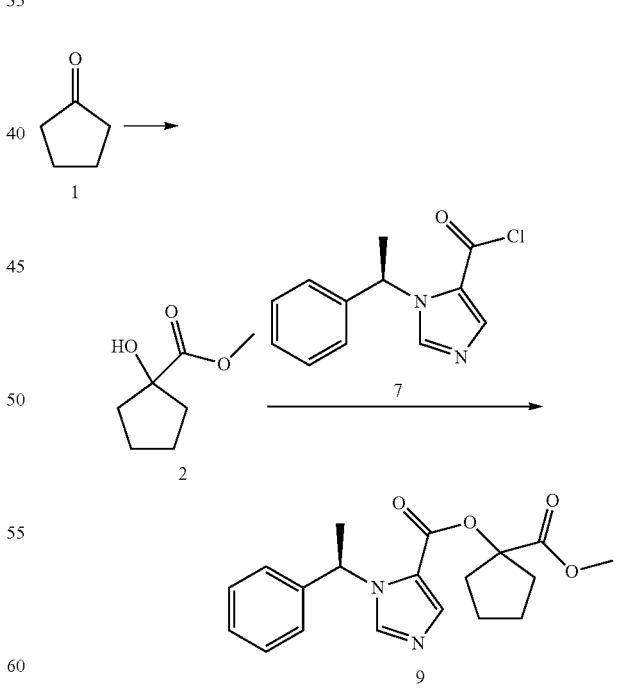

A solution of sodium metabisulfate (4.84 g, 0.025 mol) in distilled water (20 mL) was added over 45 min to a stirred mixture of cyclopentanone 1 (3.45 g, 0.041 mol), potassium cyanide (3.3 g, 0.051 mol), and water (20 mL). The mixture was stirred at 25° C. for 6 hrs. The mixture was extracted with ethyl acetate (2×100 mL) and the organics dried (MgSO$_4$), and concentrated to give 3.6 g of α-hydroxycyclopentanecarbonitrile as an oil. The oil was dissolved in acetic acid (12.5 mL) and the solution was diluted with concentrated HCl (37.5 mL). The solution was refluxed for 3 hrs and concentrated to an oily residue that was partitioned between water (50 mL) and EtOAc (50 mL). The organic phase was separated, dried (MgSO$_4$), and concentrated to an oily residue which solidified on standing to give 4.1 g of α-hydroxycyclopentanecarboxylic acid. This material was dissolved in MeOH (50 mL) and treated with concentrated sulfuric acid (1 drop). The solution was refluxed for 12 hrs and concentrated to an oily residue which was dissolved in EtOAc (50 mL) and washed with a 5% solution of sodium bicarbonate (50 mL). The organics were dried (MgSO$_4$), filtered, concentrated, and chromatographed on silica gel (80% Hexanes/20% EtOAc) to give α-hydroxycyclopentanecarboxylic acid methyl ester 2 (3.66 g) as an clear colorless oil.

A solution of 2 (265 mg, 1.8 mmol) in dry pyridine (10 mL) was heated to 80° C. and a solution of 3 (243 mg, 0.9 mmol) in anhydrous dichloromethane (10 mL) was dropwise added over a 1 hour period using a syringe pump. The resulting suspension was evaporated and diluted with 1N HCl (30 mL) and EtOAc (50 mL). The organics were dried (MgSO$_4$), filtered, and concentrated to give an oily residue which was chromatographed on silica gel (60% Hexanes/40% EtOAc) to give 9 as an oil: (140 mg). $^1$HNMR (400 MHz, CDCl$_3$): δ 1.71-1.79 (4H, m), 1.81-1.91 (3H, d, J=3.1 Hz), 2.01-2.17 (2H, m), 2.19-2.39 (2H, m), 3.61 (3H, s), 6.27 (1H, m), 7.13-7.19 (2H, m), 7.22-7.37 (3H, m), 7.72 (1H, s), 7.81 (1H, s). LCMS (mobile phase: 2%-98% Acetonitrile-Water—0.1% Formic acid): purity is >95%, Rt=2.5 min; MS Calcd.: 342; MS Found: 343 (M+1).

Preparation of Compound 10:

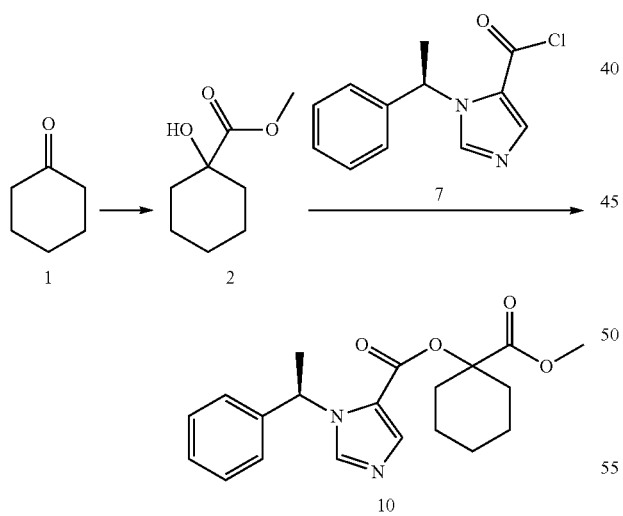

A solution of sodium metabisulfate (4.84 g, 0.025 mol) in distilled water (20 mL) was added over 30 min to a stirred mixture of cyclohexanone 1 (4.02 g, 0.041 mol), potassium cyanide (3.3 g, 0.051 mol), and water (20 mL). The mixture was stirred at 25° C. for 8 hrs. The mixture was extracted with ethyl acetate (2×100 mL) and the organics dried (MgSO$_4$), and concentrated to give 3.8 g of α-hydroxycyclohexanecarbonitrile as an oil. The oil was dissolved in acetic acid (12.5 mL) and the solution was diluted with concentrated HCl (37.5 mL). The solution was refluxed for 6 hours and concentrated to an oily residue that was partitioned between water (50 mL) and EtOAc (50 mL). The organic phase was separated, dried (MgSO$_4$), and concentrated to a solid. The solid was washed with hexanes (25 mL) and filtered to give 2.84 g of α-hydroxycyclohexanecarboxylic acid. This material was dissolved in MeOH (50 mL) and treated with concentrated sulfuric acid (1 drop). The solution was refluxed for 16 hours and concentrated to an oily residue which was dissolved in EtOAc (50 mL) and washed with a 5% solution of sodium bicarbonate (50 mL). The organics were dried (MgSO$_4$), filtered, concentrated, and chromatographed on silica gel (80% Hexanes/20% EtOAc) to give α-hydroxycyclohexanecarboxylic acid methyl ester 2 (2.71 g) as an clear colorless oil.

A solution of 2 (350 mg, 2.2 mmol) in dry pyridine (10 mL) was heated to 80° C. and a solution of 7 (300 mg, 1.1 mmol) in anhydrous dichloromethane (10 mL) was added drop-wise over a 1-hour period using a syringe pump. The resulting suspension was evaporated and diluted with 1N HCl (30 mL) and EtOAc (50 mL). The organics were dried (MgSO$_4$), filtered, and concentrated to give an oily residue which was chromatographed on silica gel (60% Hexanes/40% EtOAc) to give 10 as an oil: (161 mg). $^1$HNMR (400 MHz, CDCl$_3$): δ 1.21-1.38 (2H, m), 1.42-1.78 (4H, m), 1.79-1.85 (1H, m), 1.85 (3H, d, J=2.7 Hz), 3.05-3.28 (3H, m), 3.58 (3H, s), 6.25 (1H, m), 7.13-7.18 (2H, m), 7.23-7.39 (3H, m), 7.71 (1H, s), 7.82 (1H, s). LCMS (mobile phase: 2%-98% Acetonitrile-Water—0.1% Formic acid): purity is >95%, Rt=2.1 min; MS Calcd.: 356; MS Found: 357 (M+1).

Preparation of Compound 11:

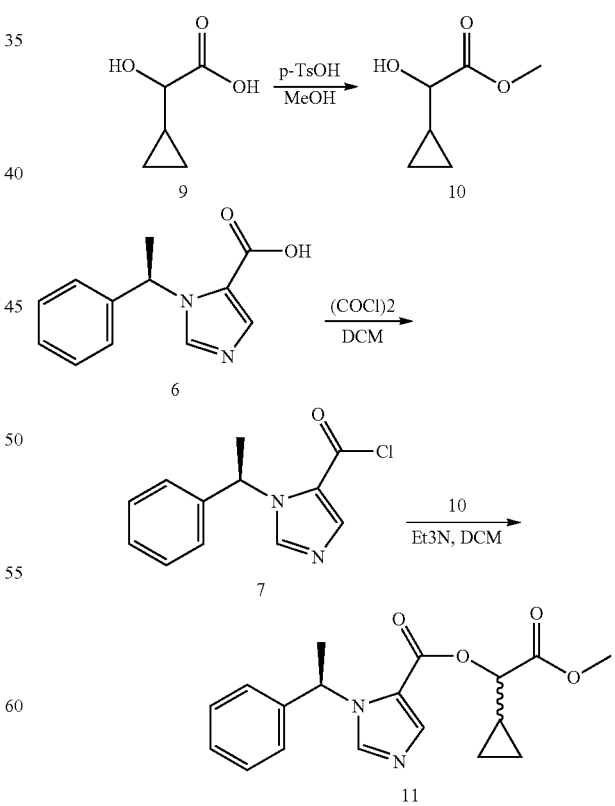

A solution of 9 (500 mg, 4.3 mmol) in MeOH (10 mL) and p-TsOH (100 mg) was refluxed for 24 h. The reaction mixture was evaporated. The residue was purified by silica gel column chromatography (hexane/EtOAc 3:1) to give 10 (182 mg, 33%).

To a solution of 6 (216 mg, 1 mmol) in DCM (15 mL) was added (COCl)$_2$ (150 µL) at 0° C. drop-wise. The reaction mixture was stirred at room temperature until completion of the reaction monitored by HPLC. The reaction mixture was then concentrated and azeotroped by anhydrous toluene three times. The crude product 7 was dried on high vacuum pump for 3 h before use for the next step directly without storage.

To a solution of 7 from Step 5 (1 mmol) in DCM (15 mL) was added 10 (156 mg, 1.2 eq) in 5 mL of DCM followed by Et3N (400 µL) at 0° C. The reaction mixture was stirred at room temperature overnight. The reaction mixture was diluted with EtOAc, washed with water, brine, dried over Na$_2$SO$_4$, filtered, and concentrated. The residue was purified by silica gel column chromatography (hexane/EtOAc 3:1 to 1:1) to give 11 (203 mg, 61%). LCMS ES$^+$ [M+1]=329.

Preparation of Compound 12:

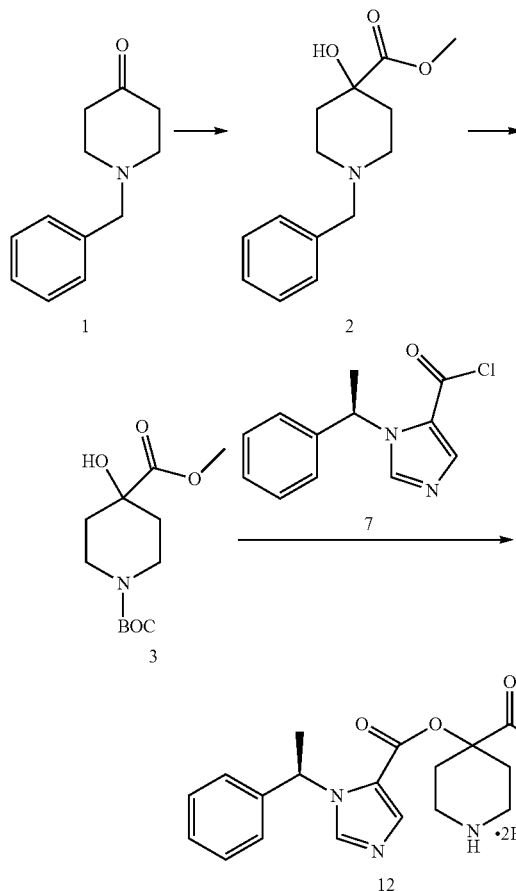

and the solution was diluted with concentrated HCl (75 mL). The solution was refluxed for 3 hours and concentrated to a solid mass. Toluene (100 mL) was added to the solid mass and the mixture was evaporated. This process was repeated one additional time. The resulting solid was then diluted with MeOH (100 mL) and treated with concentrated sulfuric acid (3.4 g). The solution was refluxed for 12 hours and concentrated to an oily residue which was diluted with a saturated solution of sodium bicarbonate (100 mL) and then extracted with EtOAc (2×100 mL). The organics were dried (MgSO$_4$), filtered, concentrated, and chromatographed on silica gel (60% hexanes/40% EtOAc) to give 2 (11.2 g) as an amber oil.

This oil 2 (11.2 g) was dissolved in MeOH (40 mL), treated with Pd—C (5%, 1.5 g), acetic acid (2.7 g), and then shaken under 50 psi hydrogen for 2 hours. The suspension was filtered through a pad of celite and concentrated to an oily residue. The oil was dissolved in EtOAc (50 mL), and the solution was treated with a saturated solution of sodium bicarbonate (50 mL). The mixture was vigorously stirred and di-tert-butyl dicarbonate (19.6 g, 90 mmol) was added drop-wise as a solution in EtOAc (20 mL). The mixture continued stirring for 2 hours and the organics were separated, concentrated, and chromatographed on silica gel to give 11 g of 3 as an oil.

A solution of 3 (1.5 g, 5.8 mmol) in dry pyridine (25 mL) was heated to 80° C. and a solution of 3 (1 g, 3.6 mmol) in anhydrous dichloromethane (25 mL) was added drop-wise over a 2 hour period using a syringe pump. The resulting suspension was evaporated and diluted with 1N HCl (30 mL) and EtOAc (50 mL). The organics were dried (MgSO$_4$), filtered, and concentrated to give an oily residue which was chromatographed on silica gel (60% Hexanes/40% EtOAc) to give an oil which was dissolved in EtOAc (5 mL) and the resulting solution added to a vigorously stirred solution of HCl in dioxane (4N, 3 mL). The suspension was stirred for 1 hour at RT and the solid filtered, washed with ether and dried to give 12 as the dihydrochloride salt, a white solid (850 mg). $^1$HNMR (400 MHz, DMSO): δ 1.85 (3H, d, J=2.9 Hz), 2.01-2.25 (4H, m), 2.96-3.27 (4H, m), 3.47 (3H, s), 6.21 (1H, m), 7.18-7.22 (2H, m), 7.23-7.41 (3H, m), 8.61 (1H, s), 9.31 (1H, s). LCMS (mobile phase: 2%-98% Acetonitrile-Water—0.1% Formic acid): purity is >99%, Rt=0.66 min; MS Calcd.: 357; MS Found: 358 (M+1).

Preparation of Compound 13:

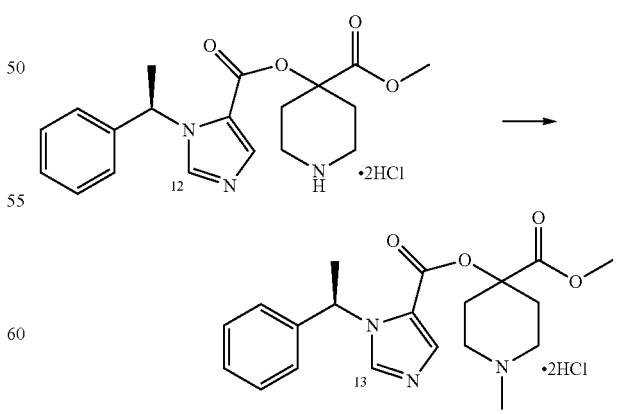

A solution of sodium metabisulfate (14.5 g, 0.075 mol) in distilled water (60 mL) was added over 2 h to a stirred mixture of 1 (23.2 g, 123 mmol), potassium cyanide (9.9 g, 153 mmol), and water (60 mL). The mixture was stirred at 25° C. for 5 hours. The mixture was extracted with ethyl acetate (2×100 mL) and the organics dried (MgSO$_4$), and concentrated to give an oil which slowly solidified on standing at RT. The waxy solid was triturated with hexanes-ether (9:1) and filtered to give 14.9 g of the corresponding cyanohydrin. This solid was dissolved in acetic acid (25 mL)

To a solution of 12 dihydrochloride (500 mg, 1.2 mmol) in CH$_3$CN (5 mL) was added paraformaldehyde (360 mg, 12 mmol) and the suspension was allowed to stir for 30 minutes. NaCNBH$_3$ (189 mg, 3 mmol) was then added and the resultant mixture was stirred for 2 hours. The solution was diluted with EtOAc (50 mL) and washed with a saturated sodium bicarbonate solution (100 mL). The organics were washed with water (50 mL) and brine (50 mL) and then dried (MgSO$_4$), filtered, concentrated, and chromatographed on silica gel (EtOAc) to give 107 mg of 13 as an oil. This material was dissolved in EtOAc (2 mL) and added drop-wise to a stirred solution of HCl in dioxane (4N, 1 mL). The suspension was stirred for 1 hour and the solids were filtered and dried to give 98 mg of 13 as the dihydrochloride. $^1$HNMR (400 MHz, DMSO): δ 1.91 (3H, d, J=1.7 Hz), 2.19-2.41 (4H, m), 2.76 (3H, d, J=1.2 Hz), 3.05-3.26 (2H, m), 3.28-3.61 (2H, m), 3.49 (3H, s), 6.23 (1H, m), 7.21-7.24 (2H, m), 7.25-7.39 (3H, m), 8.49 (1H, s), 9.31 (1H, s). LCMS (mobile phase: 2%-98% Acetonitrile-Water—0.1% Formic acid): purity is >98%, MS Calcd.: 371; MS Found: 372 (M+1).

Preparation of Compound 14:

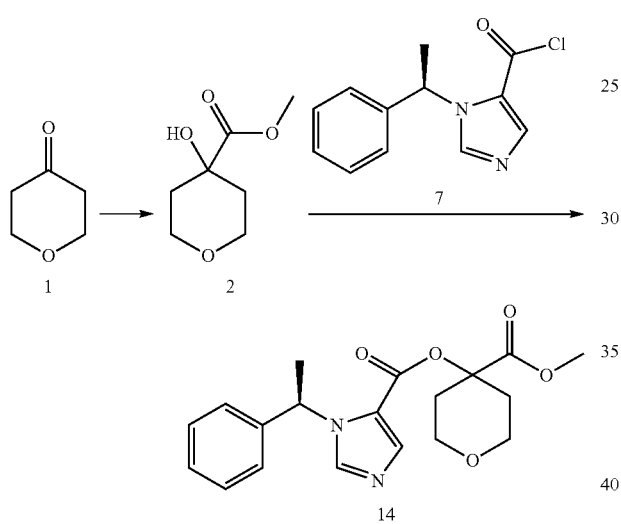

To a chilled solution (0° C.) of NaCN (25 g, 500 mmol) in water (75 mL) was added drop-wise via syringe pump a solution of 1 (5 g, 50 mmol) in concentrated HCl (450 g) over the course of 2 hours keeping the temperature at 0° C. The resulting solution was allowed to stir for an additional 16 hours at RT and the pH was adjusted to 4 using concentrated HCl. The resulting suspension was extracted with ether (3×100 mL). The organics were combined, washed with a saturated sodium bicarbonate solution, dried (MgSO$_4$), filtered, and concentrated to an oil, which was dissolved in acetic acid (25 mL) and diluted with concentrated HCl (75 mL). The solution was refluxed for 6 hours and concentrated to an oily residue that was partitioned between water (100 mL) and EtOAc (100 mL). The organic phase was separated, washed with a sodium bicarbonate solution (5%), dried (MgSO$_4$), and concentrated to an oily residue which was dissolved in MeOH (50 mL) and treated with concentrated sulfuric acid (3 drops). The solution was refluxed for 12 hours and concentrated to an oily residue which was dissolved in EtOAc (50 mL) and washed with a 5% solution of sodium bicarbonate (50 mL). The organics were dried (MgSO$_4$), filtered, concentrated, and chromatographed on silica gel (70% hexanes/30% EtOAc) to give 2 (2.8 g) as a clear colorless oil.

A solution of 2 (500 mg, 3.1 mmol) in dry pyridine (15 mL) was heated to 80° C. and a solution of 7 (423 mg, 1.6 mmol) in anhydrous dichloromethane (15 mL) was added drop-wise over 1 hour using a syringe pump. The resulting suspension was evaporated and diluted with 1N HCl (50 mL) and EtOAc (80 mL). The organics were dried (MgSO$_4$), filtered, and concentrated to give an oily residue which was chromatographed on silica gel (60% hexanes/40% EtOAc) to give 14 as an oil: (330 mg). $^1$HNMR (400 MHz, CDCl$_3$): δ 1.82 (3H, d, J=5.2 Hz), 2.00-2.27 (4H, m), 3.58 (3H, s), 3.61-3.94 (4H, m), 6.25 (1H, m), 7.13-7.19 (2H, m), 7.21-7.39 (3H, m), 7.78 (1H, s), 7.82 (1H, s). LCMS (mobile phase: 2%-98% Acetonitrile-Water—0.1% Formic acid): purity is >95%, Rt=3.1 min; MS Calcd.: 358; MS Found: 359 (M+1).

Preparation of Compound 16:

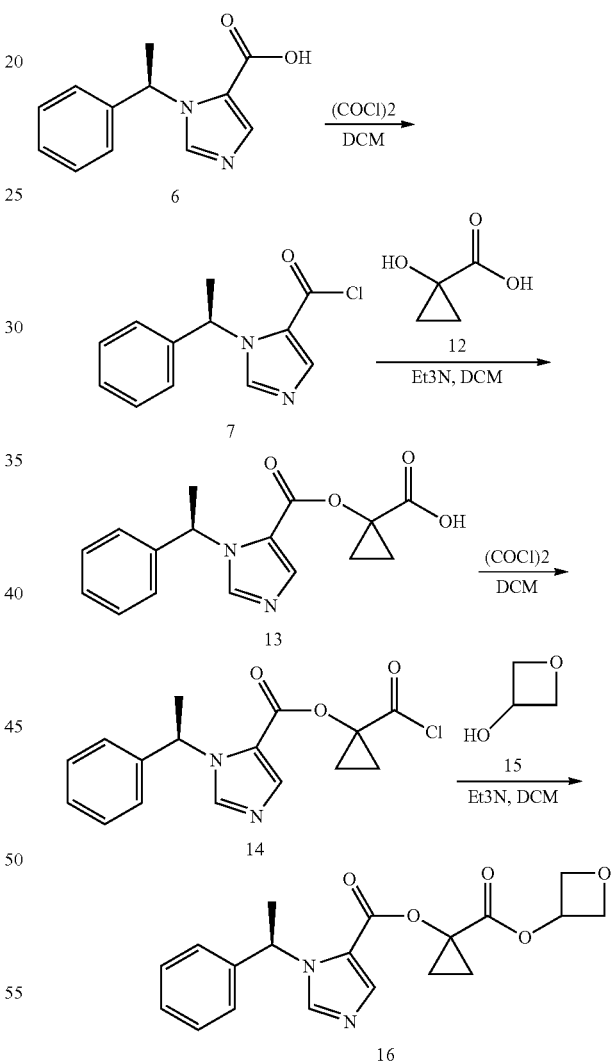

To a solution of 6 (648 mg, 3 mmol) in DCM (50 mL) was added (COCl)$_2$ (400 µL) at 0° C. drop-wise. The reaction mixture was stirred at room temperature until completion of the reaction monitored by HPLC. The reaction mixture was then concentrated and azeotroped by anhydrous toluene three times. The crude product 7 was dried on high vacuum pump for 3 h before use for the next step directly without storage.

To a solution of 7 from Step 5 (3 mmol) in DCM (50 mL) was added 12 (203 mg, 1 eq) followed by Et₃N (400 μL) at 0° C. The reaction mixture was stirred at room temperature overnight. The reaction mixture was diluted with EtOAc, washed with water, brine, dried over Na₂SO₄, filtered, and concentrated. The residue was purified by silica gel column chromatography (hexane/EtOAc 1:1 to 0:1) to give 13 (375 mg, 42%).

To a solution of 13 (250 mg, 0.83 mmol) in DCM (5 mL) was added (COCl)₂ (100 μL) at 0° C. drop-wise. The reaction mixture was stirred at room temperature until completion of the reaction monitored by HPLC. The reaction mixture was then concentrated and azeotroped by anhydrous toluene three times. The crude product 14 was dried on high vacuum pump for 3 h before use for the next step directly without storage.

To a solution of 14 from Step 3 (0.83 mmol) in DCM (10 mL) was added 15 (20 mg) followed by Et₃N (100 μL) at 0° C. The reaction mixture was stirred at room temperature overnight. The reaction mixture was diluted with EtOAc, washed with water, brine, dried over Na₂SO₄, filtered, and concentrated. The residue was purified by silica gel column chromatography (hexane/EtOAc 1:1 to 0:1) to give 16 (65 mg, 22%). LCMS ES⁺ [M+1]=366. ¹H NMR (400 MHz, CDCl3) δ 7.98 (s, 1H), 7.90 (s, 1H), 7.35-7.41 (m, 3H), 7.20-7.29 (m, 2H), 6.37 (q, J=6.8 Hz, 1H), 5.32-5.46 (m, 1H), 4.81-4.85 (m, 2H), 4.48-4.51 (m, 2H), 1.92 (d, J=6.8 Hz, 3H), 1.6-1.67 (m, 2H), 1.32-1.35 (m, 2H).

Preparation of Compound 20.

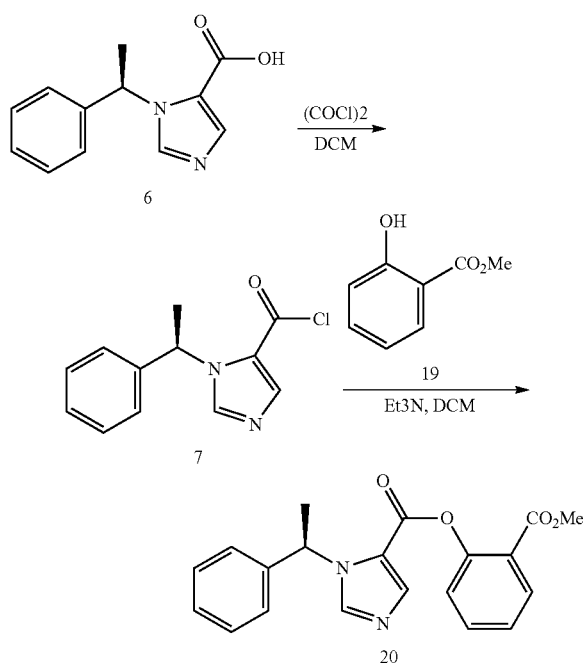

To a solution of 6 (216 mg, 1 mmol) in DCM (15 mL) was added (COCl)₂ (150 μL) at 0° C. drop-wise. The reaction mixture was stirred at room temperature until completion of the reaction monitored by HPLC. The reaction mixture was then concentrated and azeotroped by anhydrous toluene three time. The crude product 7 was dried on high vacuum pump for 3 h before use for the next step directly without storage.

To a solution of 7 from Step 1 (1 mmol) in DCM (15 mL) was added 19 (117 μL) in 5 mL of DCM followed by Et₃N (420 μL) at 0° C. The reaction mixture was stirred at room temperature overnight. The reaction mixture was diluted with EtOAc, washed with water, brine, dried over Na₂SO₄, filtered, and concentrated. The residue was purified by silica gel column chromatography (hexane/EtOAc 3:1 to 1:1) to give 20 (265 mg, 88%). LCMS ES⁺ [M+1]=301. ¹H NMR (400 MHz, CDCl3) δ 7.98 (s, 1H), 7.90 (s, 1H), 7.35-7.41 (m, 3H), 7.20-7.29 (m, 2H), 6.37 (q, J=6.8 Hz, 1H), 5.32-5.46 (m, 1H), 4.81-4.85 (m, 2H), 4.48-4.51 (m, 2H), 1.92 (d, J=6.8 Hz, 3H), 1.6-1.67 (m, 2H), 1.32-1.35 (m, 2H).

In Vivo Testing

Animals:

Animals were housed in a dedicated room at the vivarium of VivoPath Inc., located at Redstone Center, 55 Union Street, Worcester, Mass. Housing and care was as specified in the USDA Animal Welfare Act (9 CFR, Parts 1, 2, and 3) and as described in the *Guide for the Care and Use of Laboratory Animals* from the National Research Council. Environmental conditions of housing rooms are set at the following ranges: temperature: 70±7° F. (22±4° C.), humidity: 50±20%, light cycle: 12-hour light/12-hour dark cycle—lights on at 7 am and off at 7 pm., air changes: ten or more air changes per hour with 100% fresh air. The animals' body weights were measured prior to the first dose on each experimental day.

Mice:

Adult ICR mice (20-30 g) were purchased from Harlan (South Easton, Mass.). Drugs were administered as intravenous bolus injection in a tail vein.

Rats:

Adult male Sprague-Dawley rats (225-300 g) were purchased from Harlan (South Easton, Mass.). Drugs were administered as an intravenous bolus injection through a jugular venous catheter pre-implanted by the vendor prior to animal delivery to the animal care facility.

Drug Testing:

Drugs were prepared in either dimethylsulfoxide/saline or saline vehicle or hydroxypropyl-β-cyclodextrin (20% in water, pH 7.0) solution and were administered as an intravenous bolus injection. Animals received 1-4 doses of drug(s) during an experimental day, either ascending doses or different drugs. Doses were administered at intervals equal to the longer of 1 h or 10-times the duration of apparent sedative/hypnotic effects from the previous dose. The sedative/hypnotic properties of the drugs were evaluated by observation of the rats, ranging from mild excitation, mild sedation apparent due to reduced activity, and moderate sedation to hypnosis reflected by loss of righting reflex (LORR, the ability to place rear and hind legs under the body, as well as attenuation/loss of nociceptive reflexes).

Figure 6:
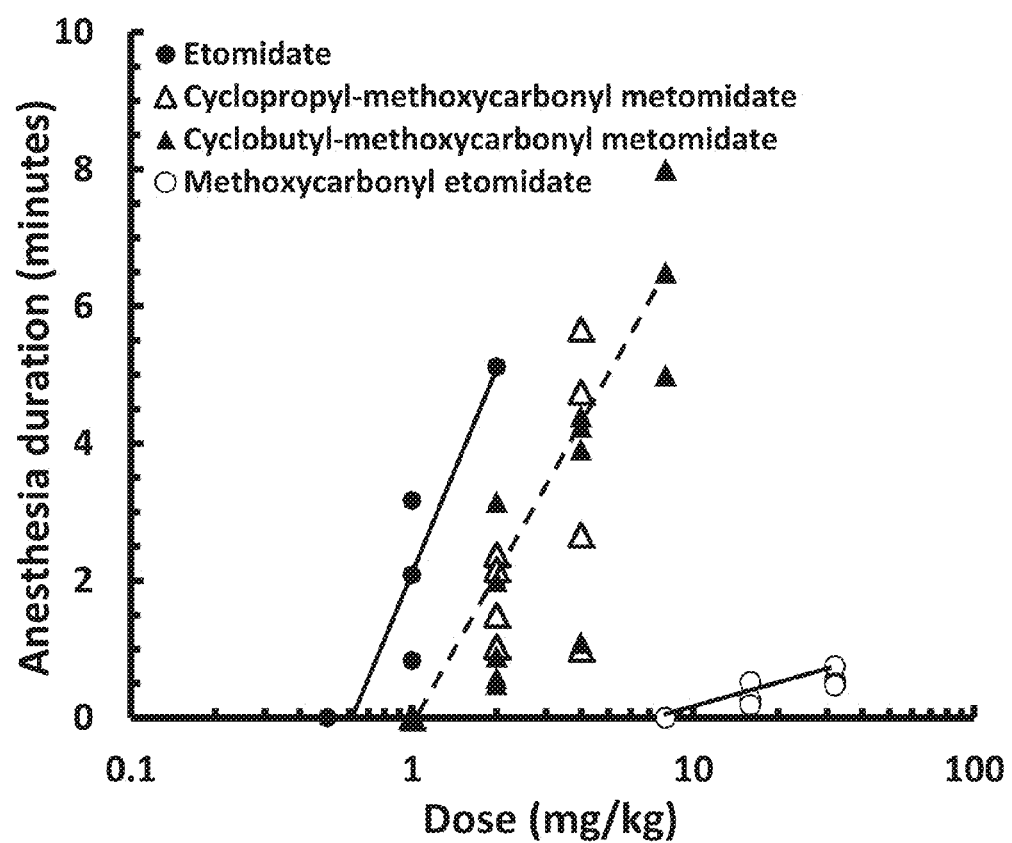
FIG. 6 shows duration of anesthesia as a function of amount of etomidate analogue administered in mouse.
Figure 7:
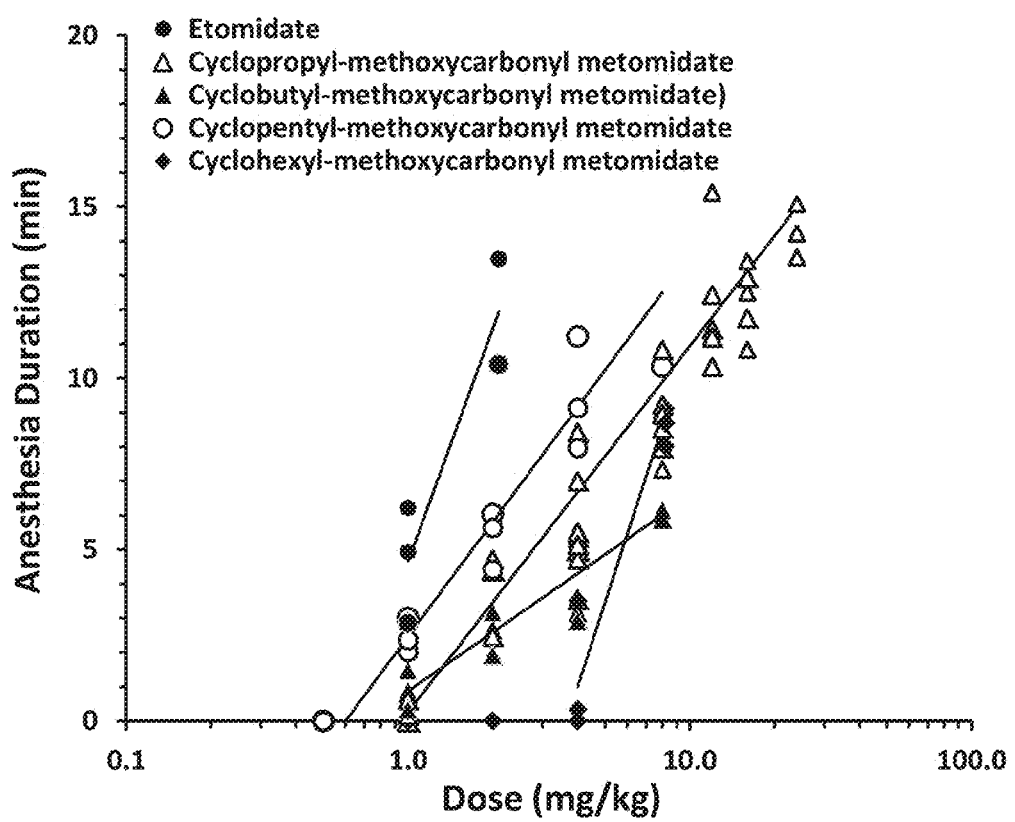
FIG. 7 shows duration of anesthesia as a function of amount of etomidate analogue administered in rat.

Results:

The results of the in vivo testing of representative novel etomidate analogues are shown in Table 2, below, and illustrated in FIGS. 6 and 7, in comparison with etomidate and other analogues. For representative etomidate esters FIGS. 6 and 7 plot the duration of LORR as a function of etomidate ester dose on a semi-logarithmic scale in mice and rats, respectively. They demonstrate that the duration of LORR increased approximately linearly with the logarithm of the etomidate ester dose. The slope of this relationship was approximately 1.0 for methoxycarbonyl-etomidate in both mice and rats. For etomidate, the slope was approximately 10 in mice and 24 in rats. Cyclopropyl-MOCmetomidate exhibited intermediate dose-dependency, with slope approximately 7 in mice and 10 in rats. Cyclobutyl-MOC-metomidate exhibited similar dose-dependency, with slope approximately 7 in mice and 5 in rats.

TABLE 2

| Structure | Mouse response | Rat response |
| --- | --- | --- |
| [structure: phenyl-ethyl-imidazole-carboxylate-cyclopropyl-carboxylate-oxetanyl] | No effect at 4 mg/kg IV | Not tested |
| [structure: phenyl-ethyl-imidazole-carboxylate-phenyl-methyl ester] | Mild excitation but no sedation at 2, 4 or 8 mg/kg IV | Not tested |
| [structure: phenyl-ethyl-imidazole-carboxylate-cyclobutyl-methyl ester] | Sedation/hypnosis induced at 2, 4 & 8 mg/kg IV<br>$ED_{50}$ ~1-2 mg/kg<br>See FIG. 6 | Sedation/hypnosis induced at 1, 2, 4 & 8 mg/kg IV<br>$ED_{50}$ ~1 mg/kg<br>See FIG. 7 |
| [structure: Me-phenyl-ethyl-imidazole-carboxylate-cyclopentyl-OMe] | Not tested | Sedative at 1 & 2 mg/kg, with rear paws out but head and forepaws mobile<br>Hypnotic at 4 & 8 mg/kg, quite long-acting |
| [structure: Me-phenyl-ethyl-imidazole-carboxylate-cyclohexyl-OMe] | Not tested | Mildly sedative at 4 mg/kg<br>Hypnotic at 8 mg/kg - deep and long-acting |
| [structure: Me-phenyl-ethyl-imidazole-carboxylate-piperidinyl(NH)-OMe] | Not tested | No effect apparent at 4, 8 & 16 mg/kg |
| [structure: Me-phenyl-ethyl-imidazole-carboxylate-N-methylpiperidinyl-OMe] | Not tested | No effect apparent at 4, 8 & 16 mg/kg |

TABLE 2-continued

| Structure | Mouse response | Rat response |
|---|---|---|
| (structure with Me, phenyl, imidazole, ester, tetrahydropyran, OMe) | Not tested | Mildly sedative at 16 mg/kg<br>More profound short-acting sedation at 32 mg/kg |
| (structure with phenyl, imidazole, ester, cyclopropyl, OMe) | Sedation/hypnosis induced at 8, 16 & 32 mg/kg IV<br>$ED_{50}$ ~8 mg/kg | Not tested |
| Etomidate<br>(structure) | Sedation/hypnosis induced at 2 & 4 mg/kg IV<br>$ED_{50}$ ~0.7 mg/kg<br>See FIG. 6 | Sedation/hypnosis induced at 2 & 4 mg/kg IV<br>$ED_{50}$ ~0.7 mg/kg<br>See FIG. 7 |
| MOC-etomidate<br>(structure) | Sedation/hypnosis induced at 16 & 32 mg/kg IV<br>$ED_{50}$ ~10 mg/kg<br>See FIG. 6 | Sedation/hypnosis induced at 8 & 16 mg/kg IV<br>$ED_{50}$ ~8 mg/kg<br>See FIG. 7 |
| Cyclopropyl-MOC-metomidate<br>(structure) | Sedation/hypnosis induced at 2 & 4 mg/kg IV<br>$ED_{50}$ ~0.7 mg/kg<br>See FIG. 6 | Sedation/hypnosis induced at 2 & 4 mg/kg IV<br>$ED_{50}$ ~0.7 mg/kg<br>See FIG. 7 |

Cyclopropyl-MOC-Metomidate—Various In Vitro and In Vivo Assessments

Cyclopropyl-MOC-metomidate induces anesthesia by acting as a positive allosteric modulator of the γ-aminobutyric acid (GABA) type A ($GABA_A$) receptor. Cyclopropyl-MOC-metomidate and its principle metabolite, CPM-acid, were evaluated for their ability to potentiate activation of $GABA_A$ receptor current in *Xenopus* oocytes expressing the human $α_1$(L264T), $β_2$ and $γ_{2L}$ subunits of the $GABA_A$ receptor using established methods (Ge et al., 2011). The $α_3$(L264T)$β_2γ_{2L}$ mutant was used rather than wild-type $GABA_A$ receptor because it is directly activated by anesthetics, allowing a simpler assessment of the drug potency without the need for concomitant activation by GABA. Anesthetic potency on this mutated $GABA_A$ receptor is similar to that on wild-type receptors. Currents were recorded using conventional 2-electrode voltage clamp technique at a holding potential of −50 mV. Oocytes were placed in a 0.04-mL recording chamber and constantly perfused at a rate of 4-6 mL/min. The current response to ABP-700 or CPM-acid was normalized to that produced by 100 μM GABA in the same oocyte and data presented as mean±SD from 3-6 oocytes.

Cyclopropyl-MOC-metomidate enhanced GABA-induced current having minimal effects at ~0.3 μM and an $EC_{50}$ value of 5.8±1.1 μM. CPM-acid was ~1000-fold less potent, having minimal effects at ~100 μM and an $EC_{50}$ value extrapolated to be near 14 mM. The range of plasma cyclopropyl-MOC-metomidate concentrations associated with anesthesia is ~0.2-3 μM, corresponding to ~$EC_{5-40}$ values observed in the oocyte GABA current.

Cyclopropyl-MOC-metomidate (10 μM) was screened for its ability to inhibit radioligand binding in assays of 68 receptors, ion channels and transporters. No significant effect of cyclopropyl-MOC-metomidate was observed. Binding of each radioligand to its receptor was inhibited no more than 25%. Of note, cyclopropyl-MOC-metomidate had no effect on the binding of either [$^3$H]-flunitrazepam (a benzodiazepine) or [$^3$H]-muscimol (a $GABA_A$ receptor agonist) to the $GABA_A$ receptor channel.

Cyclopropyl-MOC-metomidate was administered to rats as an IV bolus at doses of 0.25, 0.5, 1, 2, 4, 8, 16 or 24 mg/kg. Rats were monitored for anesthesia as assessed by loss of righting reflex (LORR) and the subsequent time to recovery from LORR. Bolus doses of 1.0 mg/kg and greater induced dose-dependent anesthesia. The minimum effective bolus anesthetic dose in rats was approximately 1 mg/kg based on LORR observations. Time to recovery from LORR was dose-dependent. A bolus dose of 4 mg/kg induced 3-8 minutes of anesthesia and LORR and was selected as an effective and convenient induction dose to precede continuous infusion dosing.

Cyclopropyl-MOC-metomidate anesthesia in rats by continuous infusion without a bolus induction dose was examined in this study. An infusion of 4 mg/kg induced anesthesia after approximately 3 minutes as measured by LORR. Recovery of righting reflex took approximately 4 minutes following infusion discontinuation whether the infusion was conducted for 5 or 120 minutes. Due to the prolonged onset of anesthesia, continuous infusion for anesthesia induction in rats was judged to be suboptimal for most experimental circumstances, and all subsequent studies were conducted using a bolus induction dose of 3-4 mg/kg.

Cyclopropyl-MOC-metomidate continuous infusion studies were conducted to determine the minimum effective infusion dose required to induce anesthesia. Anesthesia was induced in rats with a 4 mg/kg IV bolus dose followed by continuous infusion of cyclopropyl-MOC-metomidate at 1 mg/kg/min. When stable anesthesia was observed after 30 minutes of infusion, the infusion rate was reduced to 0.8 mg/kg/min and then to 0.6 mg/kg/min and 0.4 mg/kg/min at 30-minute intervals. Anesthesia and LORR was maintained in all rats at 0.6 mg/kg/min. At 0.4 mg/kg/min all three rats exhibited signs of lightening of anesthesia. In one rat, the infusion at 0.4 mg/kg/min was discontinued after 7 minutes due to inadequate the anesthesia. The other two rats received the full 30-minute infusion at 4 mg/kg/min with no further change. Rats recovered from LORR and resumed normal behavior within 2-6 minutes of stopping the infusion. Based on these observations, the minimum effective infusion dose rate required to maintain anesthesia was determined to be approximately 0.5 mg/kg/min. An independent assessment of "minimal immobilizing infusion rate" of cyclopropyl-MOC-metomidate in rats yielded a value of 0.89±0.18 mg/kg/min.

To determine the anesthetic effects of cyclopropyl-MOC-metomidate in beagle dogs, animals received single IV bolus doses of 0.25, 0.5, 1, 2, 4, 8 or 16 mg/kg. Anesthesia induction was deemed to occur when dogs lost consciousness and muscle tone, could be placed in a laterally recumbent position, and exhibited little or no response to external stimuli.

Cyclopropyl-MOC-metomidate doses of 1.0 mg/kg and greater produced anesthesia in the dogs and the time to return of normal behavior was dose-dependent and similar to that observed in rat. The minimally effective anesthetic dose (MED) in dogs was approximately 1 mg/kg. A bolus dose of 3 or 4 mg/kg induced 3-6 minutes of anesthesia and was selected as an effective and convenient induction dose prior to continuous infusion dosing. A pilot study was conducted in dogs to assess anesthesia induced by cyclopropyl-MOC-metomidate continuous infusion without a bolus induction dosing. Two dogs received cyclopropyl-MOC-metomidate as a 1 mg/kg/min IV infusion without prior bolus administration. Anesthesia onset was observed between 2.5-4.0 minutes after initiation of infusion. Due to the prolonged onset of anesthesia, infusion for anesthesia induction in dogs was judged to be suboptimal for most experimental circumstances, and all subsequent studies were conducted using a IV bolus induction dose of 3-4 mg/kg.

Continuous infusion studies were conducted in 2 dogs by first administering a 4 mg/kg bolus induction dose followed by continuous infusion of cyclopropyl-MOC-metomidate at 1 mg/kg/min. Anesthesia induction was determined using the methods described above. When stable anesthesia was observed after 20-30 minutes of infusion, the infusion rate was reduced incrementally at 10-minute intervals: Dog 1: 0.8-0.5-0.4-0.3 mg/kg/min; Dog 2: 0.7-0.5-0.3 mg/kg/min). Anesthesia was maintained in both dogs at 0.5 mg/kg/min, but was judged to be light at 0.3-0.4 mg/kg/min based on spontaneous movements and response to stimuli. The time to emergence from anesthesia and recovery of normal behavior was rapid and did not vary markedly as a function of the duration of the infusion in the range of 0.5-1 mg/kg/min. The minimum effective (anesthetic) continuous infusion dose rate (infusion MED) of cyclopropyl-MOC-metomidate in dogs was estimated to be approximately 0.5 mg/kg/min. The dog infusion MED was then confirmed in 4 dogs in that first received a 3 mg/kg IV bolus induction dose followed by continuous infusion at 0.5 mg/kg/min for 120 minutes.

Importantly, dogs emerged from cyclopropyl-MOC-metomidate anesthesia in approximately 5 minutes and recovered apparently normal behavior within 10-12 minutes, whether they had received a 4 mg/kg bolus dose or a 4 mg/kg bolus dose bolus induction followed continuous infusion of 0.5 mg/kg/min for 30 or 120 minutes.

Recovery from anesthesia with cyclopropyl-MOC-metomidate is therefore "context-independent" at effective dose ranges, in contrast with the response to other anesthetics. The sedative/hypnotic response and time of emergence and recovery of dogs to cyclopropyl-MOC-metomidate was compared to etomidate and propofol, two commonly used anesthetic agents.

Etomidate was administered to dogs at IV bolus doses ranging from 0.25 to 2 mg/kg. Anesthesia in the dogs was measured as described above. Bolus injections of etomidate induced anesthesia in the range 0.5-2 mg/kg. The bolus dose of 2 mg/kg was adopted to induce anesthesia prior to subsequent continuous infusions.

For continuous infusions, a minimum initial dose rate of 0.15 mg/kg/min was found to be effective. However, after approximately 30 minutes of infusion it was necessary to decrease the infusion rate to 0.1 mg/kg/min due to a decrease in respiratory rate. Emergence and complete recovery from etomidate anesthesia was longer than for cyclopropyl-MOC-metomidate and exhibited marked context-dependency, such that recovery from 30-minute or 120-minute continuous infusion was considerably prolonged relative to recovery from a bolus dose. Notably, dogs experienced extended periods of involuntary movements during the extended period of recovery from etomidate anesthesia.

Propofol was administered to dogs as an IV bolus dose of 5 mg/kg to induce anesthesia followed by a continuous infusion at 0.4 mg/kg/min. Dogs emerged from anesthesia approximately 15 minutes after the end of infusion and recovered normal behavior 30 minutes or more after infusion. Recovery from 120-minute propofol infusion was approximately 3-fold longer than recovery from a cyclopropyl-MOC-metomidate infusion of the same duration.

A well-described in vivo model (Cotton et al., 2009; Pessina et al., 2009) was employed to compare the effects of cyclopropyl-MOC-metomidate with vehicle, etomidate and propofol upon adrenal steroid response to a provocative challenge. Dexamethasone (0.01 mg/kg) was administered two hours before the first administration of ACTH and re-administered every 2 hours to maintain suppression. Dexamethasone pretreatment suppresses the hypothalamo-hypophyseal axis to prevent endogenous ACTH release and subsequent adrenocortical steroid secretion. During dexamethasone suppression, the test substance (cyclopropyl-MOC-metomidate, etomidate, propofol or vehicle) was administered for 30 or 120 min. Synthetic ACTH (Synacthen, 250 µg) was then administered at times after test substance administration to evaluate the effects of the test substance on the release of the adrenal steroid, cortisol. Twenty-two hours after administration of the test substance, dexamethasone was again administered and a single ACTH injection was administered to test adrenal function 24 hours after test substance administration.

The series of studies described below demonstrates that cyclopropyl-MOC-metomidate inhibit adrenal cortisol production only during and immediately after their infusion. Normal adrenal responsiveness returns in all treated dogs within 1.5-3 hours after cessation of infusion and is comparable to that observed following vehicle or propofol infusion. Etomidate, however, produces more profound and durable adrenal suppression. The following day, all treatment groups showed a similar response to ACTH.

TABLE 3

| Study | Dosing regimen bolus (mg/kg) + infusion (mg/kg/min) | Test substance | Time of ACTH administration after infusion (hr) |
|---|---|---|---|
| 1 | 3 + 0.75 | cyclopropyl-MOC-metomidate | 0, 1.5, 2, 24 |
|  | 2 + 0.15/0.10 | etomidate |  |
|  | 3 + 0.75 | vehicle |  |
| 2 | 3 + 0.75 | cyclopropyl-MOC-metomidate | 1.5, 2, 24 |
|  | 5 + 0.4 | Propofol |  |

For Study 1, the objectives were to evaluate the effects on adrenal responsiveness after 120-minute infusions of cyclopropyl-MOC-metomidate or etomidate compared with vehicle. Drugs or vehicle were administered as IV bolus followed by 120 minutes of continuous infusion to dogs in randomized crossover designs. ACTH was administered at the end of the infusion, as well as 90 and 180 minutes after the infusion, and blood samples were taken every 30-60 minutes to measure plasma cortisol concentrations (by ELISA), as well as the concentrations of cyclopropyl-MOC-metomidate and etomidate and their major metabolites.

Following vehicle administration, ACTH provoked a brisk increase in the plasma levels of cortisol that was quite variable among dogs. The second and third ACTH stimuli provoked a further increase or maintenance of elevated plasma cortisol levels. Following etomidate infusion, ACTH-induced increases in plasma cortisol were markedly inhibited and began to rise only with the third ACTH stimulus 180 minutes after infusion and never reached normal (>60% response seen in vehicle) during the 300-minute test period. For cyclopropyl-MOC-metomidate, cortisol response to the first ACTH stimulus was inhibited, but the response to the second and third ACTH stimuli at 90 and 180 minute post-infusion were robust and cortisol levels approached those observed post-vehicle. By 24 hours after infusion, each test substance groups exhibited similar ACTH responses.

In Study 2, cyclopropyl-MOC-metomidate or propofol were infused for 120 minutes, after dexamethasone suppression. All study methods described for Study 1 were repeated, except the ACTH administration at the end of infusion was omitted. Both groups responded in a similar fashion to ACTH challenges given 90 and 180 minutes after the end of infusions, reaching normal cortisol levels within 120 minutes after cessation of test drug administration. Both test groups showed a normal response to ACTH challenge the following day.

The pharmacokinetics of ABP-700 and its major metabolite, CPM-acid, was studied in rats following IV bolus injection and IV bolus followed by infusion for 60 minutes.

Cyclopropyl-MOC-metomidate was administered to rats at IV bolus doses of 4, 8, 12 & 16 mg/kg, and blood samples were taken at time points ranging from 30 seconds to 24 hours. Levels of cyclopropyl-MOC-metomidate and CPM-acid were determined using LC-MS or LC-MS/MS. Cyclopropyl-MOC-metomidate levels exhibited a rapid first-phase >10-fold decline during the first 5 minutes. This decline is at least partially due to rapid metabolism to CPM-acid, since it was present in the 30-second samples at levels comparable to cyclopropyl-MOC-metomidate and continued to rise to reach a peak in the 12-minute samples. The first phase of cyclopropyl-MOC-metomidate decline also presumably reflects rapid tissue distribution, as indicated by the rapid onset of anesthesia following IV bolus injection. Cyclopropyl-MOC-metomidate and CPM-acid exhibited secondary terminal elimination with half-lives of approximately 10 minutes and 20 minutes, respectively. Both cyclopropyl-MOC-metomidate and CPM-acid were below the levels of quantification (0.1 ng/mL and 5 ng/mL, respectively) in 24-hour PK samples. No difference in cyclopropyl-MOC-metomidate PK was observed between male and female rats. Cyclopropyl-MOC-metomidate levels were approximately dose-proportional.

The PK profile of cyclopropyl-MOC-metomidate after continuous IV infusion in rats was also examined. Rats first received an IV bolus of 4 mg/kg to induce anesthesia followed by continuous infusion of cyclopropyl-MOC-metomidate at 2 mg/kg/min or 4 mg/kg/min for 60 minutes. Blood samples were taken at time points ranging from 30 seconds to 24 hours. Levels of cyclopropyl-MOC-metomidate and CPM-acid were determined using LC-MS or LC-MS/MS. Samples drawn 5, 30 or 60 minutes after the beginning of continuous infusion indicated that levels of both cyclopropyl-MOC-metomidate and CPM-acid rose gradually through the infusion, appearing to approach steady state levels by 60-minute and were approximately dose-proportional. During the first 30 minutes following discontinuation of infusion, cyclopropyl-MOC-metomidate levels exhibited a rapid ~50-fold decline. This was followed by a slower secondary phase of decline with a half-life of ~20 minutes.

The pharmacokinetics of cyclopropyl-MOC-metomidate and its major metabolite, CPM-acid, was studied in dogs following IV bolus injection and IV bolus followed by continuous infusion for 60 minutes.

Cyclopropyl-MOC-metomidate was administered to dogs at IV bolus doses of 0.25, 1, 2, 4, and 12 mg/kg, and blood samples were taken at time points ranging from 30 seconds to 24 hours. Levels of cyclopropyl-MOC-metomidate and CPM-acid were determined using LC-MS. Cyclopropyl-MOC-metomidate levels exhibited a rapid first-phase >10- fold decline during the first 5-10 minutes. Cyclopropyl-MOC-metomidate and CPM-acid exhibited secondary terminal elimination with half-lives in dogs of approximately 5-10 minutes and 20-30 minutes, respectively. Both cyclopropyl-MOC-metomidate and CPM-acid were below the levels of quantification (0.1 ng/mL and 5 ng/mL, respectively) in 24-hour PK samples. Cyclopropyl-MOC-metomidate levels were approximately dose-proportional. No difference in cyclopropyl-MOC-metomidate PK was observed between male and female dogs.

The initial decline of cyclopropyl-MOC-metomidate is at least partially due to metabolism of cyclopropyl-MOC-metomidate to CPM-acid, since it was present in the 30-second sample and continued to rise during the first 5-10 minutes. However, the rise in CPM-acid levels was initially slower than in rats, so the first phase of cyclopropyl-MOC-metomidate decline also presumably reflects rapid tissue distribution, as indicated by the rapid onset of anesthesia following IV bolus injection, followed by metabolism in a peripheral compartment(s).

Cyclopropyl-MOC-metomidate was also administered to dogs at 4 mg/kg IV bolus induction dose followed by continuous infusion of doses ranging from 0.5-4 mg/kg/min for 30-120 minutes. Blood samples were taken at time points ranging from 30 seconds to 24 hours. Levels of cyclopropyl-MOC-metomidate and CPM-acid were determined using LC-MS or LC-MS/MS. Samples drawn 5, 30 or 60 minutes after the beginning of continuous infusion indicated that levels of cyclopropyl-MOC-metomidate were roughly constant during infusion, while levels of the CPM-acid, rose gradually through the infusion, appearing to approach steady state levels by the 60-minute sample that were approximately dose-proportional. During the first 10-30 minutes following discontinuation of infusion, cyclopropyl-MOC-metomidate levels exhibited a rapid ~50-fold decline. This was followed by a slower secondary phase of decline with a half-life of ~20 minutes.

Predominant metabolism of cyclopropyl-MOC-metomidate to CPM-acid was evident as CPM-acid reached concentrations approximately 10-fold higher than cyclopropyl-MOC-metomidate by the end of infusion, and then declined following the infusion at a rate similar to the secondary elimination of cyclopropyl-MOC-metomidate. Concentrations of both cyclopropyl-MOC-metomidate and CPM-acid were near or below the levels of quantification in 24-hour PK samples. Similar post-infusion pharmacokinetics were observed in a study with a 120-minute infusion at 0.75 mg/kg/min.

Pharmacokinetic and toxicokinetic studies in rats and dogs confirm that following intravenous administration of cyclopropyl-MOC-metomidate, the drug is both rapidly distributed to induce sedation/hypnosis, and rapidly metabolized to form CPM-acid. With both bolus and continuous infusion administration, venous blood concentrations observed when rats and dogs were sedated/anesthetized were greater than ~250 ng/mL, or ~0.8 µM, consistent with the minimum concentrations that activated GABA receptor/channels expressed in *Xenopus* oocytes by 10-20%. Following bolus or discontinuation of infusion the levels of cyclopropyl-MOC-metomidate fell quickly below this threshold, allowing rapid emergence from anesthesia and sedation. Second-phase elimination was rapid following bolus, but appeared to be somewhat prolonged following more extended continuous infusion, particularly at high dose. Cyclopropyl-MOC-metomidate exposure increased in approximately dose-proportional manner up to maximally tolerated doses/concentration, as outlined in Table 4.

TABLE 4

| Study | Dosing regimen bolus (mg/kg) + infusion (mg/kg/min) | Test substance | Time of ACTH administration after infusion (hr) |
|---|---|---|---|
| 1 | 3 + 0.75 | cyclopropyl-MOC-metomidate | 0, 1.5, 2, 24 |
|   | 2 + 0.15/0.10 | etomidate |   |
|   | 3 + 0.75 | vehicle |   |
| 2 | 3 + 0.75 | cyclopropyl-MOC-metomidate | 1.5, 2, 24 |
|   | 5 + 0.4 | Propofol |   |

*AUC estimates calculated by scaling from actual measurements.
MED—minimum effective dose;
MTD—maximum tolerated dose;
$C_{30\ sec}$—blood concentration 30 seconds after bolus;
$C_{EOI}$—blood concentration at end of infusion

REFERENCES

1. Ebert T J, Muzi M, Berens R, Goff D, Kampine J P: Sympathetic responses to induction of anesthesia in humans with propofol or etomidate. Anesthesiology 1992; 76: 725-33
2. Sarkar M, Laussen P C, Zurakowski D, Shukla A, Kussman B, Odegard K C: Hemodynamic responses to etomidate on induction of anesthesia in pediatric patients. Anesth Analg 2005; 101: 645-50, table of contents
3. Boisson-Bertrand D, Taron F, Laxenaire M C: Etomidate vs. propofol to carry out suspension laryngoscopies. Eur J Anaesthesiol 1991; 8: 141-4
4. Diago M C, Amado J A, Otero M, Lopez-Cordovilla J J: Anti-adrenal action of a subanaesthetic dose of etomidate. Anaesthesia 1988; 43: 644-5
5. den Brinker M, Hokken-Koelega A C, Hazelzet J A, de Jong F H, Hop W C, Joosten K F: One single dose of etomidate negatively influences adrenocortical performance for at least 24[Symbol: see text]h in children with meningococcal sepsis. Intensive Care Med 2007
6. Wagner R L, White P F: Etomidate inhibits adrenocortical function in surgical patients. Anesthesiology 1984; 61: 647-51
7. Wagner R L, White P F, Kan P B, Rosenthal M H, Feldman D: Inhibition of adrenal steroidogenesis by the anesthetic etomidate. N Engl J Med 1984; 310: 1415-21
8. Vinclair M, Broux C, Faure P, Brun J, Genty C, Jacquot C, Chabre O, Payen J F: Duration of adrenal inhibition following a single dose of etomidate in critically ill patients. Intensive Care Med 2007
9. Jackson W L, Jr.: Should we use etomidate as an induction agent for endotracheal intubation in patients with septic shock?: a critical appraisal. Chest 2005; 127: 1031-8
10. Cuthbertson B H, Sprung C L, Annane D, Chevret S, Garfield M, Goodman S, Laterre P F, Vincent J L, Freivogel K, Reinhart K, Singer M, Payen D, Weiss Y G: The effects of etomidate on adrenal responsiveness and mortality in patients with septic shock. Intensive Care Med 2009
11. Lipiner-Friedman D, Sprung C L, Laterre P F, Weiss Y, Goodman S V, Vogeser M, Briegel J, Keh D, Singer M, Moreno R, Bellissant E, Annane D: Adrenal function in sepsis: the retrospective Corticus cohort study. Crit Care Med 2007; 35: 1012-8
12. Cotten J F, Husain S S, Forman S A, Miller K W, Kelly E W, Nguyen H H, Raines D E: Methoxycarbonyl-etomidate: a novel rapidly metabolized and ultra-shortacting etomidate analogue that does not produce prolonged adrenocortical suppression. Anesthesiology 2009; 111: 240-9
13. Pejo E, R. G, Banacos N, Cotten J F, Husain S S, Raines D E: Electroencephalographic recovery, hypnotic emergence, and the effects of metabolite following continuous infusions of a rapidly metabolized eomidate analog in rats. Anesthesiology 2012; Accepted
14. Bodor N, Buchwald P: Soft drug design: general principles and recent applications. Med Res Rev 2000; 20: 58-101
15. Buchwald P, Bodor N: Physicochemical aspects of the enzymatic hydrolysis of carboxylic esters. Pharmazie 2002; 57: 87-93
16. Calvo R, Carlos R, Erill S: Etomidate and plasma esterase activity in man and experimental animals. Pharmacology 1979; 18: 294-8
17. Feldman P L, James M K, Brackeen M F, Bilotta J M, Schuster S V, Lahey A P, Lutz M W, Johnson M R, Leighton H J: Design, synthesis, and pharmacological evaluation of ultrashort- to long-acting opioid analgetics. J Med Chem 1991; 34: 2202-8
18. Quon C Y, Stampfli H F: Biochemical properties of blood esmolol esterase. Drug Metab Dispos 1985; 13: 420-4
19. Bartlett P D, Rylander P N: β-Propriolactone. XII Mechanisms involved in the reaction of β-propriolactone with acids and bases. J Amer Chem Soc. 1951; 73: 4273-4
20. Waud D R: On biological assays involving quantal responses. J Pharmacol Exp Ther 1972; 183: 577-607
21. Liao M, Sonner J M, Husain S S, Miller K W, Jurd R, Rudolph U, Eger E I, 2nd: R (+) etomidate and the photoactivable R (+) azietomidate have comparable anesthetic activity in wild-type mice and comparably decreased activity in mice with a N265M point mutation in the gamma-aminobutyric acid receptor beta3 subunit. Anesth Analg 2005; 101: 131-5, table of contents
22. Shafer S L: Principles of Pharmacokinetics and Pharmacodynamics, Anesthesiology, Principles and Practice of Anesthesiology. Edited by Longnecker D E, Tinker J H, Morgan G E. St. Louis, Mosby, 1998, pp 1159-210
23. Pejo E, Cotton J F, Kelly E W, Le Ge R, Cuny G D, Laha J K, Liu J, Lin X J, Raines D E: In Vivo and In Vitro Pharmacological Studies of Methoxycarbonyl-Carboetomidate. Anesth Analg 2012. In Press
24. Van Hamme M J, Ghoneim M M, Ambre J J: Pharmacokinetics of etomidate, a new intravenous anesthetic. Anesthesiology 1978; 49: 274-7
25. Minagawa T, Kohno Y, Suwa T, Tsuji A: Species differences in hydrolysis of isocarbacyclin methyl ester (TEI-9090) by blood esterases. Biochem Pharmacol 1995; 49: 1361-5
26. Wang S, Yang J, Peng Y, Zou Y, Xiang H, Yao H, Chen J, Bi D, Yao J: Species-dependent plasma metabolism of the ester compound daidzein 7,4'di-succinic acid monester-O-ethoxy (DZ5). Pharmazie 2007; 62: 574-6
27. Kam S T, Matier W L, Mai K X, Barcelon-Yang C, Borgman R J, O'Donnell J P, Stampfli H F, Sum C Y, Anderson W G, Gorczynski R J, et al.: [(Arylcarbonyl) oxy]propanolamines. 1. Novel beta-blockers with ultrashort duration of action. J Med Chem 1984; 27: 1007-16
28. Buchwald P: Structure-metabolism relationships: steric effects and the enzymatic hydrolysis of carboxylic esters. Mini Rev Med Chem 2001; 1: 101-11
29. Buchwald P, Bodor N: Quantitative structure-metabolism relationships: steric and nonsteric effects in the enzymatic hydrolysis of noncongener carboxylic esters. J Med Chem 1999; 42: 5160-8
30. Laumen K, Schneider M P: A highly selective ester hydrolase from *Pseudomonas* Sp. for the enzymatic preparation of enantiomerically pure secondary alcohols; chiral auxiliaries in organic synthesis. J Soc Chem Commun 1988: 598-600
31. Quon C Y, Mai K, Patil G, Stampfli H F: Species differences in the stereoselective hydrolysis of esmolol by blood esterases. Drug Metab Dispos 1988; 16: 425-8
32. Krasowski M D, Jenkins A, Flood P, Kung A Y, Hopfinger A J, Harrison N L: General anesthetic potencies of a series of propofol analogs correlate with potency for potentiation of gamma-aminobutyric acid (GABA) current at the GABA(A) receptor but not with lipid solubility. J Pharmacol Exp Ther 2001; 297: 338-51
33. Ge R. L., E. Pejo, M. Haburcak, S. S. Husain, S. A. Forman and D. E. Raines, Pharmacological studies of methoxycarbonyl etomidate's carboxylic acid metabolite. *Anesthesia & Analgesia* 2011; 115: 305-8.
34. Cotton, J. F., Husain, S., Forman, S. A., et al., Methoxycarbonyl-etomidate. Anesthesiology 2009; 111: 240-249.
35. Pessina, P., A. Fernandez-Foren, E. Cueto, L. Delucchi, V. Castillo and A. Meikle, Cortisol secretion after adrenocorticotrophin (ACTH) and dexamethasone tests in healthy female and male dogs. *Acta Vet. Scandinavica* 2009; 51: 33-38.

What is claimed is:

1. A compound of formula (I):

$$(I)$$

wherein:

$R^1$ is $L^1C(O)OL^2$-$[C(R^7R^8)]_p$—$C(R^9R^{10})$—$C(O)OT$;

$R^2$ is $R^1$, optionally substituted linear or branched $C_1$-$C_{10}$ alkyl, optionally substituted linear or branched $C_2$-$C_{10}$ alkenyl, or optionally substituted linear or branched $C_2$-$C_{10}$ alkynyl, wherein the backbone of $C_1$-$C_{10}$ alkyl, $C_2$-$C_{10}$ alkenyl, or $C_2$-$C_{10}$ alkynyl optionally comprises one or more heteroatoms;

each $R^3$ is independently halogen, CN, $CF_3$, $SR^2$, $SOR^2$, $SO_2R^2$, $OR^2$, $CO_2H$, $CO_2R^2$, $N(R^2)_2$, $NHR^2$, $NO_2$, or $R^2$;

Z is N or $CR^6$;

$R^4$, $R^5$, and $R^6$ are independently hydrogen, halogen, CN, $CF_3$, $SR^2$, $SOR^2$, $SO_2R^2$, $OR^2$, $CO_2H$, $CO_2R^2$, $N(R^2)_2$, $NHR^2$, $NO_2$, or $R^2$;

$R^7$ and $R^8$ are hydrogen;

$R^9$ and $R^{10}$ are independently hydrogen, optionally substituted aryl or optionally substituted heteroaryl;

$L^1$ and $L^2$ are independently a bond, optionally substituted linear or branched $C_1$-$C_{10}$ alkylene, optionally substituted linear or branched $C_2$-$C_{10}$ alkenylene, or optionally substituted linear or branched $C_2$-$C_{10}$ alkynylene, wherein the backbone of $C_1$-$C_{10}$ alkylene, $C_2$-$C_{10}$ alkenylene, or $C_2$-$C_{10}$ alkynylene optionally comprises one or more heteroatoms;

T is H, a linear or branched, substituted or unsubstituted $C_1$-$C_{10}$ alkyl, linear or branched, substituted or unsubstituted $C_2$-$C_{10}$ alkenyl, linear or branched, substituted or unsubstituted $C_2$-$C_{10}$ alkynyl, optionally substituted cyclyl, optionally substituted heterocylcyl, optionally substituted aryl, optionally substituted heteroaryl, or PEG, wherein the backbone of $C_1$-$C_{10}$ alkyl, $C_2$-$C_{10}$ alkenyl, $C_2$-$C_{10}$ alkynyl optionally comprises one or more heteroatoms;

n is an integer from 0-5; and p is 0 or 1, or a salt, solvate, or ester thereof, provided that when both of $R^9$ and $R^{10}$ are hydrogen then T is optionally substituted aryl, optionally substituted heteroaryl or a linear or branched $C_1$-$C_{10}$ alkyl substituted with a heterocyclyl.

2. The compound of claim 1, wherein Z is N.

3. The compound of claim 1, wherein T is morpholinyl, oxazolindinyl or oxetanyl.

4. The compound of claim 1, wherein T is methyl or ethyl.

5. The compound of claim 1, wherein $R^2$ is methyl, ethyl, n-propyl, isopropyl, butyl, sec-butyl, iso-butyl, tert-butyl, pentyl, neopentyl, hexyl, 2-methylpentyl, 3-methylpentyl, 2,3-dimethylbutyl, or 2,2-dimethylbutyl.

6. The compound of claim 1, wherein $R^4$ and $R^5$ are hydrogen.

7. The compound of claim 1, wherein $R^9$ and $R^{10}$ are hydrogen.

8. The compound of claim 1, wherein one of $R^9$ and $R^{10}$ is hydrogen and the other is optionally substituted aryl or optionally substituted heteroaryl.

9. The compound of claim 1, wherein n is 0.

10. The compound of claim 1, wherein $L^1$ is a bond.

11. The compound of claim 1, wherein $L^2$ is a bond.

12. The compound of claim 1, wherein n is 0; $L^1$ and $L^2$ are a bond; $R^2$ is a $C_1$-$C_{10}$ alkyl; and $R^4$ and $R^5$, and $R^6$ are hydrogen.

13. The compound of claim 1, wherein the compound is selected from the group consisting of:

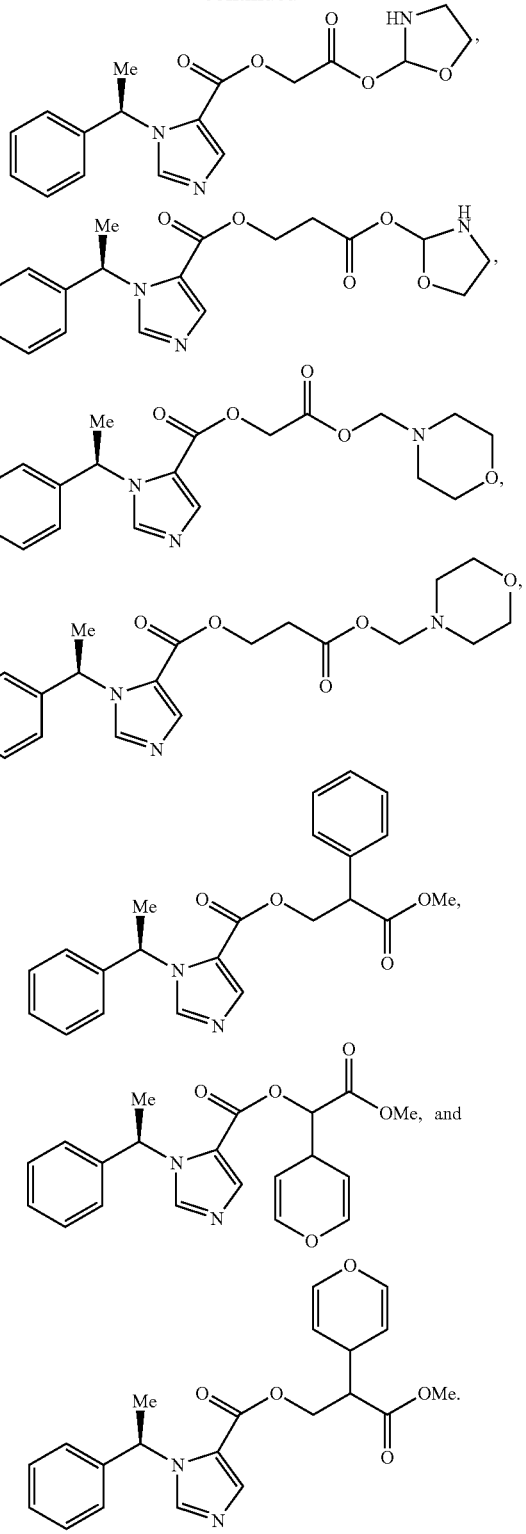

14. A pharmaceutical composition comprising a compound of claim 1 and a pharmaceutically acceptable excipient.

15. A method for providing anesthesia or sedation to a subject comprising administering to the subject a therapeutically effective amount of a compound of claim 1.

16. The method of claim 15, wherein the compound is administered intravenously.

17. The method of claim 16, wherein the compound is administered as a single intravenous bolus, as a continuous intravenous infusion, or a combination thereof.

18. The method of claim 15, wherein the subject is human.

19. The method of claim 15, wherein the compound is administered in a pharmaceutical composition comprising one or more pharmaceutically acceptable excipients.

20. The method of claim 15, further comprising administering an analgesic agent, a paralytic agent, or both an analgesic agent and a paralytic agent.

* * * * *